United States Patent [19]
Green et al.

[11] Patent Number: 5,326,013
[45] Date of Patent: Jul. 5, 1994

[54] SELF CONTAINED GAS POWERED SURGICAL APPARATUS

[75] Inventors: David T. Green, Westport; Keith Ratcliff, Sandy Hook; Keith L. Milliman, Norwalk; Henry R. Sienkiewicz, Stamford; Mitchell J. Palmer, New Milford, all of Conn.

[73] Assignee: United States Surgical Corporation, Norwalk, Conn.

[21] Appl. No.: 949,685

[22] Filed: Sep. 23, 1992

Related U.S. Application Data

[63] Continuation-in-part of Ser. No. 915,425, Jul. 17, 1992, abandoned, which is a continuation-in-part of Ser. No. 781,012, Oct. 18, 1991, abandoned.

[51] Int. Cl.$^5$ .......................................... A61B 17/072
[52] U.S. Cl. .................................. 227/176; 227/180; 227/19
[58] Field of Search ................. 227/19, 175, 179, 180, 227/176

[56] References Cited

U.S. PATENT DOCUMENTS

| | | |
|---|---|---|
| 3,079,606 | 5/1963 | Bobrov et al. . |
| 3,490,675 | 1/1970 | Green et al. . |
| 3,499,591 | 3/1970 | Green . |
| 3,593,903 | 7/1971 | Astafiev et al. . |
| 3,618,842 | 11/1971 | Bryan . |
| 3,643,851 | 2/1972 | Green et al. . |
| 3,662,939 | 5/1972 | Bryan . |
| 3,675,688 | 7/1972 | Bryan et al. . |
| 3,717,294 | 2/1973 | Green . |
| 3,735,762 | 5/1973 | Bryan et al. . |
| 3,788,303 | 1/1974 | Hall . |
| 3,815,476 | 6/1974 | Green et al. . |
| 3,837,555 | 9/1974 | Green . |
| 3,892,228 | 7/1975 | Mitsui . |
| 4,086,926 | 5/1978 | Green et al. . |
| 4,111,206 | 9/1978 | Vishnevsky et al. . |
| 4,207,873 | 6/1980 | Kruy . |
| 4,331,277 | 5/1982 | Green . |
| 4,349,028 | 9/1982 | Green . |
| 4,429,695 | 2/1984 | Green . |
| 4,562,839 | 1/1986 | Blake, III et al. . |
| 4,606,343 | 8/1986 | Conta et al. . |
| 4,610,383 | 9/1986 | Rothfuss et al. . |
| 4,688,555 | 8/1987 | Wardle . |
| 4,728,020 | 3/1988 | Green et al. ..................... 227/19 |
| 4,763,669 | 8/1988 | Jaeger ................................. 30/251 |
| 4,784,137 | 11/1988 | Kulik et al. . |
| 4,821,942 | 4/1989 | Richards et al. . |
| 4,880,015 | 11/1989 | Nierman . |
| 4,944,443 | 7/1990 | Oddsen et al. . |
| 5,018,657 | 5/1991 | Pedlick et al. . |
| 5,040,715 | 8/1991 | Green et al. . |
| 5,042,707 | 8/1991 | Taheri ................................. 227/19 |
| 5,047,038 | 9/1991 | Peters et al. . |
| 5,071,430 | 12/1991 | de Salis et al. . |

FOREIGN PATENT DOCUMENTS

| | | | |
|---|---|---|---|
| 728848 | 5/1980 | U.S.S.R. ........................... 227/19 |
| 1352554 | 5/1974 | United Kingdom . |

OTHER PUBLICATIONS

Swain, C. P., Brown, G. J. and Mills, T. N., "An Endoscopic Stapling Device: The Development of a New Flexible Endoscopically Controlled Device for Placing Multiple Transmural Staples in Gastrointestinal Tissue", *Gastrointestinal Endoscopy*, 1989, vol. 35, No. 4, pp. 338–339.

*Primary Examiner*—Scott Smith

[57] ABSTRACT

A self contained gas powered endoscopic surgical apparatus is provided for placing lateral lines of surgical fasteners into body tissue. The apparatus includes a frame portion, an elongated portion extending from the frame portion, and an articulating cartridge assembly mounted to a distal end of the elongated portion. An anvil member is operatively associated with the articulating cartridge assembly and has a forming surface thereon against which surgical fasteners are driven as they are ejected from the cartridge assembly. A collar which is provided in the elongated portion translates longitudinally to draw a cable which operates to move the anvil member relative to the cartridge assembly, thereby clamping body tissue to be fastened. A self contained pneumatic system is associated with the frame portion and is actuable to eject the surgical fasteners from the cartridge assembly. A linkage mechanism is also provided for effectuating the articulation of the cartridge assembly to increase the range of operability of the apparatus.

38 Claims, 39 Drawing Sheets

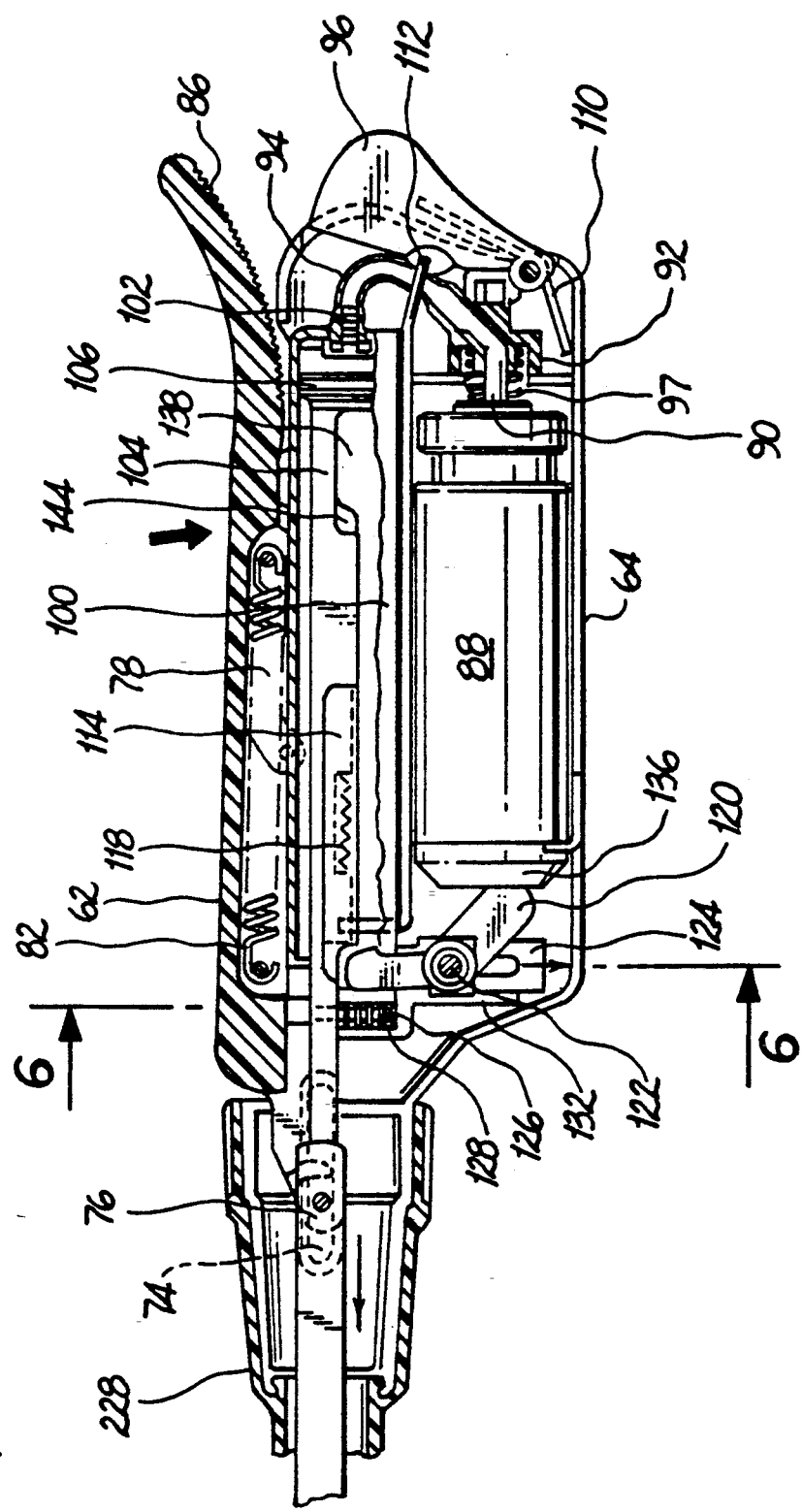

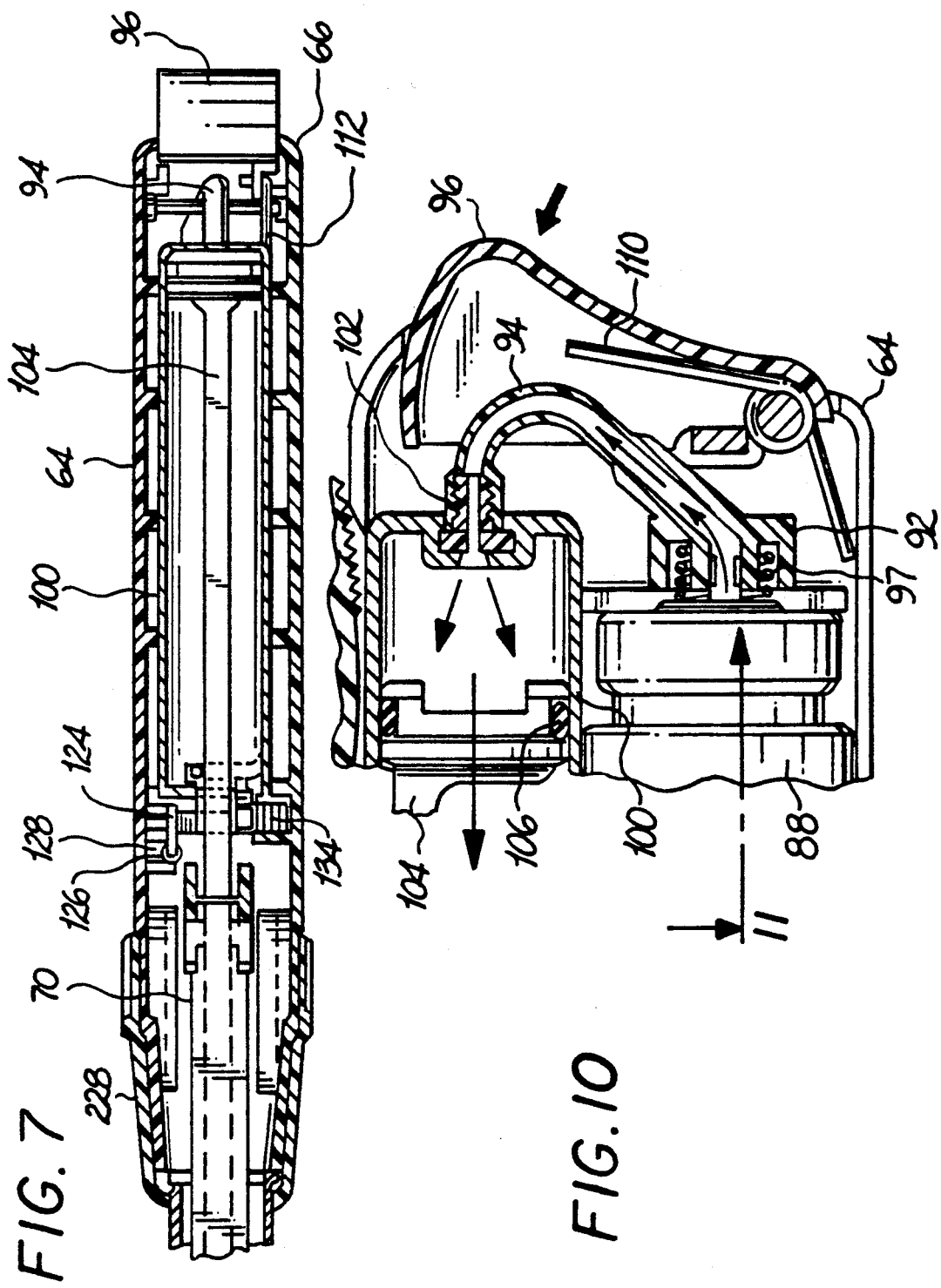

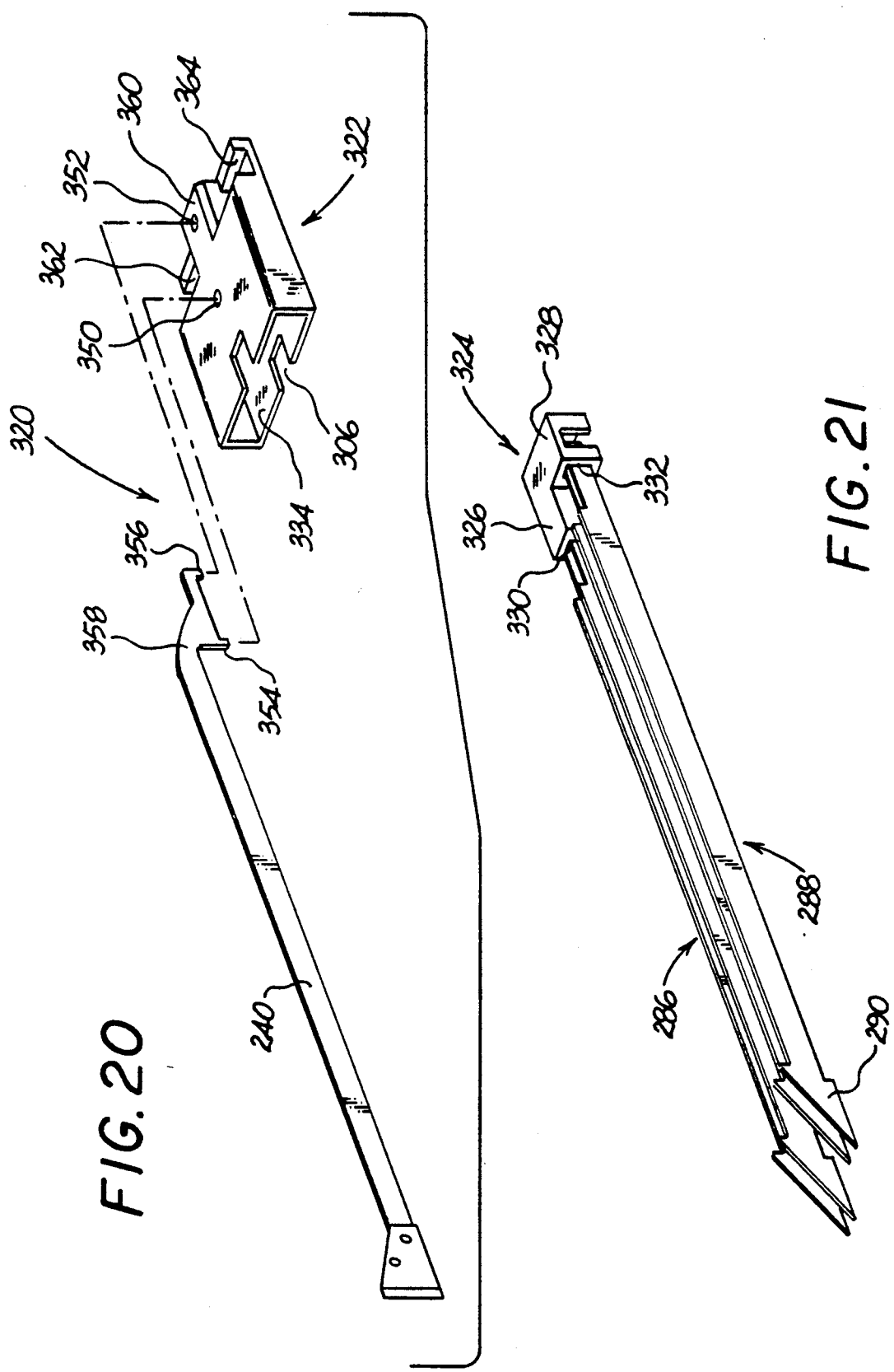

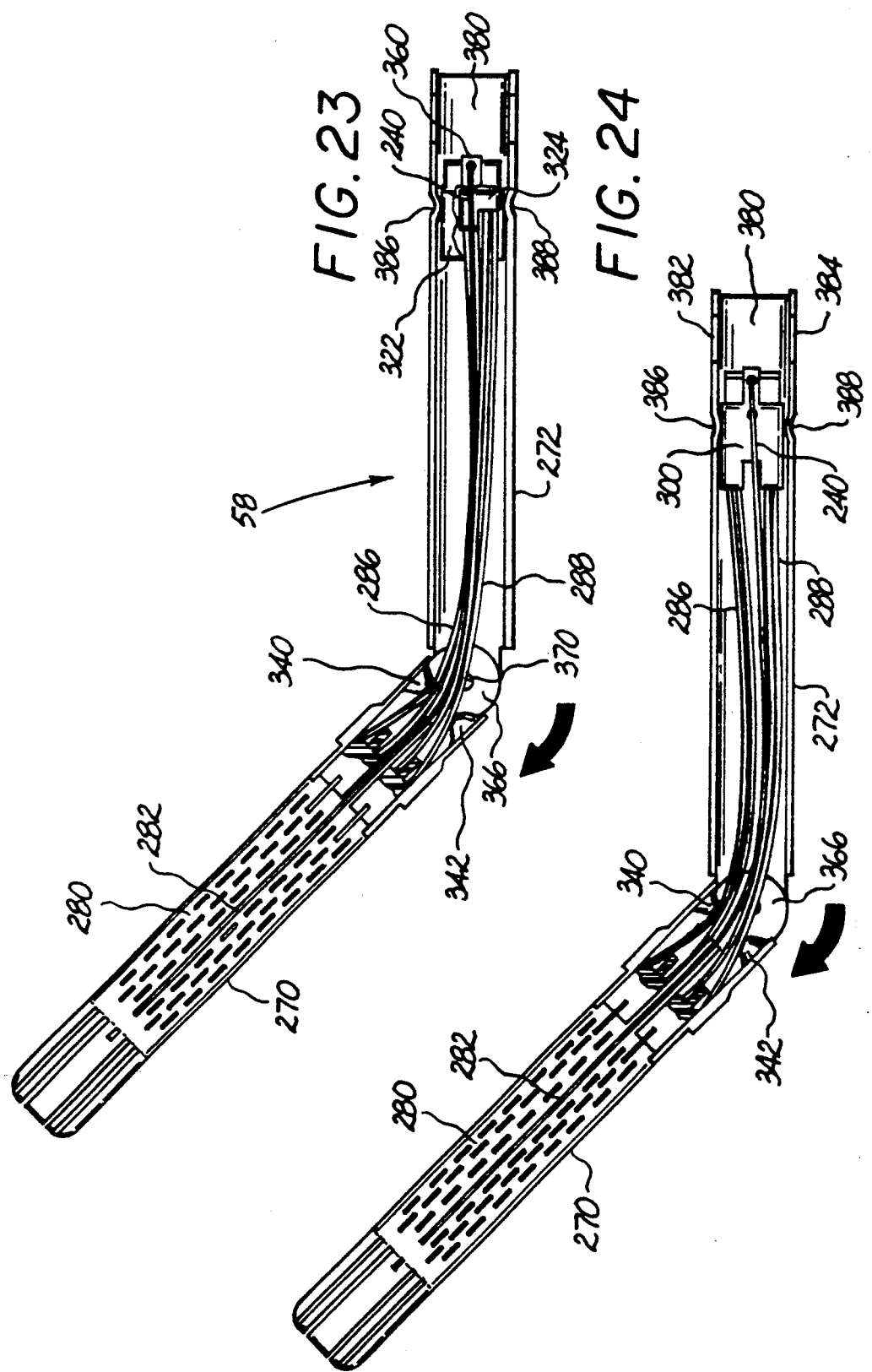

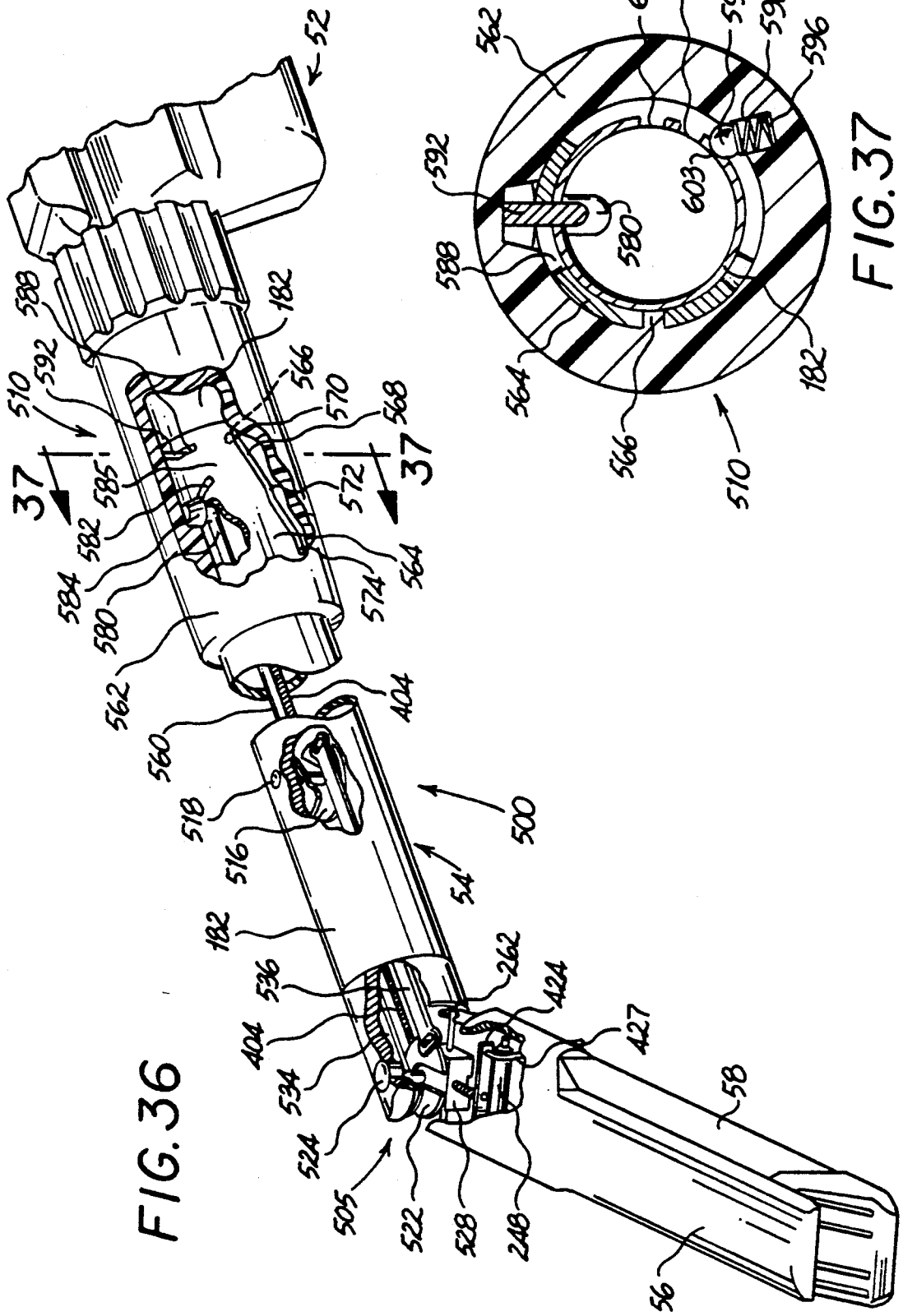

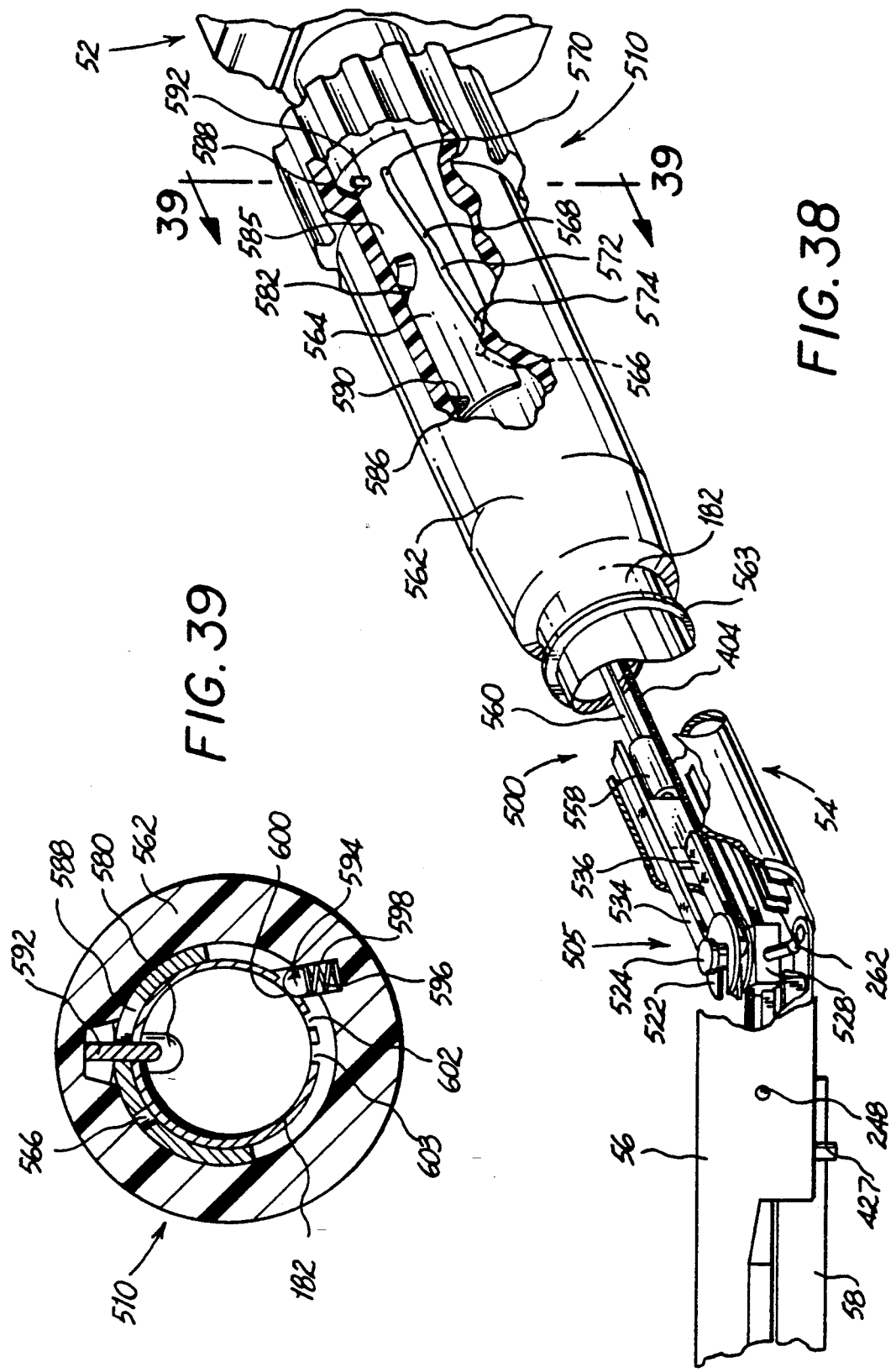

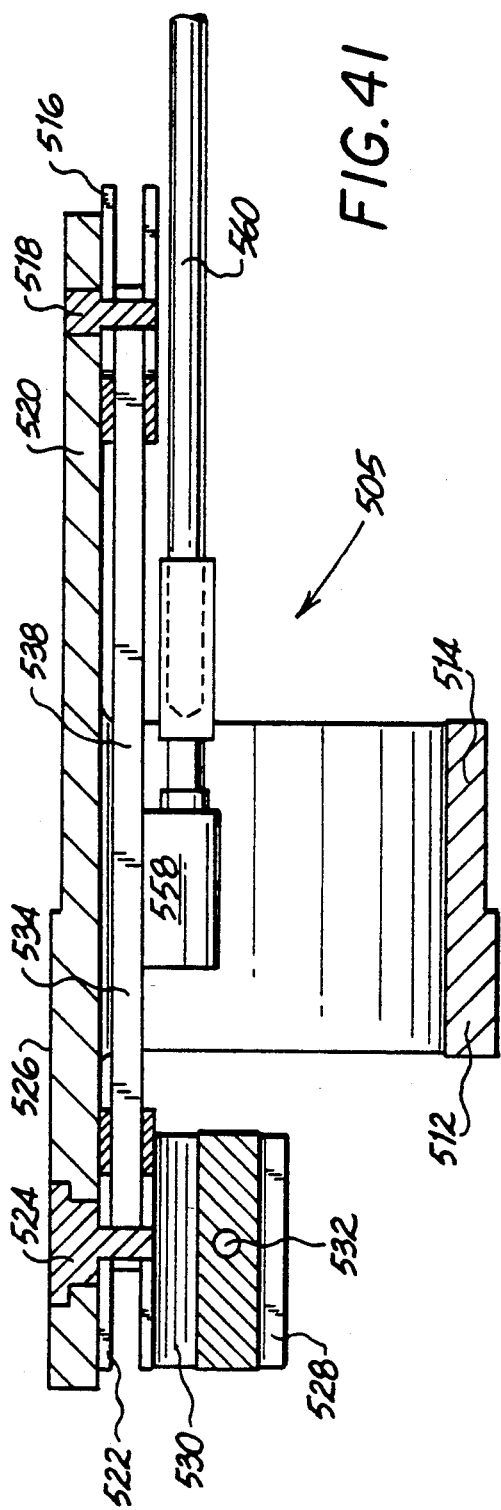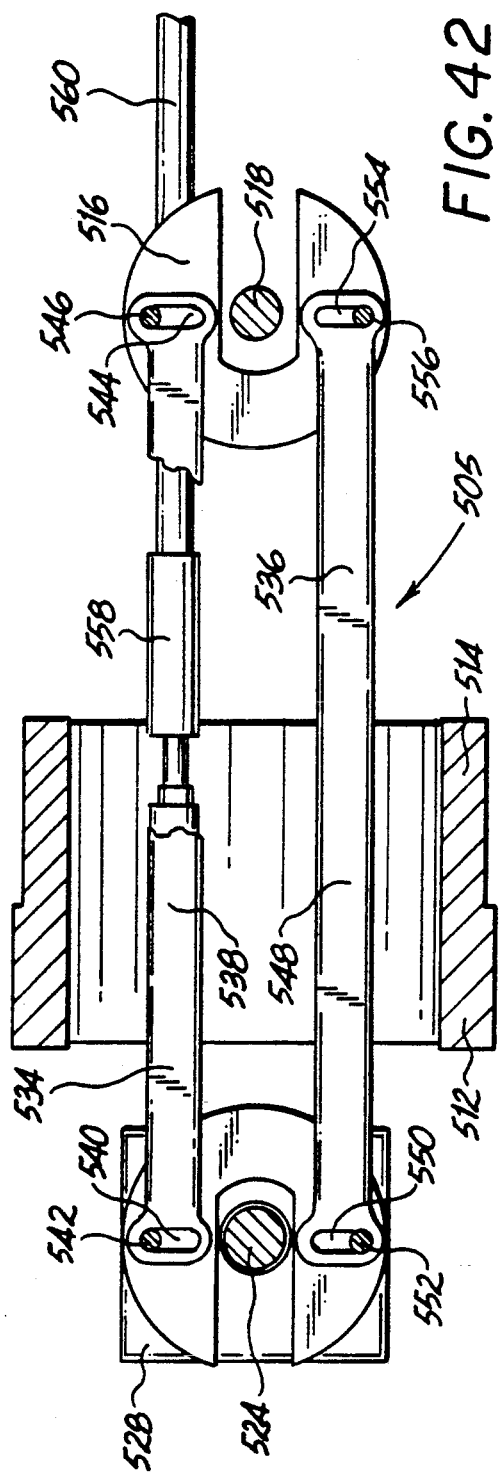

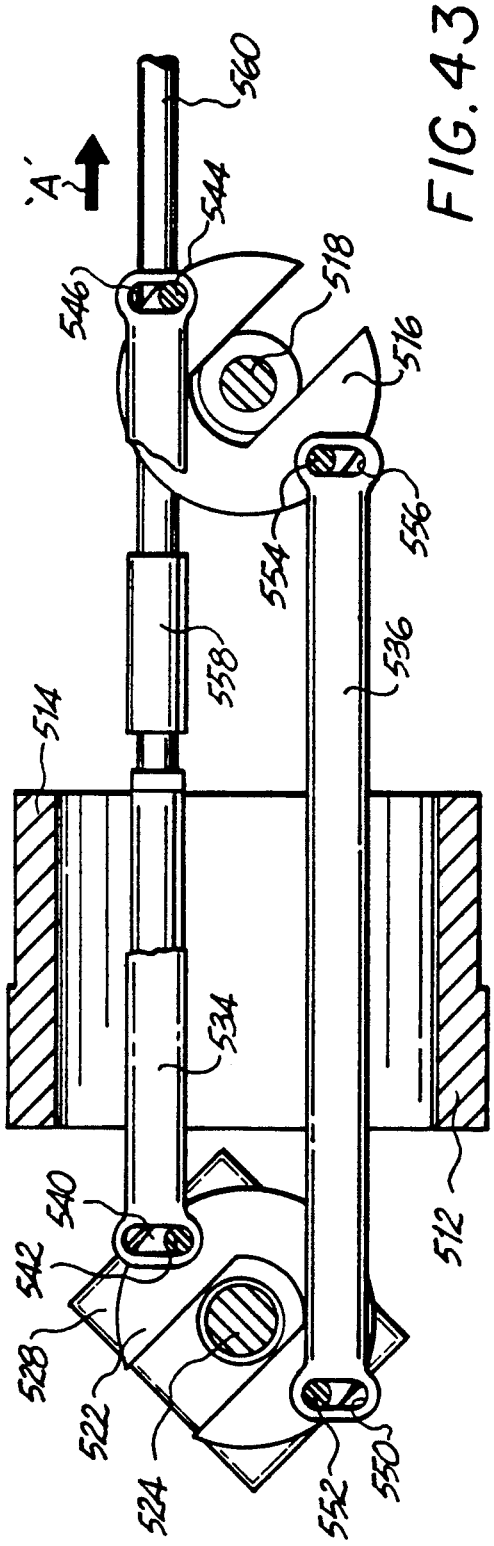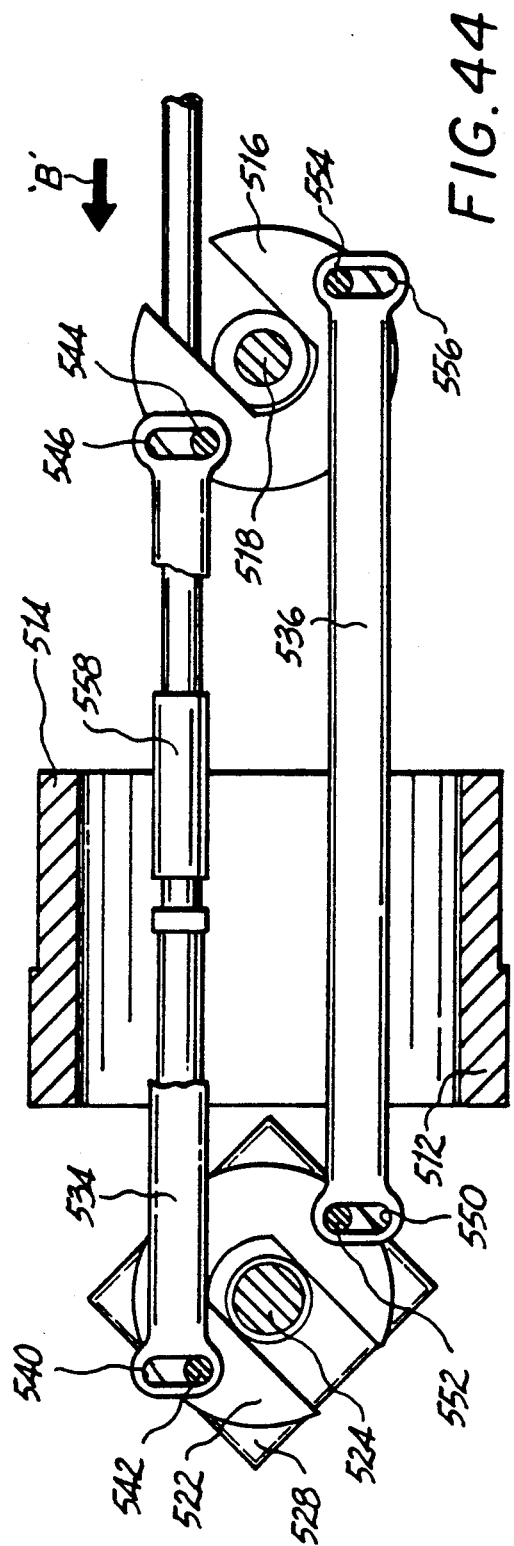

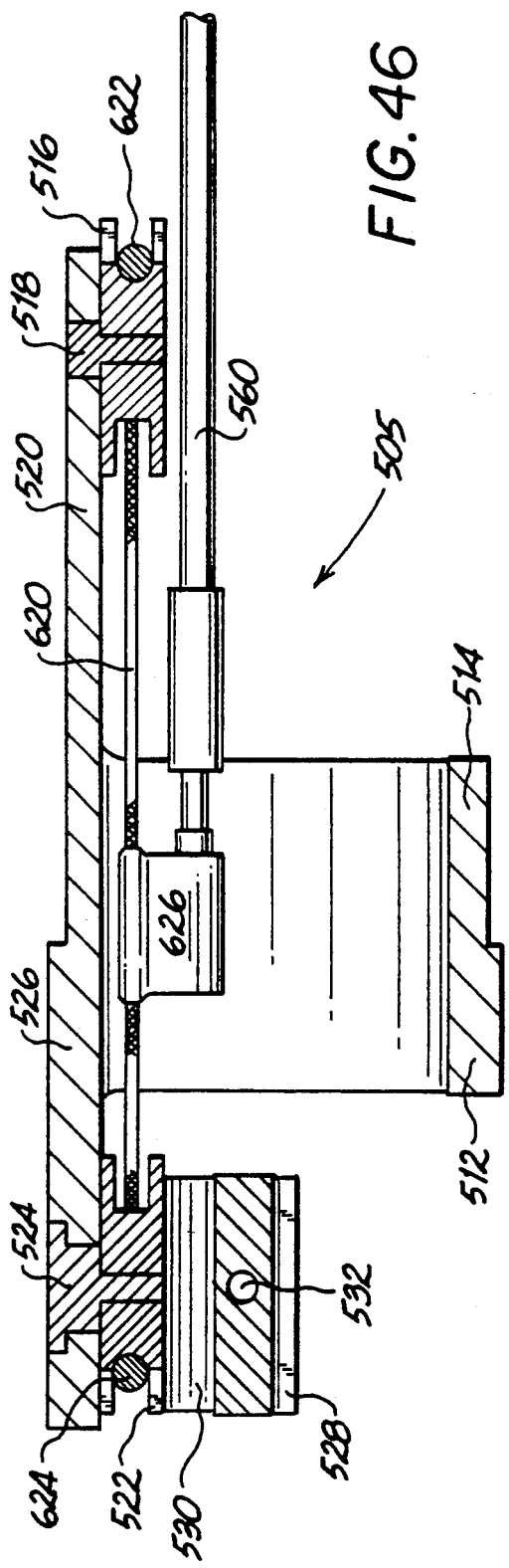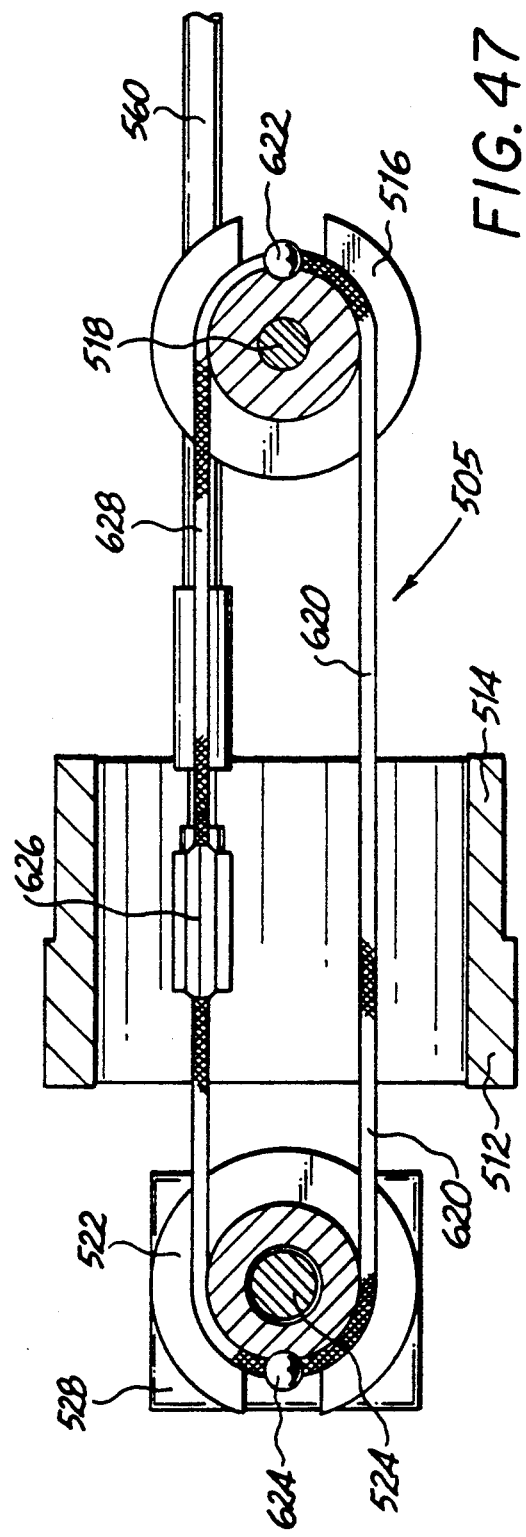

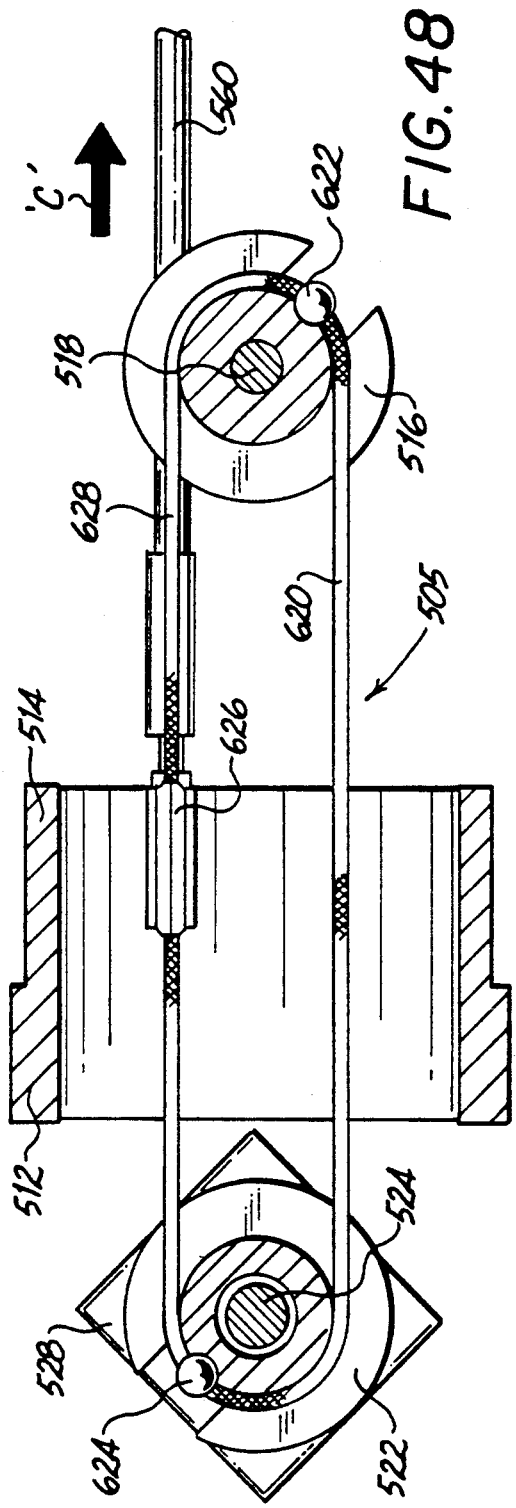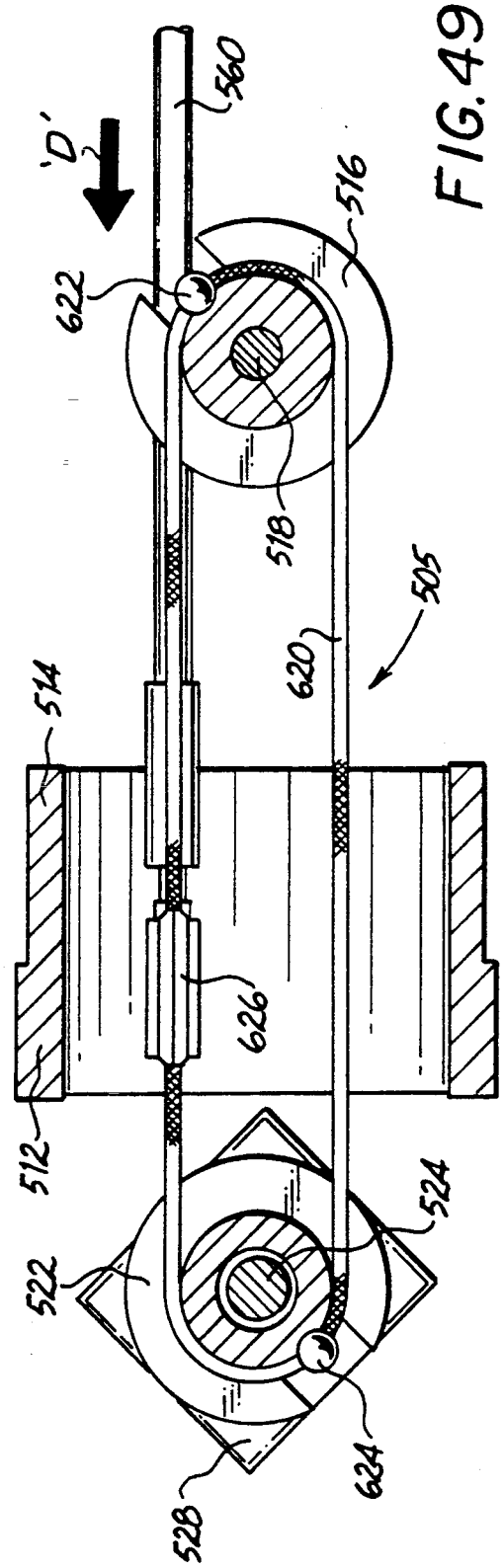

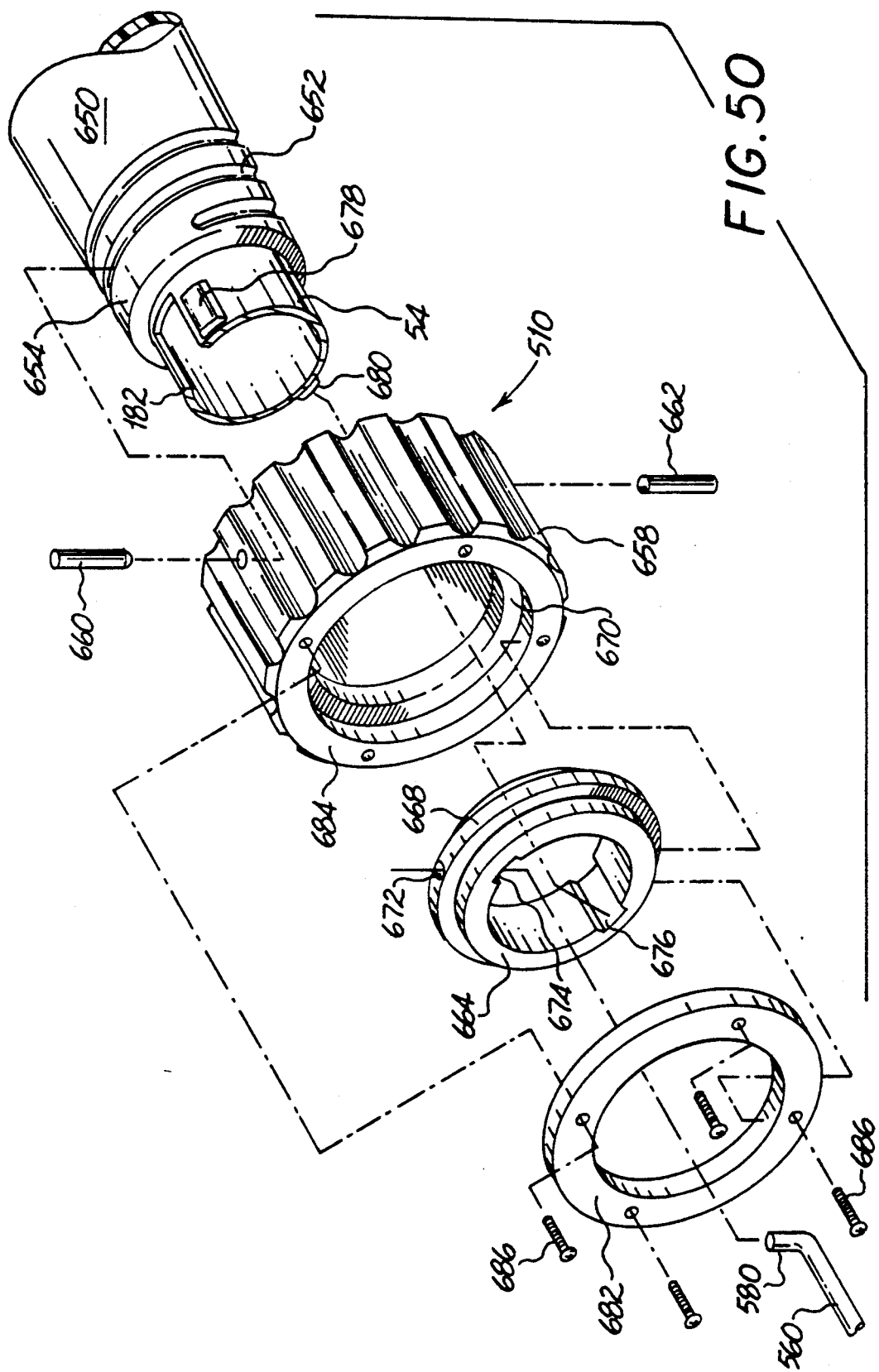

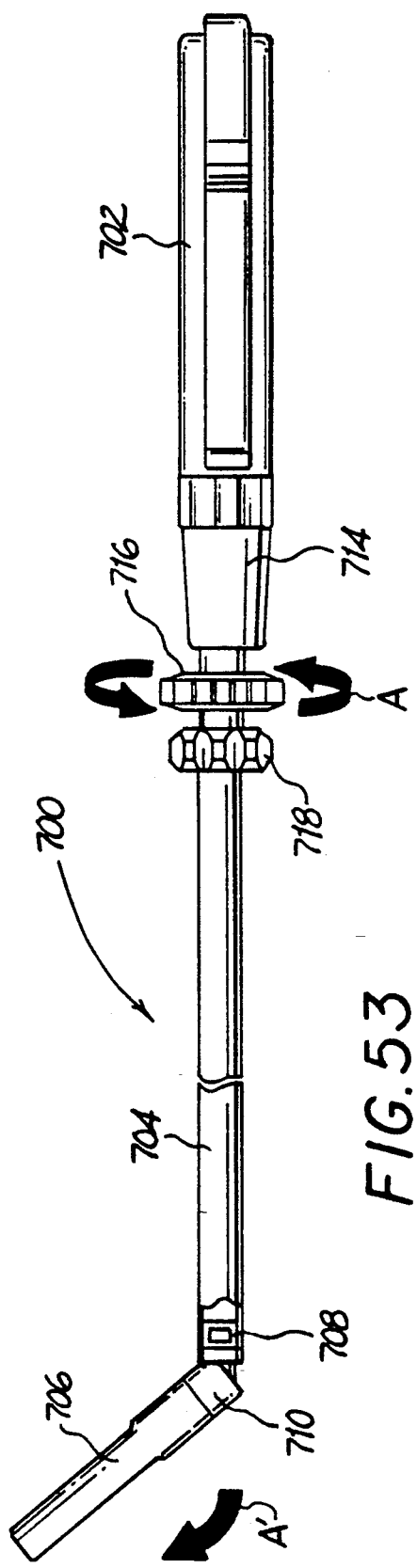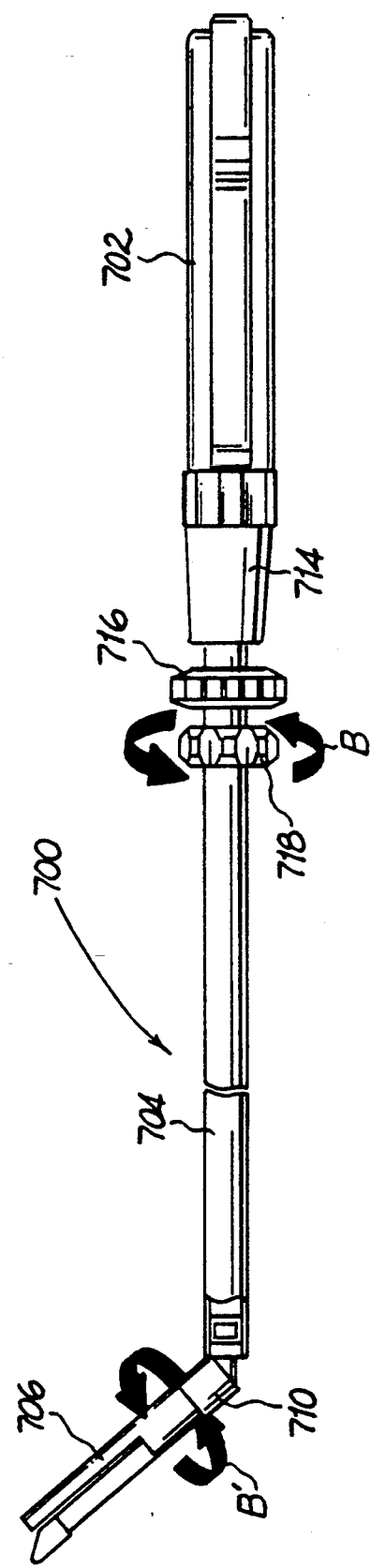

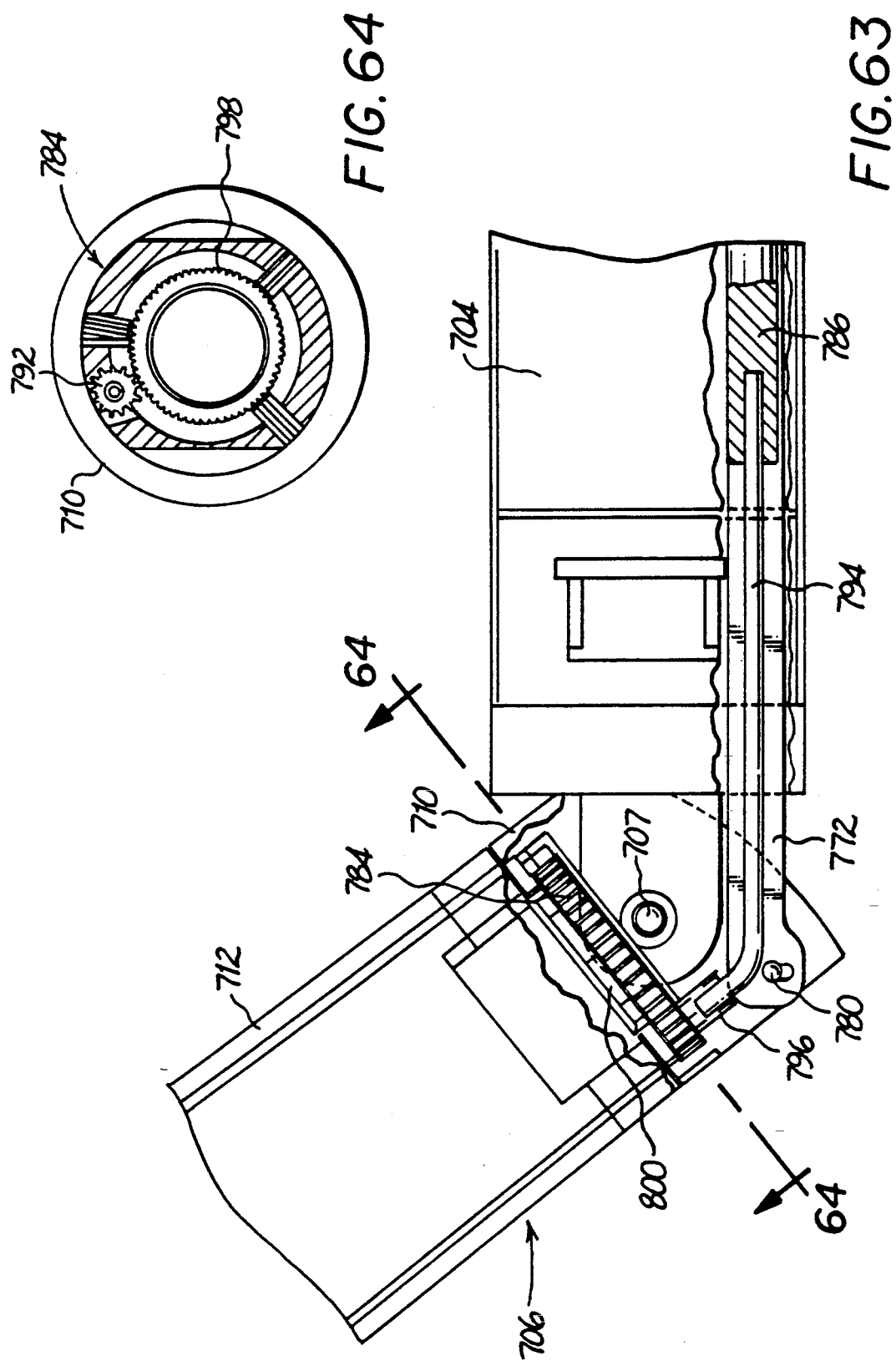

SELF CONTAINED GAS POWERED SURGICAL APPARATUS

CROSS REFERENCE TO RELATED APPLICATIONS

This application is a continuation-in-part of copending application Ser. No. 07/915,425, filed Jul. 17, 1992, now abandoned, which is a continuation-in-part of copending application Ser. No. 07/781,012, filed Oct. 18, 1991, now abandoned.

BACKGROUND OF THE INVENTION

1. Field of the Invention

This invention relates to surgical stapling apparatus, and more particularly to surgical apparatus which are powered by self contained relatively low pressure gas systems to perform sequential operations such as tissue clamping, staple forming and/or tissue cutting.

2. Description of Related Art

Surgical stapling apparatus is known wherein tissue is first grasped or clamped between opposing jaw structure and then fastened by means of fasteners. In some instruments a knife is provided to cut tissue which has been joined. The fasteners are typically in the form of surgical staples. However, two part polymeric type fasteners are also known.

Instruments for this purpose can comprise two elongated fingers which are respectively used to capture or clamp tissue. Typically, one of the fingers carries a disposable cartridge housing wherein a plurality of staples are arranged in at least two lateral rows while the other finger comprises an anvil for curling the staple legs into a hook-like configuration upon their being driven against the anvil. The stapling operation is effected by a pusher which travels longitudinally along the cartridge carrying finger, with the pusher acting upon the staples to place rows of staples in body tissue A knife may be optionally positioned in such a manner so as to operate sequentially immediately behind the pusher, and laterally positioned between the staple rows to longitudinally cut and/or open the stapled tissue between the rows of staples. Such instruments are disclosed in Bobrov et al. (U.S. Pat. No. 3,079,606) and Green (U.S. Pat. No. 3,490,675). These instruments comprise apparatus for simultaneously making a longitudinal incision and applying a row of staples on both sides of the incision.

A later development disclosed in Green (U.S. Pat. No. 3,499,591) applies a double row of staples on each side of the incision. This is accomplished by a cartridge assembly wherein a cam member moves within a guide path between two sets of staggered staple carrying grooves. Staple drive members located within the grooves each have two staple pusher plates, and sloping surfaces disposed within the guide path so as to be contacted by the longitudinally moving cam and be driven along the groove to effect ejection of two staples.

The cartridge assemblies typically come in a plurality of sizes, each varying in both length and number of staples contained therein. Depending on the procedure to be performed, the surgeon must select the appropriate cartridge assembly. No provision is currently available to adjust the firing means of the instrument itself so that a wide variety of staple driving sequences may be accomplished using a single staple cartridge assembly.

The instruments described above were all designed to be used in surgical procedures wherein surgeons have direct manual access to the operation site. However, in endoscopic or laparoscopic procedures surgery is performed through a small incision or through narrow cannulae inserted through small entrance wounds in the skin. In order to address the specific needs of endoscopic and/or laparoscopic surgical procedures, an endoscopic surgical stapling apparatus such as that shown in Green et al. (U.S. Pat. No. 5,040,715) has been developed. This apparatus is well suited for such procedures and incorporates a distal end having an anvil and staple cartridge assembly and a manually operated handle assembly interconnected by an endoscopic portion which permits the instrument to be inserted into a cannula and be remotely operated by the surgeon.

The instruments discussed above all require some degree of manually applied force in order to clamp, fasten and/or cut tissue. This manual application can prove awkward or difficult depending upon the orientation of the instrument relative to the surgeon, the type of tissue being operated on or the ability of the surgeon to apply the necessary force. Furthermore, because of the difficulty and expense of cleaning and sterilizing surgical instruments between uses, there is increasing interest in and demand for instruments which are disposable after use in a single surgical procedure rather than permanent and reusable. Self contained gas powered surgical staplers are known, as shown, for example, in U.S. Pat. Nos. 3,618,842; 3,643,851; 3,662,939; 3,717,294; 3,815,476; and 3,837,555. Typically, these staplers include a replaceable cylinder which supplies gas (e.g., carbon dioxide or nitrogen) at relatively high pressure (e. g., 800 p.s.i.g.) for powering the instrument. The high pressure gas used in these staplers requires that the staplers be of relatively heavy construction in order to accommodate the high pressure involved. Because of their construction, these instruments are relatively expensive to manufacture and therefore often intended to be relatively permanent and reusable.

Use of a relatively low pressure gas is advantageous to enable a stapler to be made of lighter construction and less expensive materials. This is desirable to lower the cost and make the stapler economically disposable. The stapler must, however, be capable of generating the substantial forces required to form the staples. Typically, the staples are metal wire which is partially formed prior to use and which must be further formed (e.g., crimped against an anvil) by the stapler. To generate the relatively large forces required to form the staples with low pressure gas would ordinarily require a relatively large pneumatic actuator. This is undesirable because a large actuator makes the stapler bulky and difficult to work with. In addition, a large actuator unnecessarily consumes a large amount of gas during the portion of actuator motion when relatively large forces are not required, i.e., during the first part of the actuator stroke when the staple is merely being advanced to the staple forming position. The gas which is thus effectively wasted substantially reduces the number of stapling operations which can be performed by the stapler before its gas supply is exhausted. This substantially shortens the useful life of the stapler if the gas supply is not replaceable, and even if the gas supply is replaceable, it undesirably increases the frequency with which the gas supply must be replaced.

Although it may be desirable to perform functions of the stapling apparatus automatically using the self-powering elements in the apparatus, it may also be desirable for the initial function to be at least partly manual. For example, if the initial function is tissue clamping, it may be preferable to initiate such function manually so that it can be performed slowly and precisely and the results inspected and corrected if necessary before the automatic self-powered portion of the operating sequence begins. See, for example, U.S. Pat. Nos. 4,349,028 and 4,331,277 to Green.

Many of the instruments described above are limited in their range of operability. Improvements have been made in the art of surgical instruments to increase their range of operability. For example Nierman (U.S. Pat. No. 4,880,015) discloses a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle through the distal to the shaft for controlling the angular rotation of the distal portion of the instrument.

In accordance with these and other principles, it is an object of the present invention to provide a self contained gas powered surgical instrument for driving surgical fasteners into body tissue which instrument has an increased range of operability.

It is another object of the present invention to provide a self contained gas powered surgical apparatus insertable through a small incision or narrow tube for driving surgical fasteners into body tissue and cutting the body tissue between rows of staples.

It is still another object of the present invention is to provide a self contained gas powered surgical apparatus which is disposable after use.

Another object of the present invention is to provide a self contained gas powered surgical apparatus having a mechanism which will prevent clamping of tissue unless the cartridge has been properly inserted in the instrument.

Yet another object of the present invention is to provide a self contained gas powered surgical apparatus having sealing structure for inhibiting the escape of insufflation gas through the apparatus.

Another object of the present invention is to provide a self contained gas powered surgical apparatus having counter structure for displaying the number of times the instrument has been fired.

A further object of the present invention is to provide a self contained gas powered surgical apparatus with structure to disable the apparatus after a predetermined number of firings have occurred.

SUMMARY OF THE INVENTION

The objects of the invention are accomplished by providing a self contained endoscopic surgical instrument which is at least partially operable by means of a relatively low pressure pneumatic assembly. The surgical instrument in accordance with an embodiment of the present invention is a surgical stapling apparatus which is adapted for placing one or more longitudinal rows of staples. This apparatus may further include a knife for making an incision in body tissue between the rows of staples. The latter configuration may find particular use of adjoining two hollow organs or in removing an organ, such as the appendix, the gallbladder, etc.

In a preferred embodiment of the subject invention the endoscopic stapler comprises a frame portion, an elongated tubular body portion extending from the frame portion and adapted for receiving an articulating cartridge assembly. The articulating cartridge assembly includes a cartridge mounting portion removably maintained in a distal end portion of the tubular body portion and a cartridge housing portion which is pivotally connected to the cartridge mounting portion. In one embodiment, articulation means is provided, including a cable loop assembly associated with the tubular body portion of the instrument for effectuating the articulation of the cartridge housing portion relative to the cartridge mounting portion of the cartridge assembly. The cable loop assembly includes a cable member, a pivot block member mounted for rotation in a distal end portion on the tubular body portion about an axis perpendicular to the longitudinal axis thereof, and a rotation control member operatively associated with the tubular body portion of the apparatus for manipulating the cable loop assembly. cartridge element, which includes a plurality of surgical staples slidably mounted therein, and having a tissue engaging surface, is receivable within the cartridge housing portion of the cartridge assembly. An anvil member is also provided which has a staple forming surface formed thereon and which is mounted adjacent the cartridge housing portion of the cartridge assembly such that the anvil member is movable between an open position and a closed position wherein the staple forming surface is in close cooperative alignment with the tissue engaging surface of the cartridge element.

The apparatus further comprises means associated with the tubular body portion for moving the anvil member between the open and the closed positions, and means for ejecting the surgical staples from the cartridge element in such a manner so as to cause the staples to engage and from on the staple forming surface of the anvil member. The means for moving the anvil member comprises a linkage mechanism associated with the frame portion and extending into the tubular body portion to a cable mechanism. The cable mechanism includes a cable member mounted at a leading end thereof to the linkage mechanism and at a trailing end thereof to the cartridge housing portion of the cartridge assembly. The anvil member is operatively associated with the cable member intermediate the ends thereof. The means for ejecting the surgical fasteners comprises a plurality of pusher elements in abutment with the surgical fasteners, and at least one cam bar for actuating the pusher elements. The cam bar is mounted in an adapter which translates within the cartridge assembly. In one embodiment of the cartridge assembly, the cam bar is fixedly mounted in the adapter while in another embodiment the cam bar is freely movable within the adapter.

The articulating cartridge assembly of the subject invention is also provided with bearing means for guiding the translation of the cam bars as they traverse the cartridge assembly at such times when the cartridge housing portion of the cartridge assembly is articulated relative to the cartridge mounting portion thereof.

A self contained pneumatic system is disposed in the frame portion of the instrument and includes a supply of relatively low pressure gas connected to a pneumatic actuator mechanism. The pneumatic actuator mechanism actuates the means for ejecting the surgical fasteners from the cartridge element. More particularly, the actuator mechanism is operatively connected to the cam bar adapter. Alternatively, the apparatus may be manually operable by the user.

The surgical apparatus of the subject invention may further comprise sealing means associated with the tubular body portion of the instrument for prohibiting the egress of insufflation gas therethrough during surgical procedures.

The surgical instrument may be constructed either as a reusable unit or as a single use, disposable unit or, alternatively may be formed with a reusable handle portion and replaceable body portions and/or staple carrying cartridges.

The present invention advantageously permits surgeons to perform internal surgical procedures including stapling and/or cutting simply by manually clamping the tissue to be manipulated and pneumatically actuating the jaw members. This results in greater convenience and ease of use of the instrument as well as more uniform actuation of the instrument mechanisms.

Further features of the invention, its nature, and various advantages will become more apparent from the accompanying drawings and the following detailed description of the invention.

BRIEF DESCRIPTION OF THE DRAWINGS

Preferred embodiments of the invention are described hereinbelow with reference to the drawings wherein:

FIG. 5 is a side plan view in cross section showing the frame and pneumatic assembly in the clamped and unfired position;

FIG. 7 is a top plan view in cross section taken along line 7—7 of FIG. 3 showing the frame and pneumatic assembly of the surgical instrument;

FIG. 10 is a side cut away view in cross section showing the operation of the pneumatic assembly of the present invention as it is fired;

FIG. 20 is an enlarged perspective view of the external portion of the cam bar adapter shown in FIG. 23;

FIG. 21 is an enlarged perspective view of the internal cam bar maintaining element of the cam bar adapter shown in FIG. 23;

FIG. 23 is a top plan view of the cartridge assembly of the FIG. 18 showing an adapter for freely maintaining the distal end portions of the cam bars;

FIG. 24 is a top plan view of the cartridge assembly of FIG. 18 showing an adapter for fixedly maintaining the distal end portions of the cam bars;

FIGS. 33-35 are top plan views of the cartridge assembly of the apparatus of FIG. 1 in an articulated position illustrating a complete firing sequence wherein:

FIG. 33 illustrates the prefiring position of the cam bar adapter;

FIG. 34 illustrates the cam bar adapter in the fully fired position;

FIG. 35 shows the return stroke of the cam bar adapter within the cartridge assembly;

FIG. 36 is an enlarged perspective view, partially cut-away, of another embodiment of the surgical instrument in accordance with the subject invention in a first articulated position;

FIG. 37 is a cross-sectional view taken along line 37—37 of FIG. 36;

FIG. 38 is an enlarged perspective view, partially cut-away, of the surgical instrument of FIG. 36 in a second articulated position;

FIG. 39 is a cross-sectional view taken along line 39—39 of FIG. 38;

FIG. 41 is a cross-sectional view taken along line 41—41 of FIG. 40;

FIG. 42 is a cross-sectional view taken along line 42—42 of FIG. 40;

FIG. 43 is a cross-sectional view taken along line 42—42 of FIG. 40, illustrating a first operational position of the mechanism of FIG. 40;

FIG. 44 is a cross-sectional view taken along line 42—42 of FIG. 40, illustrating a second operational position of the mechanism of FIG. 40;

FIG. 46 is a cross-sectional view taken along line 46—46 of FIG. 45;

FIG. 47 is a cross-sectional view taken along line 47—47 of FIG. 45;

FIG. 48 is a cross-sectional view taken along line 47—47 of FIG. 45, illustrating a first operational position of the mechanism of FIG. 45;

FIG. 49 is a cross-sectional view taken along line 47—47 of FIG. 45, illustrating a second operational position of the mechanism of FIG. 45;

FIG. 50 is an exploded perspective view of yet another embodiment of the actuation member associated with the mechanism for effectuating the articulation of the surgical instrument of FIG. 36.

DETAILED DESCRIPTION OF THE PREFERRED EMBODIMENTS

Figure 1:
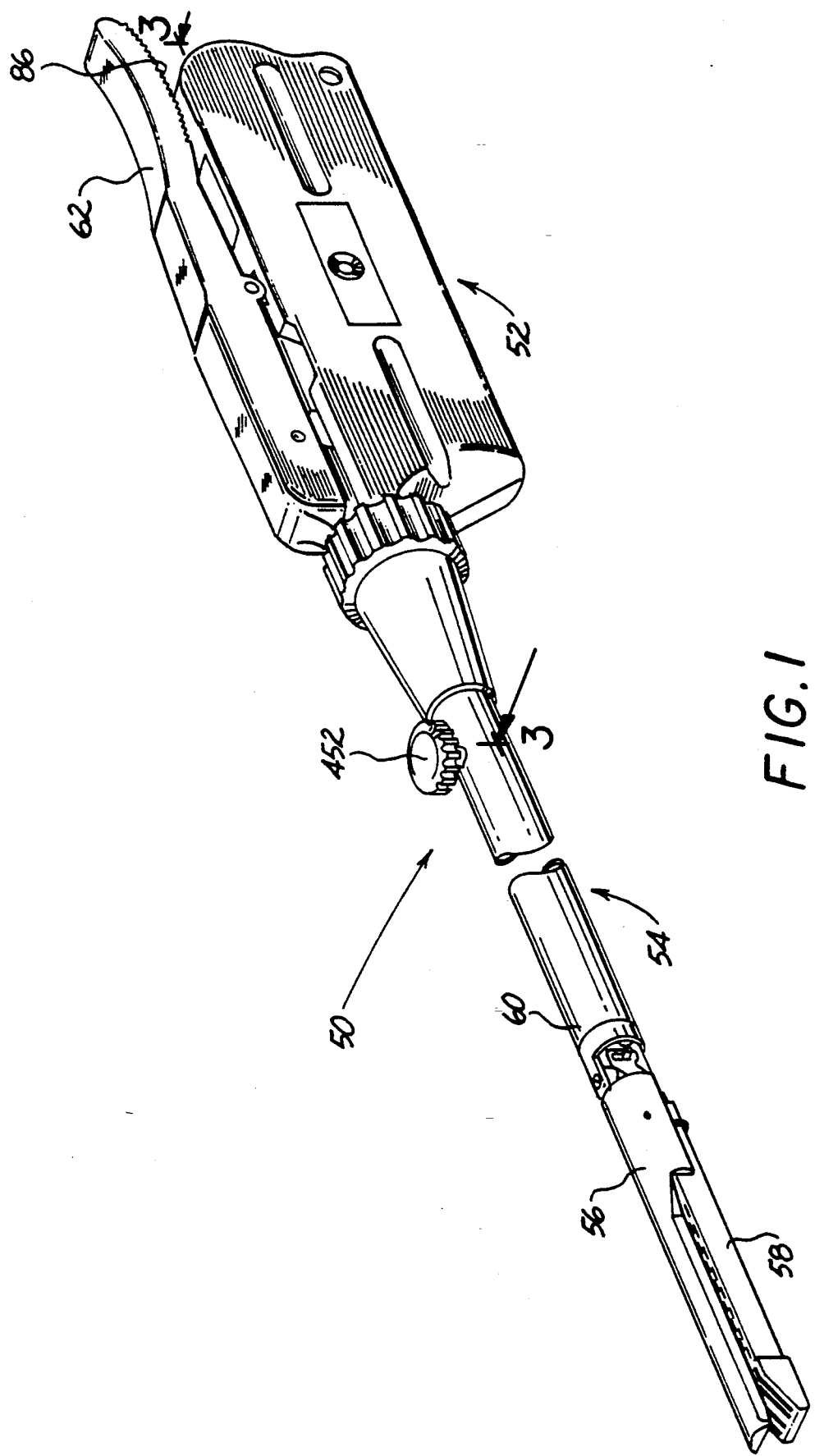
FIG. 1 is a perspective view of a self contained gas powered endoscopic surgical instrument in accordance with the present invention.

It is generally accepted that endoscopic procedures are more common than laparoscopic procedures. Accordingly, the present invention shall be discussed in terms of endoscopic procedures and apparatus. However, use herein of terms such as "endoscopic", "endoscopically" and "endoscopic portion", among others, should not be construed to limit the present invention to a stapling and cutting apparatus for use only in conjunction with an endoscopic tube. On the contrary, it is believed that the present invention may find use in any procedure where access is limited to a small incision, including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disposed therein.

In the drawings and the description which follows, as is customary, the term "proximal" refers to the end which is closest to the operator while the term "distal" will refer to the end which is furthest from the operator.

Referring to FIG. 1, a self contained gas powered endoscopic surgical apparatus constructed in accordance with the principles of the present invention is illustrated and is designated generally by reference numeral 50. Surgical apparatus 50 essentially comprises a frame portion 52 and an elongated portion 54. An anvil member 56 and an articulating cartridge assembly 58 are preferably removably mounted in a distal end portion 60 of elongated portion 54. Anvil member 56 and cartridge assembly 58 are manually controlled by means of an articulating handle 62 associated with frame portion 52. More particularly, handle 62 interconnects with anvil member 56 by means of a linkage and cable assembly which is associated with the elongated portion 54 such that when handle 62 is articulated from an open position (see FIG. 3) to a closed position (see FIG. 5), anvil member 56 is moved into close approximation with the articulating cartridge assembly 58. This operation will be discussed in greater detail hereinbelow.

Figure 2:
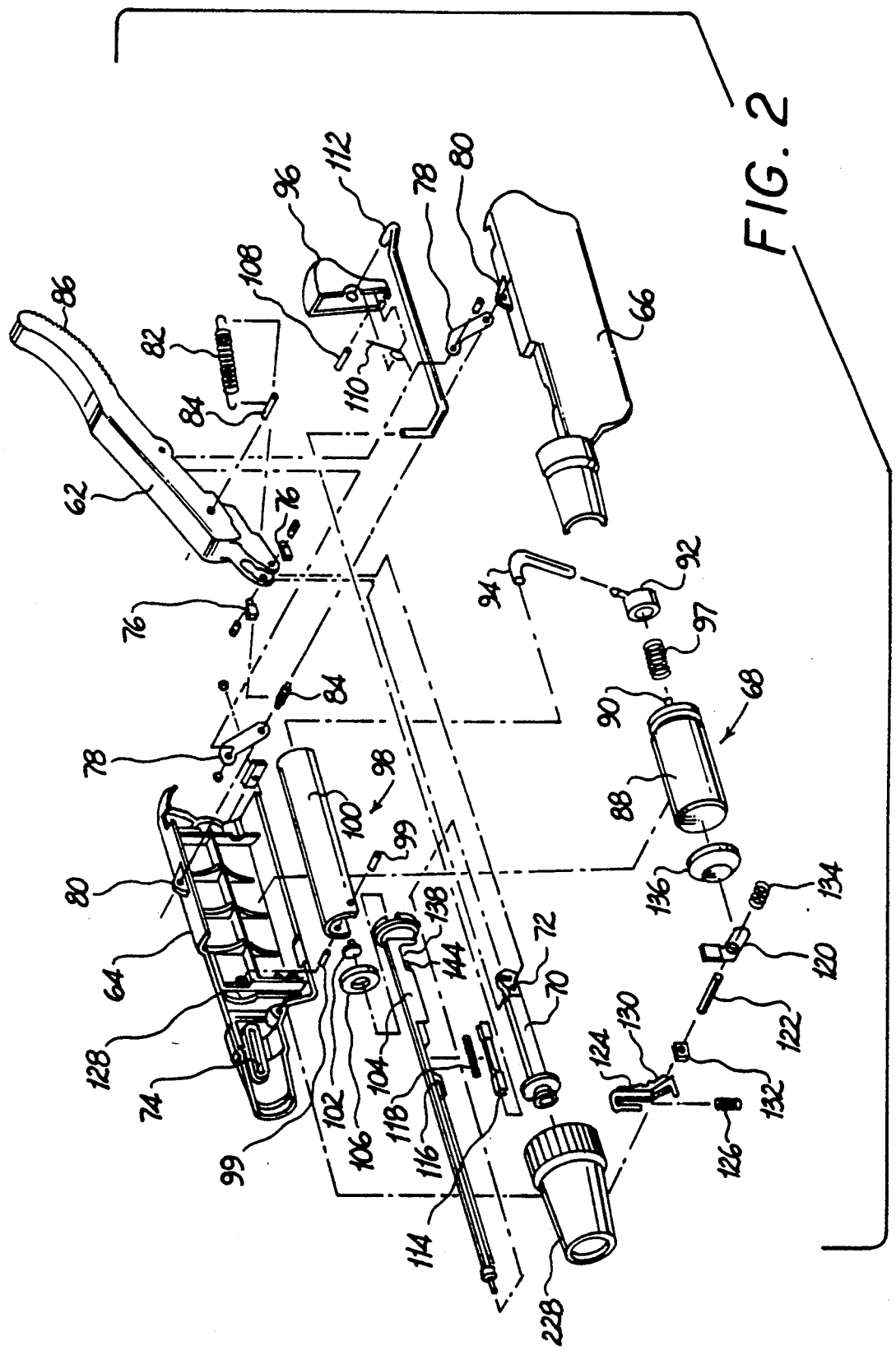
FIG. 2 is an exploded perspective view of the frame and pneumatic assembly of the surgical instrument of FIG. 1.

Turning now to FIG. 2, the frame portion 52 of surgical apparatus 50 includes opposed first and second housing members 64 and 66 which enclose a pneumatic system designated generally by reference numeral 68. The distal end portion of articulating handle member 62 is pivotally connected to a clamp tube 70 at a pivot point 72. Longitudinal grooves 74 are formed in the opposed first and second housing members 64 and 66 adjacent pivot point 72 for slidably receiving molded shuttles 76 which are attached to the articulating handle member 62 at pivot point 72. The molded shuttles 76 are pivotally connected to either side of the pivot point 72 on the distal end of handle 62 and function to guide the distal end thereof in a longitudinally distal direction as handle 62 is articulated.

A pair of articulating links 78 interconnect an intermediate portion of handle member 62 to a pair of projections 80 formed on an upper surface of housing members 64 and 66 respectively. A handle return spring 82 extends between handle 62 and housing members 64 and 66 by means of a pair of spring anchor pins 84, one of which is disposed in handle 62 and the other extending between projections 80. Anchor pins 84 also serve to pivotally connect articulating links 78 to projections 80. This spring 82 assists in returning handle 62 from its closed position to its open position.

The proximal end of articulating handle 62 is preferably diagonally formed away from housing members 64 and 66 so as to enable the surgeon to more easily release the handle 62 from its closed position. This is done by placing the hand under the proximal end of handle 62 and lifting. A texturized or serrated portion 86 may be advantageously formed on an under surface of the proximal end of handle 62 to enhance the gripping thereof.

Figure 11:
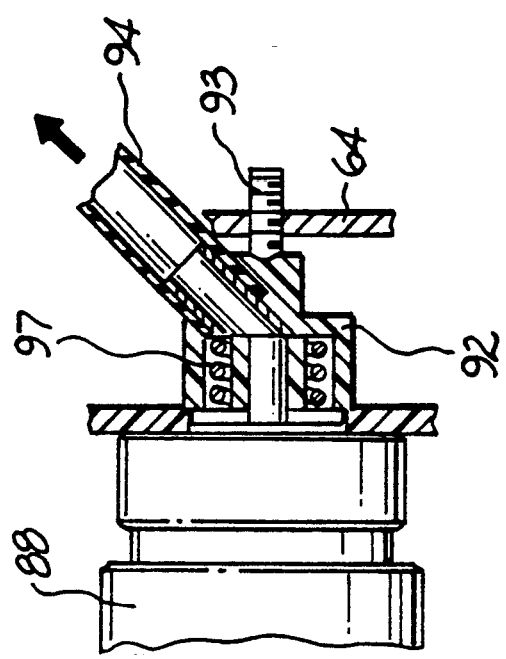
FIG. 11 is a side cut away view in cross section taken along line 11—11 of FIG. 10 showing the valve and gas tube of the pneumatic assembly.
Figure 8:
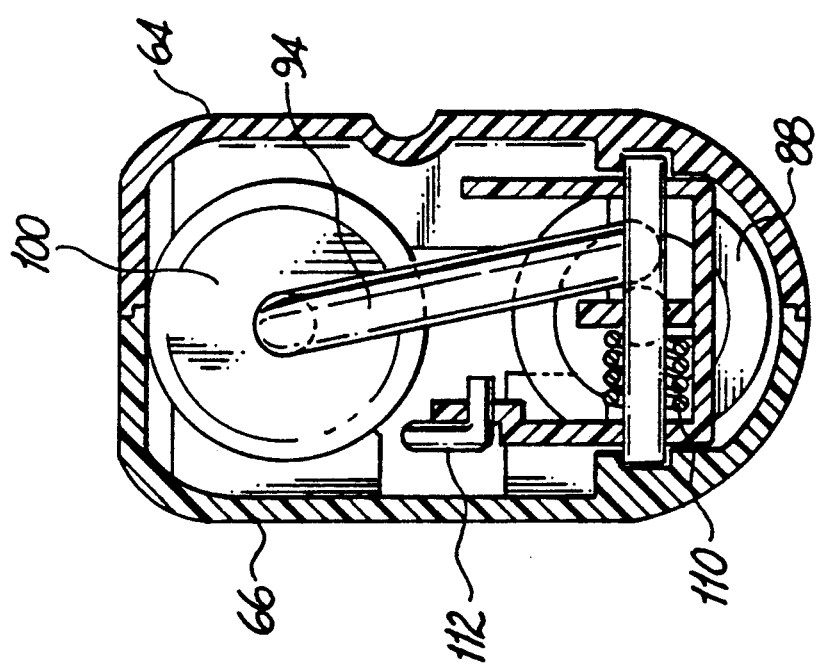
FIG. 8 is a transverse view in cross section taken along line 8—8 of FIG. 3 oriented toward the distal end of the instrument showing a portion of the frame and pneumatic assembly.
Figure 9:
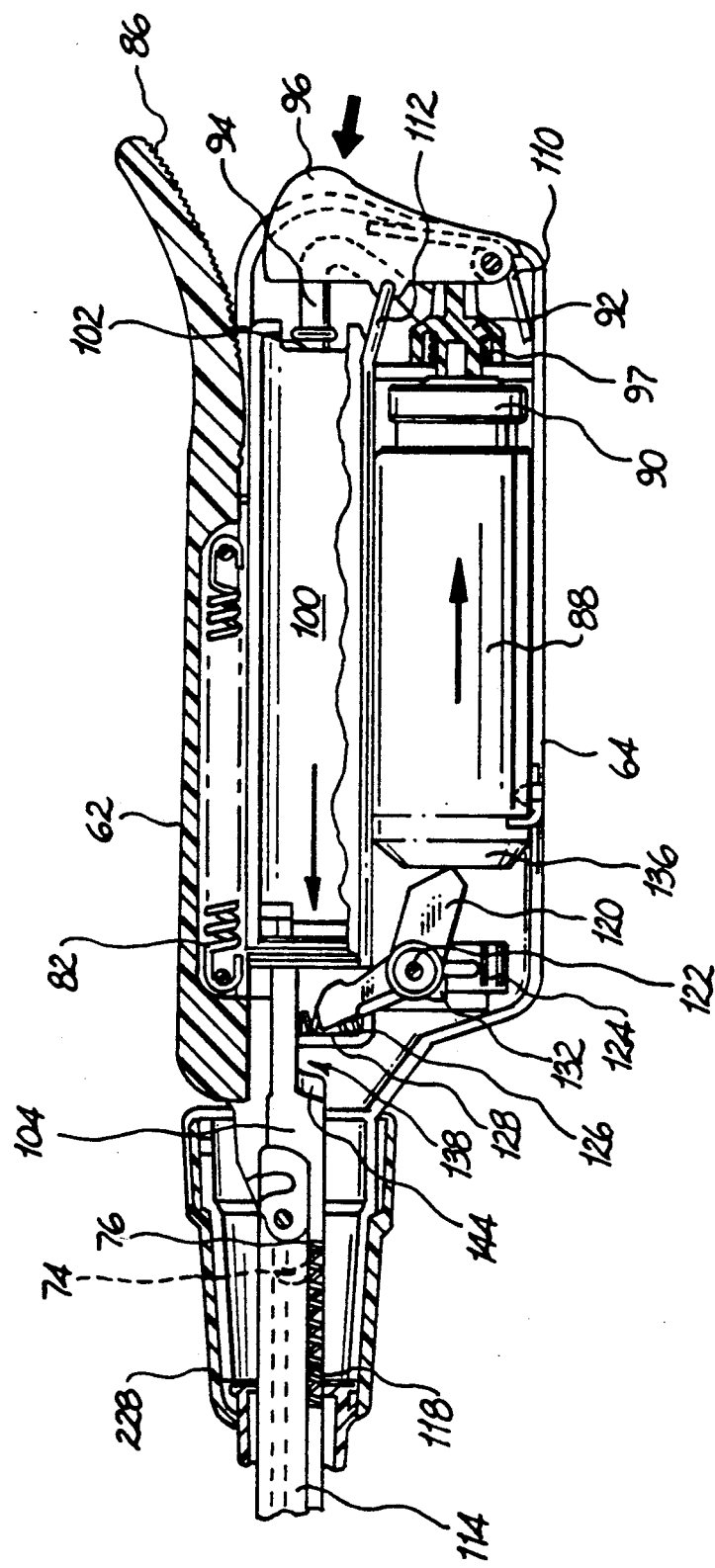
FIG. 9 is a side plan view in cross section showing the frame and pneumatic assembly of the present invention in the clamped and fired position.

Pneumatic system 68 is wholly contained within housing members 64 and 66 and includes a container 88 of relatively low pressure gas longitudinally slidably mounted therein. The pressure of the gas in container 88 during operation of the stapler is typically less than about 200 p.s.i.g. and preferably in the range from about 80 p.s.i.g. to about 160 p.s.i.g. Any suitable non-toxic gas can be used including but not limited to halogenated hydrocarbons which are gaseous at room temperature, e.g., fluorinated hydrocarbons such as Freon 12 or chlorinated hydrocarbons such as Freon 152A. Container 88 dispenses the relatively low pressure gas through stem 90, valve 92, and gas tube 94 when the firing trigger 96 is depressed. Spring 97 is positioned between container 88 and valve 92 and functions to hold the container 88 in a position spaced from valve 92. Valve 92 is fixed within housing members 64 and 66 and is longitudinally adjustable by means of set screw 93 (see FIG. 11). This feature permits the position of valve 92 to be longitudinally changed to compensate for manufactures' variations in length among containers 88 between a distal end and the proximal end of stem 90. A pneumatic actuator 98 is disposed above container 88 within housing members 64 and 66. Actuator 98 includes a pneumatic cylinder 100 which is held in place by opposed pins 99. Cylinder 100 is substantially closed at the proximal end thereof but for a ferrule 102 extending therethrough and is open at its distal end, wherein a pneumatic piston 104 is mounted for reciprocal motion therein on an axis which is parallel to the longitudinal axis of elongated portion 54. Cylinder 100 is preferably circular in transverse cross-section, however, other configurations would function acceptably well.

Piston 104 is pneumatically sealed to cylinder 100 by an O-ring 106 molded of polyethylene or the like. Gas dispensed from container 88 is supplied to pneumatic actuator 98 via gas tube 94 which admits the gas to cylinder 100 through ferrule 102 behind piston 104 to drive piston 104 distally in the cylinder 100. The distal end of piston 104 is adapted to engage the firing mechanism of the surgical apparatus as will be described in greater detail below.

Referring to FIGS. 2-10, firing trigger 96 is pivotally mounted in a proximal end of housing members 64 and 66 by a pivot pin 108. A spring 110 is positioned adjacent pin 108 which serves to bias firing trigger 96 proximally into the prefiring position. A trigger rod 112 extends distally from firing trigger 96 in a longitudinal direction so as to engage a piston slide 114 which is positioned in a lower portion of piston 104. Piston slide 114 comprises a substantially U-shaped channel which fits into a corresponding groove 116 formed in piston 104. Piston slide 114 is spring loaded in a proximal direction by a spring 118 and includes a transverse projection 120 on a lower distal end thereof which engages the distal end of trigger rod 112.

Figure 3:
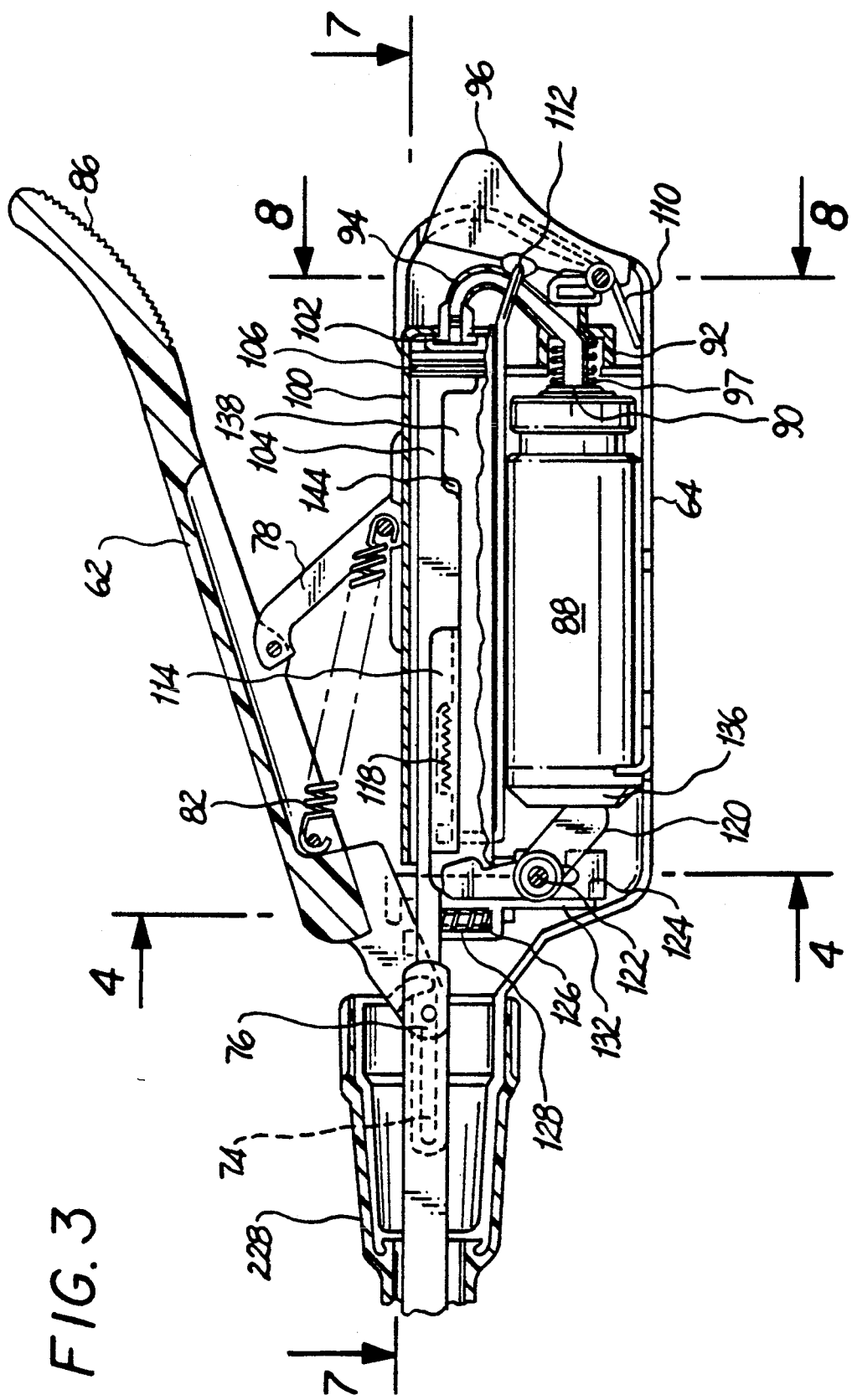
FIG. 3 is a side plan view in cross section taken along line 3—3 of FIG. 1 showing the frame and pneumatic assembly in the unclamped and unfired position.
Figure 4:
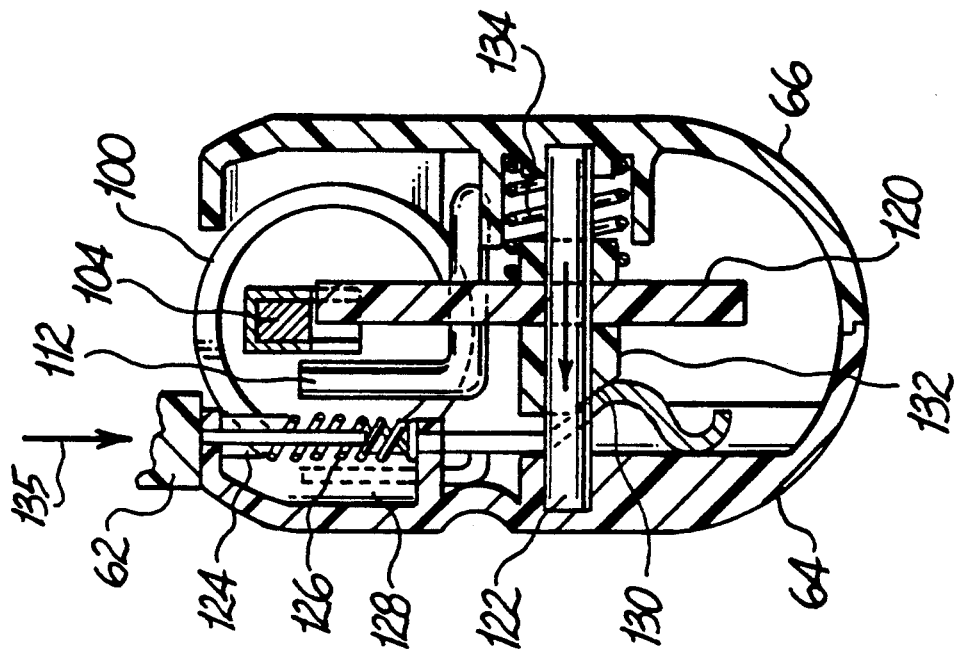
FIG. 4 is a transverse view in cross section taken along line 4—4 of FIG. 3 oriented toward the proximal end of the instrument showing the frame and pneumatic assembly in the unclamped position.
Figure 6:
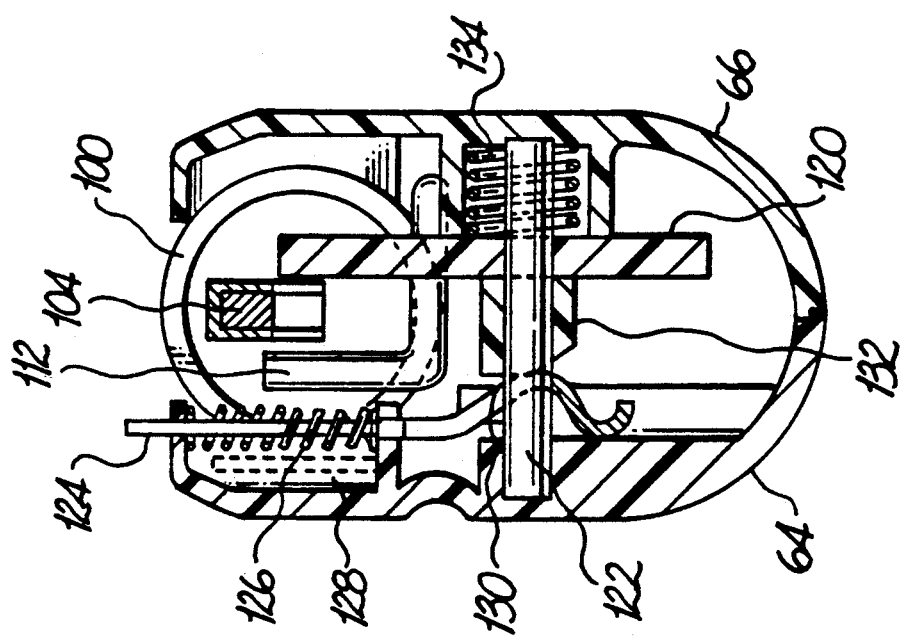
FIG. 6 is a transverse view in cross section taken along line 6—6 of FIG. 5 oriented toward the proximal end of the instrument showing the frame and pneumatic assembly in the clamped and unfired position.

A rocking lever 120 is pivotally mounted on a transverse slide pin 122 and is adapted for transverse movement relative to slide pin 122 between an engaged position prior to firing (see FIGS. 5-7) and a disengaged position when articulating handle 62 is open (see FIGS. 3 and 4). A cam slide 124 is vertically mounted in first housing member 64 for reciprocal movement between an upper position and lower position (see FIGS. 4 and 6, respectively). Cam slide 124 functions to move rocking lever 120 between the engaged position (FIG. 6) and the disengaged position (FIG. 4). Thus, until articulating handle member 62 is closed, causing cam slide 124 to move rocking lever 120 into the engaged position, surgical instrument 50 cannot be fired.

Cam slide 124 is normally biased in its upper disengaged position by a cam slide spring 126 which is mounted in vertical groove 128 formed in the first housing member 64 (see FIGS. 3 and 4). In this upper position, cam slide 124 extends upward beyond first housing member 64 to engage articulating handle member 62 as it is moved to a closed position (see FIGS. 5 and 6). Cam slide 124 further includes a camming surface 130 which contacts a corresponding camming surface of a camming block 132 which is mounted on slide pin 122. Camming block 132 is loaded against cam slide 124 by a slide spring 134 and moves rocking lever 120 transversely on slide pin 122 between an engaged position and a disengaged position. As articulating handle 62 is compressed toward housing members 64 and 66 in the direction of arrow 135 it contacts cam slide 124, moving it downward, and causing camming surface 130 to move camming block 132 and rocking lever 120 transversely into an engaged position in alignment with piston 104.

Turning to FIGS. 3, 5-7 and 9, once the articulating handle 62 has been fully compressed, rocking lever 120 is disposed in alignment with piston slide 114 and can be pivotally moved about transverse slide pin 122 to engage a pusher disk 136 disposed at the distal end of container 88. When the instrument is in the clamped configuration, depression of firing trigger 96 moves trigger rod 112 distally in the longitudinal direction causing piston slide 144 to engage and pivot rocking lever 120 which, in turn, engages pusher disk 136 and moves container 88 into contact with valve 92 to dispense gas and propel piston 104 in the distal direction (see FIGS. 9-11).

As piston 104 moves distally, rocking lever 120 remains in its pivoted firing position by contact with the bottom surface of piston 104. A gap 138 is formed in the bottom surface of piston 104 adjacent the proximal end thereof which effectively allows rocking lever 120 to disengage from piston 104 and return to a position wherein container 88 is released from engagement with valve 92, thereby stopping the flow of gas into pneumatic cylinder 100.

A pair of return springs 140 and 142 disposed in elongated portion 54 drive piston 104 back to its initial prefired position. A camming surface 144 is formed in a distal end of gap 138 which causes rocking lever 120 to move out of engagement with piston 104 as it returns and rocking lever 120 moves to its original prefired position (see FIG. 5).

Figure 12:
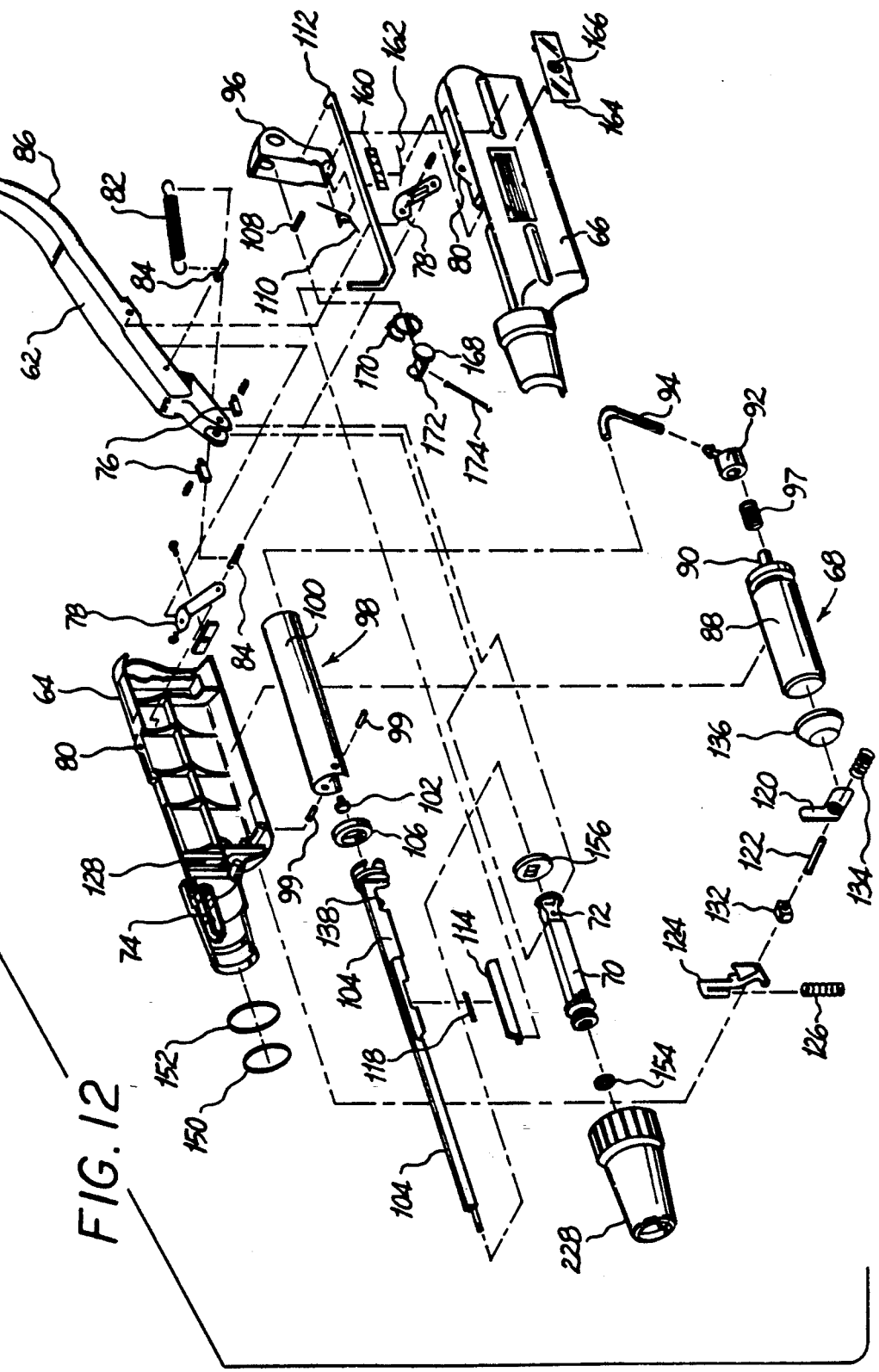
FIG. 12 is an exploded perspective view of another embodiment of the handle portion in accordance with the apparatus of FIG. 1.

Referring to FIG. 12, another embodiment of frame portion 52 is illustrated which includes annular rings 150 and 152 both of which are provided between the distal end of frame 52 and the proximal end of elongated portion 54. In addition to the reduction in egress of insufflation gas resulting from the close tolerances and interfitting of structural elements within frame portion 52 and/or elongated portion 54, these rings 150, 152 further inhibit the escape of insufflation gas from the operative site. Additionally, rings 154 and 156 are positioned adjacent the proximal and distal ends, respectively, of clamp tube 70 to effectively seal off insufflation gas from the area of piston 104.

This embodiment of frame portion 52 further comprises a counter mechanism including a counter ratchet 160 attached to trigger rod 112, and a leaf spring 162 which is mounted in housing 66 so as to engage teeth formed on the bottom surface of counter ratchet 160. Numerical indicators are disposed in longitudinal spaced apart relationship on an outer surface of the counter ratchet 160 and correspond to the number of times apparatus 50 has been fired. An access plate 164 having a viewing window 166 therein is positioned in the outside surface of housing member 66 to facilitate observation of the counter mechanism.

In operation, each time the instrument is fired the leaf spring 162 engages a respective proximally located tooth of the counter ratchet 160, effectively sliding the counter ratchet 160 distally to align the next lower number in viewing window 166. The counter mechanism of this embodiment further includes a locking feature whereby the trigger button 96 is retained in the fired position when the leaf spring 162 engages the most proximal surface of the counter ratchet 160 and prevents the firing rod 112 from returning to its proximal unfired position.

This embodiment of frame portion 52 further includes an integral trigger button rotary safety mechanism comprising a rotary safety shaft 168 disposed within a roller 170. The rotary safety mechanism is rotatably positioned in trigger button 96 with the roller 170 extending out beyond the plane of the back surface of trigger button 96. Projections 172 are eccentrically formed on both sides of rotary safety shaft 168 and extend out beyond the plane of the side surfaces of the trigger button 96. A spring 174 functions to bias the rotary safety mechanism such that projections 172 are disposed in their distalmost orientation.

Figure 13:
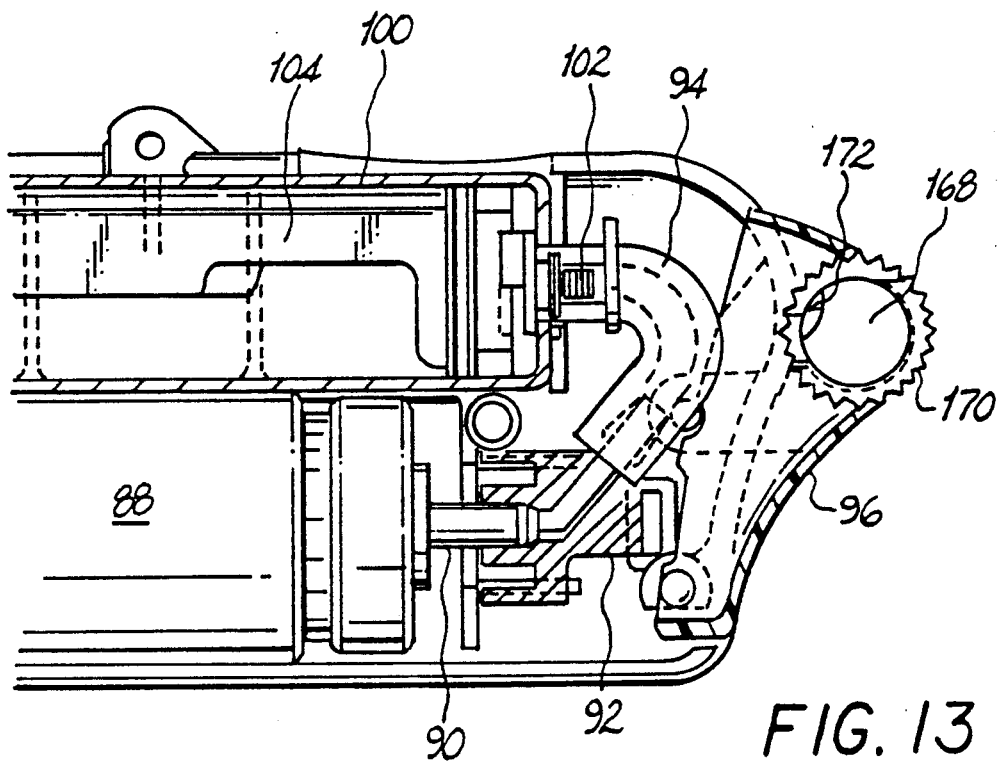
FIGS. 13 and 14 are side cross-sectional views of the firing trigger with integrated lockout structure in the unfired and fired positions respectively.
Figure 14:
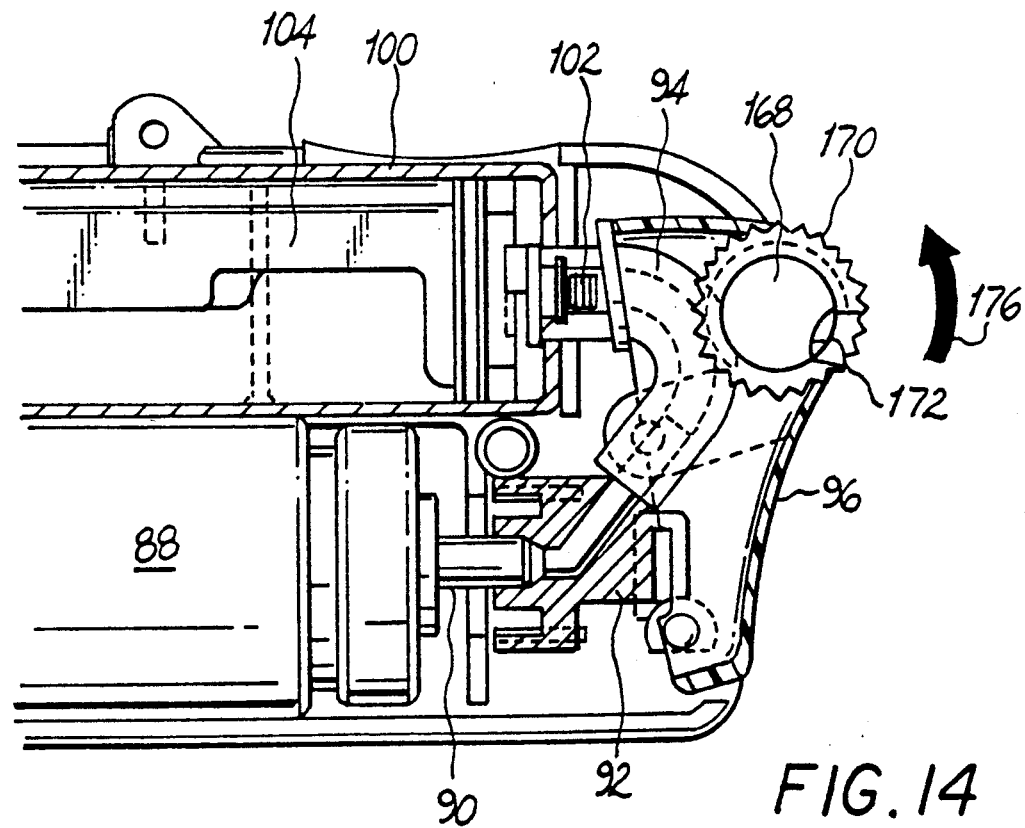

Referring now to FIGS. 13 and 14, in the instrument's unfired position projections 172 are in their distalmost position and are disposed in direct alignment with the proximal ends of the housing members 64 and 66. In this position, trigger button 96 cannot be accidentally depressed to fire the instrument. In order to disengage the safety mechanism, the roller 170 is moved in the direction of arrow 176 so as to rotate projections 172 from their distalmost position to their proximalmost position effectively allowing trigger button 96 to be depressed to fire the instrument. As soon as roller 170 is released, spring 174 returns the safety mechanism to its normal position so as to prevent subsequent accidental firings.

Figure 15:
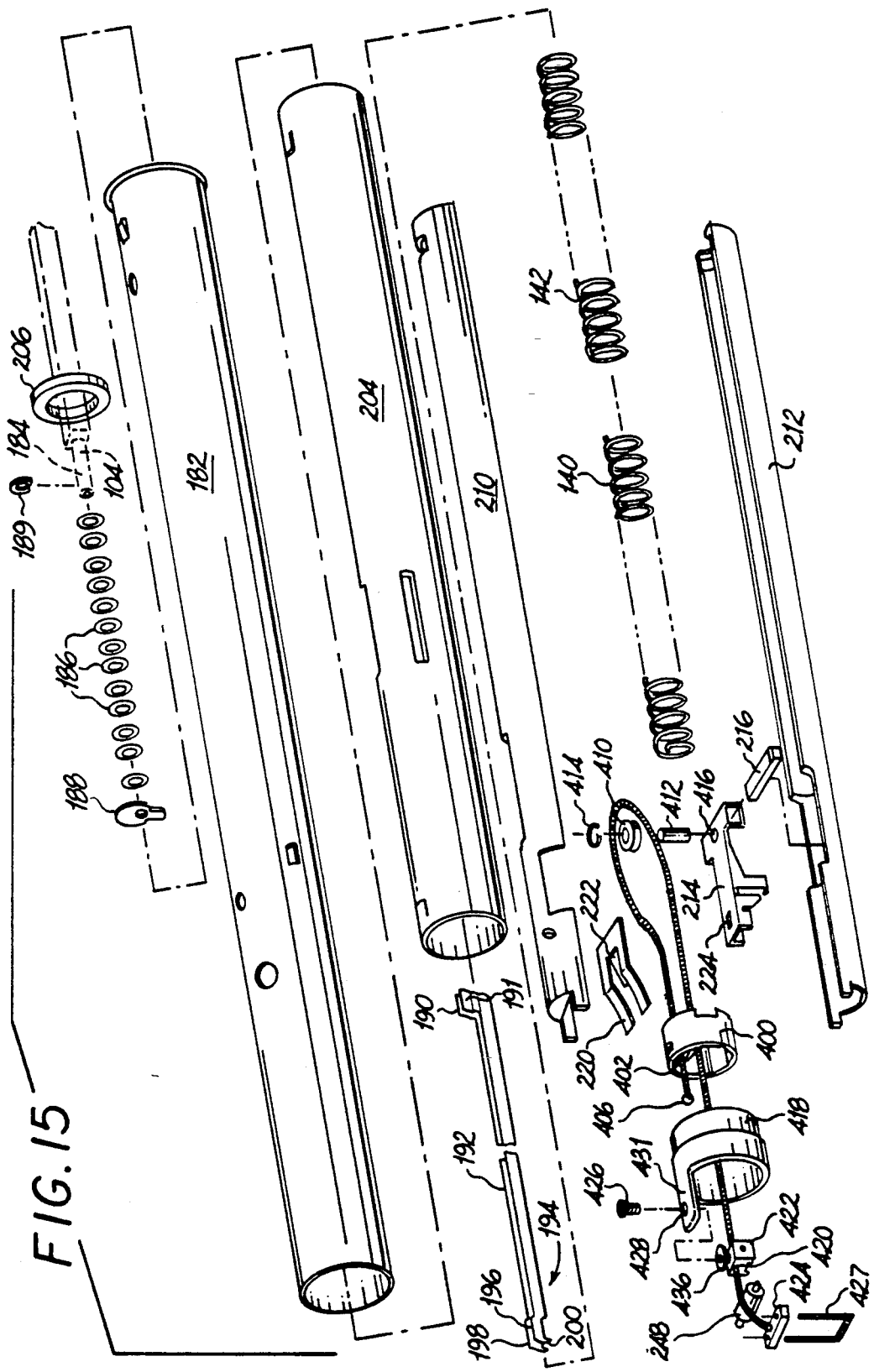
FIG. 15 is an exploded perspective view of the elongated portion of the surgical instrument of FIG. 1.

Turning to FIG. 15, the elongated portion 54 of surgical apparatus 50 is illustrated in exploded detail. At a proximal end of elongated portion 54, piston 104 extends through clamp tube 70 (FIG. 12) and into the proximal end of a cover tube 182. Piston 104 is adapted for reciprocal movement within clamp tube 70 in response to actuation of pneumatic system 68. The distal end of piston 104 is provided with an attachment flange 184 for mounting a plurality of pusher washers 186 of the type which are well suited for high loads in small spaces. A spring support washer 188 is positioned on flange 184 for engaging the proximal ends of inner and outer return springs 140 and 142. A lock washer 189 maintains the pusher washers 186 in a desired position on flange 184. Attachment flange 184 has a chamfered distal tip and is configured and dimensioned to be received between the proximal opposed fingers 190 and 191 of a channel member 192.

As shown in FIG. 15, channel member 192 is defined by an elongated structure which is slidably mounted in elongated portion 54 for reciprocal longitudinal motion therein. As mentioned above, channel 192 has opposed fingers 190 and 191 at a proximal end thereof to receive attachment flange 184 of piston 104. A forked portion 194 is provided at a distal end portion of channel 192 defining a slot 196 therebetween. Forked portion 194 has a pair of opposed ramping surfaces 198 and 200, the function of which will be described in greater detail below.

An extension sleeve 204 is disposed within cover tube 182 and is fixed on a proximal end thereof to clamp tube 70. A sealing member 206 is mounted adjacent clamp tube 70 for sealably isolating frame portion 52 of instrument 50 from elongated portion 54 thereof. Inner and outer return springs, 142 and 140 respectively, are contained within upper extension spacer 210 and lower extension spacer 212 which are, in turn, combined and fixed within the extension sleeve 204. Spring support washer 188 abuts the proximal ends of inner and outer return springs 142 and 140 and, when instrument 50 is fired, transmits the energy of the compressed springs 142 and 140 to the piston 104, returning it to its prefired position.

A support structure 214 is also disposed within extension spacers 210 and 212 adjacent the distal end thereof which functions to releasably receive cartridge assemblies in instrument 50. Support structure 214 is retained in place within combined extension spacers 210, 212 by a transverse support key 216. A clamp lockout structure is incorporated into support structure 214 and upper extension spacer 210. The clamp lockout structure comprises a leaf spring 220 having a diagonally downwardly extending projection 222 attached thereto. A slot 224 is formed through the top surface of support structure 214 and is adapted to engage and receive projection 222 whenever the support structure is not longitudinally aligned. This clamp lockout structure is designed and configured to prevent the instrument jaws from closing on tissue unless the cartridge and/or jaw elements are properly emplaced within the elongated portion 54 of apparatus 50.

Figure 16:
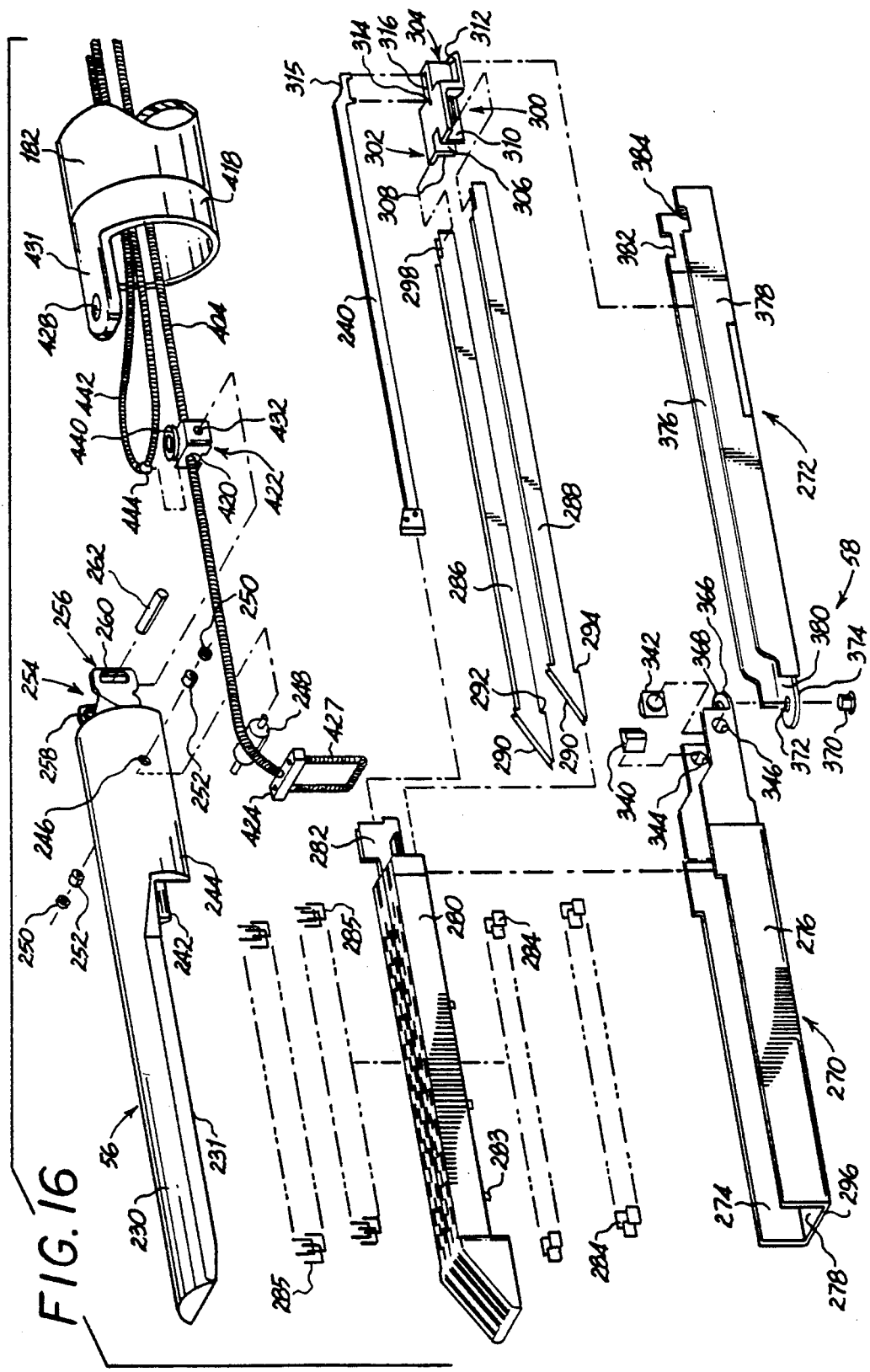
FIG. 16 is an exploded perspective view of the articulating cartridge assembly of the surgical instrument of FIG. 1.
Figures 17, 18, 19:
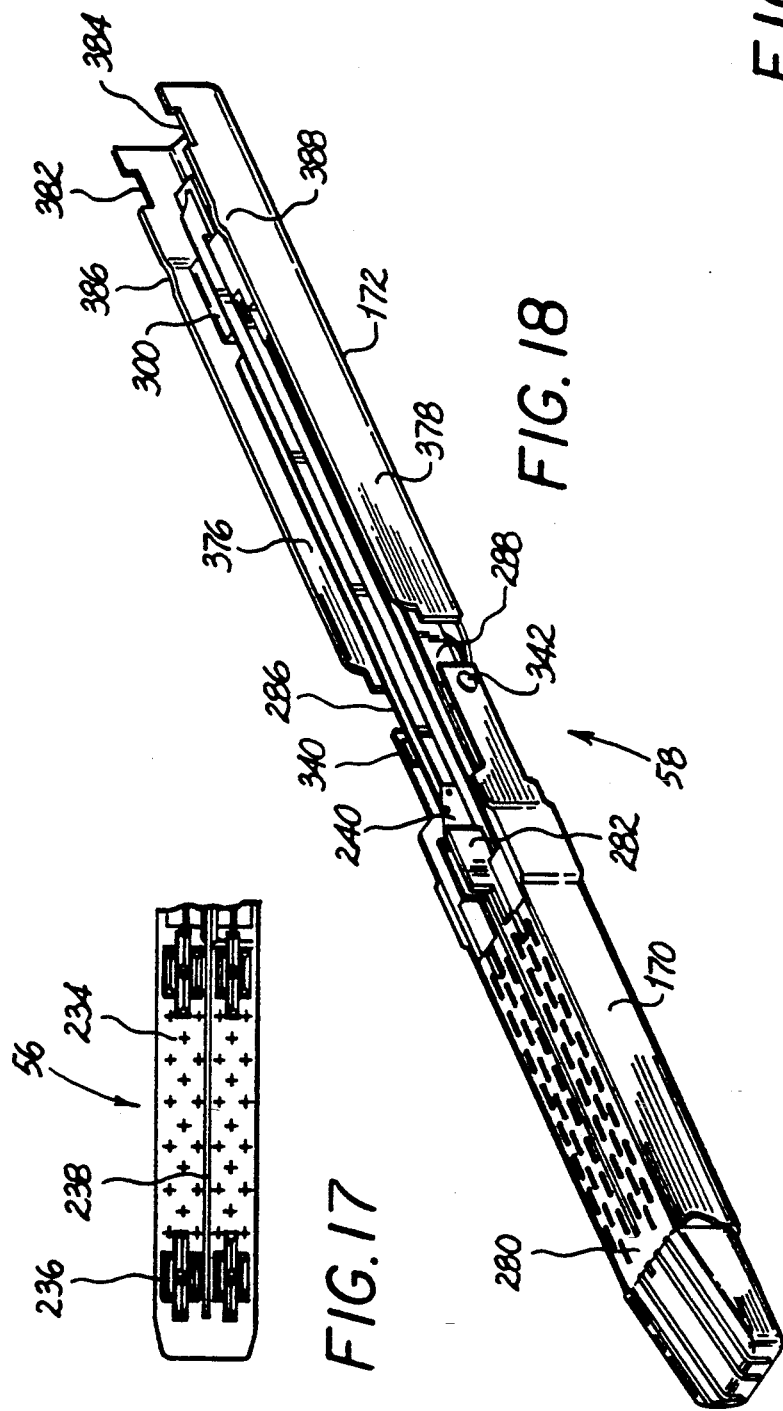
FIG. 17 is a bottom plan view of the anvil member of the articulating cartridge assembly of FIG. 16.
FIG. 18 is a perspective view of the articulating cartridge assembly of the surgical instrument of FIG. 1.
FIG. 19 is a top plan view of the articulating cartridge assembly of FIG. 18 with the cartridge element removed therefrom.

Referring now to FIG. 16 and 17, anvil member 56 of surgical apparatus 50 comprises an elongated distal body portion 230 and a proximal mounting shroud 232. Body portion 230 defines a staple forming plate 234 (see FIG. 17) having a plurality of staple forming depressions 236 provided therein into which staples are driven so as to be formed. A longitudinal center groove 238 is also provided in staple forming plate 234 to facilitate the guided passage of a surgical knife 240 during a firing sequence of apparatus 50. Mounting shroud portion 232 is defined by opposed side walls 242 and 244 which are dimensioned to fit cooperatively upon a portion of cartridge assembly 58. Apertures 246 are included in the opposed side walls 242 and 244 for mounting a cylindrical pulley 248. Pulley 248 is maintained within shroud portion 232 by opposed fastener ring pairs 250 and 252 and functions in cooperation with a mechanism for moving anvil member 56 between an open position and a closed position. A pair of opposed spaced apart arms 254 and 256 extend longitudinally from the proximal end of shroud portion 232 and have vertical mounting slots 258 and 260 provided therein, respectively, for receiving a mounting pin 262. Mounting slots 256 and 258 enable anvil member 56 to adjust its position upon engaging tissue against forming plate 234. More particularly, slots 256 and 258 permit adjustment of the spacing between forming plate 234 and cartridge assembly 58.

The articulating cartridge assembly 58 of the subject invention comprises a forward housing portion 270 and a rearward housing portion 272. Forward housing 270 is defined by a channel structure of substantially rectangular cross-section having opposed side walls 274 and 276 and a bottom wall 278. This channel structure constitutes the cartridge receiving portion and is dimensioned to receive a cartridge 280. A longitudinal groove structure 282 is defined in cartridge 280 for receiving and guiding knife 240 therethrough. A plurality of stems 283 extend downwardly from the undersurface of cartridge 280 for engagement in a plurality of corresponding apertures 287 formed in the bottom wall 278 of forward housing 270. A plurality of pusher elements 284 are disposed in cartridge 280 in abutment with a plurality of corresponding staples 285. The staples 285 are advantageously arranged in six longitudinal rows with three rows positioned on either side of groove structure 282. See, U.S. Pat. No. 4,978,049 to Green, the disclosure of which is incorporated herein by reference. In addition, two pairs of longitudinal slots are formed in the cartridge housing 280 and are adapted to receive a pair of dual cam bars 286 and 288 therein. Cam bars 286 and 288 each serve to drive three corresponding longitudinal rows of staples 285.

Cam bars 286 and 288 are each provided with a cam surface 290 in an upper distal end thereof and an overhanging ledge 292 with vertical surface 294 in a lower distal end. This overhanging ledge 292 is dimensioned to extend into the longitudinal slots formed in cartridge 280 to a point wherein the vertical surface 294 of overhanging ledge 292 drops down and abuts the forward edge 296 of the forward housing portion 270 cartridge assembly 58 when cam bars 286 and 288 move to their distal fired position. At their proximal ends, cam bars 286 and 288 are provided with hook structure 298 for releasably engaging a cam bar adapter 300.

Referring now to FIGS. 16, 19, and 23, one embodiment of cam bar adapter 300 in accordance with the present invention is illustrated. Cam bar adapter 300 comprises a forward section 302 and a rearward section 304. Forward section 302 is substantially rectangular in configuration and has a central longitudinal groove 306 formed therein and dimensioned to receive the longitudinal groove structure 282 on cartridge 280 when cam bar adapter 300 is urged to its forwardmost position. Flanges 308 and shelves 310 function to removably retain the proximal ends of cam bars 286 and 288. The rearward section 304 of cam bar adapter 300 is rectangular in configuration with projections 312 formed in the proximal end thereof. The rearward section is dimensioned to be receivable within the slot formed in forked portion 194 in channel member 192. Projections 312 are dimensioned to engage ramping surface 198 so as to allow forked portion 194 to ride up and over projections 312 when it is moved in the distal direction. A vertical bore 314 and a longitudinal groove 316 are formed in the rearward section 304 of cam bar adapter 300 which retain and hold the shank portion 315 of knife 240.

Figure 22:
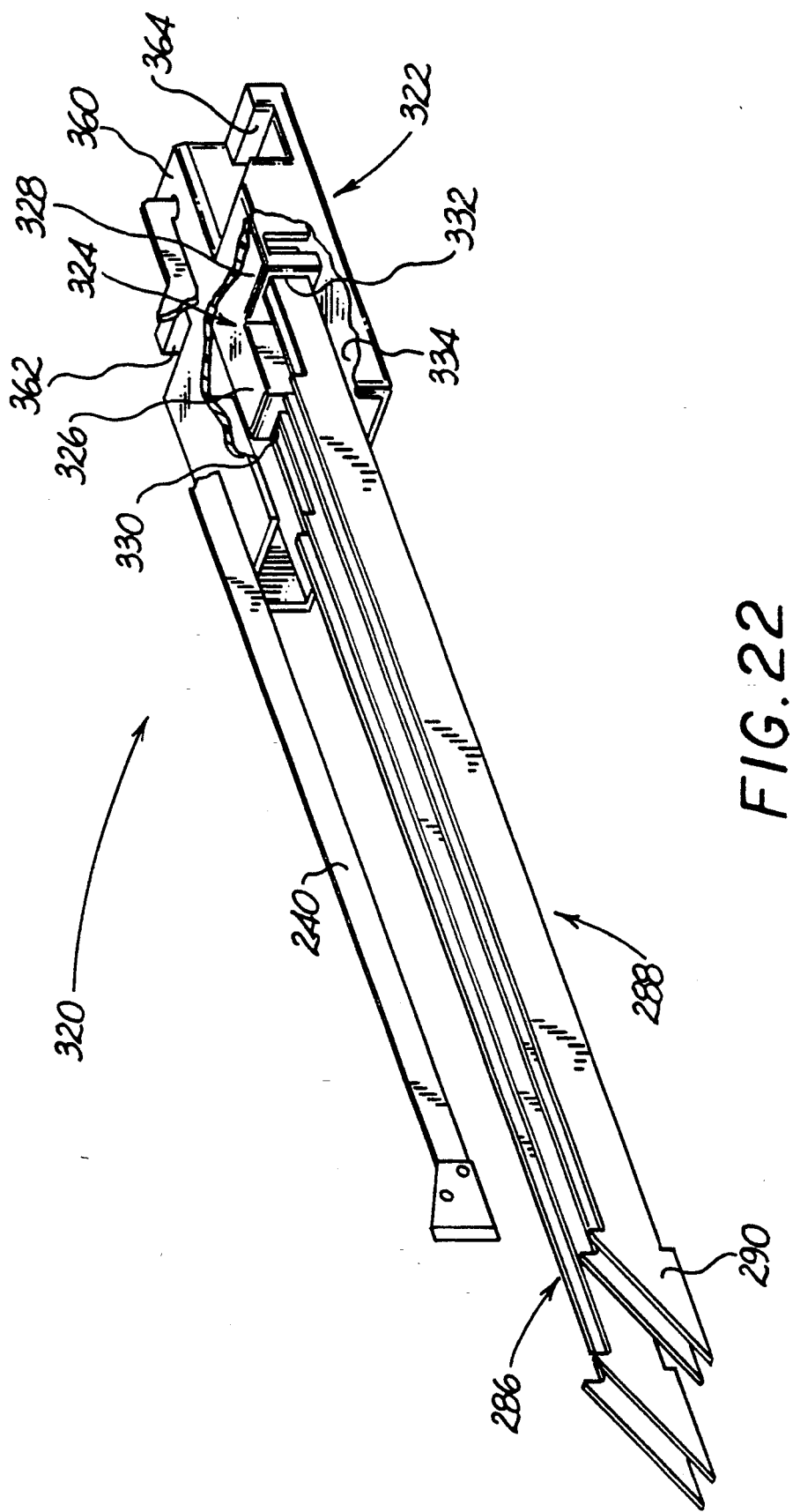
FIG. 22 is an enlarged perspective view, partially cut-away, of the cam bar adapter of FIGS. 20 and 21.

Although cam bar adapter 300 is effective to maintain cam bars 286 and 288 and to transport the same through cartridge assembly 58, it may be desirable to provide a cam bar adapter which enables the proximal ends of cam bars 286 and 288 to move freely in a transverse direction while being effectively maintained in a desired longitudinal position. Free mounting of the cam bars provides several advantages over fixed mounting which advantages will be discussed in detail hereinbelow. FIGS. 20–22 illustrate this embodiment of the cam bar adapter and is designated generally by reference numeral 320. Cam bar adapter 320 comprises a cam bar support fixture 322 and a housing structure 324. Support fixture 322 is defined by a substantially L-shaped structure having an elongated leg portion 326 and a transverse leg portion 328. A slot 330 is provided in leg portion 326 for receiving the proximal end of dual cam bar 286 and a similar slot 322 is provided in leg portion 328 for receiving the proximal end of dual cam bar 288. The staggered mounting of cam bars 286 and 288 in L-shaped support structure 322 advantageously positions cam bars 286 and 288 to more effectively eject the staples from cartridge 285. Support fixture 322 is dimensioned so as to fit within a rectangular channel 334 defined within housing structure 324. Channel 334 accommodates support fixture 302 in such a manner so that it can move freely therein.

The advantages of freely mounting cam bars 286 and 288 are best explained with reference to FIGS. 23 and 24. Cam bar adapter 300 is illustrated in FIG. 24, wherein the respective proximal portions of cam bars 286 and 288 are fixedly mounted. Upon articulating the forward housing 270 of cartridge assembly 58, cam bars 286 and 288 are compressed by opposed bearing members 340 and 342 disposed in forward housing 270. The compression of the cam bars 286 and 288 causes a buckling effect at the central spans thereof. The deflection is accentuated because the proximal end portions of cam bars 286 and 288 are fixed in cam bar adapter 300. In contrast, if cam bars 286 and 288 are mounted in cam bar adapter 320 such that the respective proximal end portions thereof are maintained in the L-shaped support fixture 322 which moves freely within channel 334 defined in housing structure 324, the degree of deflection or buckling across the central spans of cam bars 286 and 288 is substantially decreased. By reducing the degree of deflection across the spans of cam bars 286 and 288, the amount of force needed to drive cam bars 286 and 288 is also decreased. Moreover, the amount of pressure required to be released by the pneumatic system for driving cam bars 286 and 288 through a complete stroke will be less when the respective proximal end portions of cam bars 286 and 288 are mounted freely rather than fixedly in a cam bar adapter.

The cam bars are often made of stainless steel, however, it has been found that forming the cam bars from a shape memory alloy comprising, for example, a composition of nickel and titanium (such a composition is available from Raychem Corp., Menlo Park, Calif. under the trade name TINEL), rather than stainless steel, will reduce the amount of force required to drive cam bars 286 and 288 through a firing sequence.

Referring to FIGS. 18, 19, 23, and 24, bearings 340 and 342 are mounted in a pair of opposed ports 344 and 346 provided in the opposed side walls 274 and 276 respectively, adjacent the proximal end of forward housing 270. Bearing members 340 and 342 have a truncated triangular configuration defining a planar bearing surface for guiding cam bars 286 and 288 as they traverse cartridge assembly 58 at such times when it is in an articulated position and, in addition, compress the cam bars as they travel into cartridge 280 as discussed above.

Referring again to FIGS. 20–22, housing structure 324 of cam bar adapter 320 is further provided with a pair of spaced apart apertures 350 and 352 for retaining a pair of corresponding prongs 354 and 356 formed on the shank 358 of knife 240. The rearward section 360 of housing structure 324 is of rectangular configuration and defines a structure for engaging groove 196 in channel member 192. Seats 362 and 364 are provided on either side of rearward section 360 for engaging the forked portion 194 of channel member 192.

Referring again to FIGS. 16, 18 and 19, a flange 366 extends outwardly from the proximal end of the bottom wall 278 of forward housing 270 and includes an aperture 368 for receiving a rivet 370. Rivet 370 also extends through an aperture 372 provide in a flange 374 which extends outwardly from the distal end of rearward housing 272. This rivet connection enables forward housing 270 to articulate relative to rearward housing 272.

Rearward housing 272 is defined by a channel of U-shaped cross-section having opposed side walls 376 and 378 and a bottom wall 380. Locking slots 382 and 384 are formed in the opposed side walls 376 and 378 adjacent the proximal end thereof for engaging and retaining support structure 214 (see FIG. 15). A pair of opposed crimps 386 and 388 are provided in opposed side walls 376 and 378 adjacent locking slots 382 and 384 for establishing a friction fit with cam bar adapter 300 (or in the alternative cam bar adapter 320) within which the dual cam bars 286 and 288 are mounted.

Figure 28:
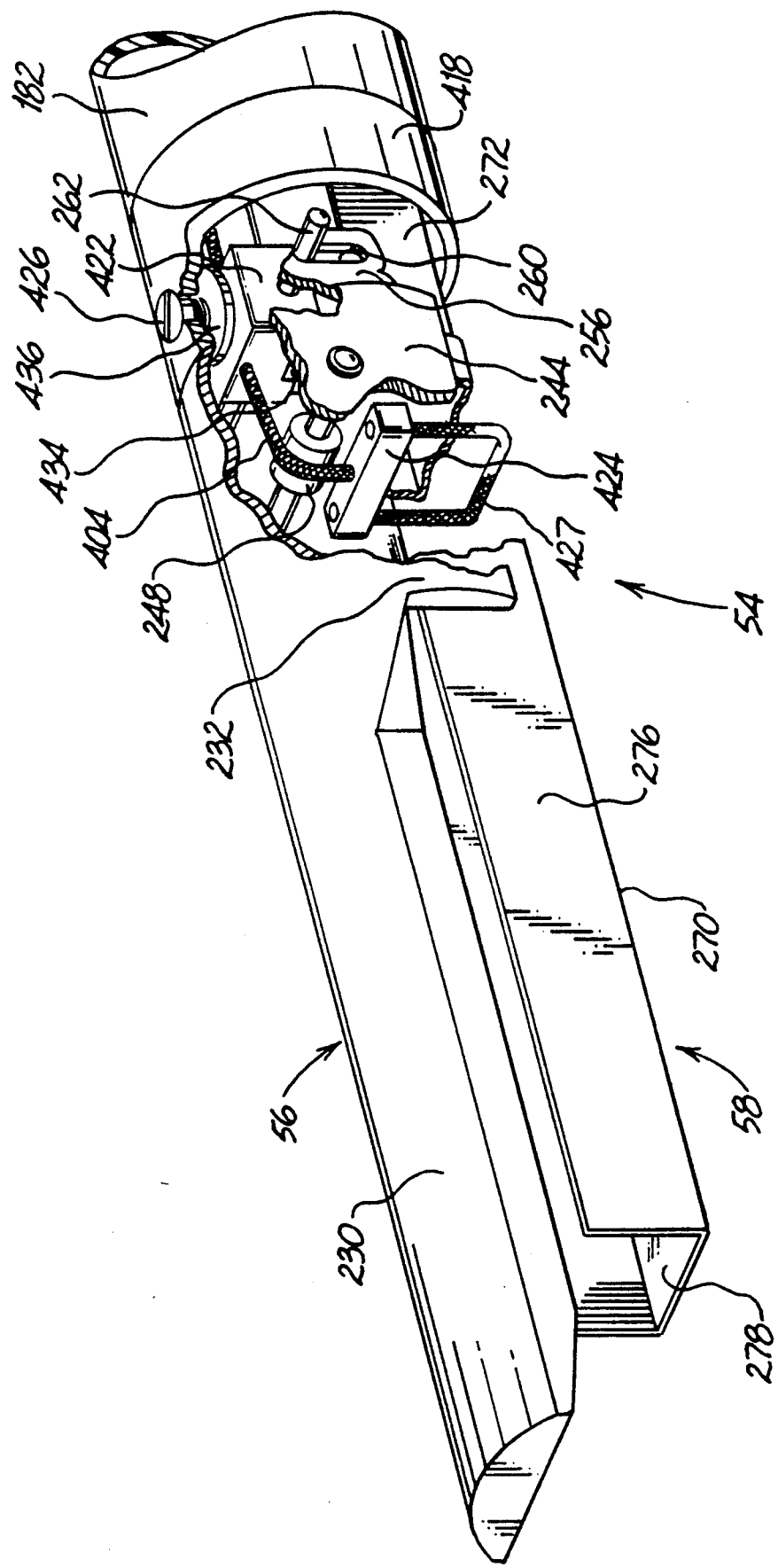
FIG. 28 is an enlarged perspective view, partially cut-away, of the distal end of the elongated portion of the subject invention showing the mechanisms provided therein.

Referring now to FIGS. 15, 16, and 28, the movement of anvil member 56 relative to cartridge assembly 58 in this embodiment is achieved through a linkage and cable system. This system includes a tube collar 400 which mounts on the distal end of combined upper and lower extension spacers 210, 212. Tube collar 400 has an internal partition wall 402 formed therein through which extends an aperture having a diameter which permits the passage of a cable 404 therethrough, while prohibiting the passage of an anchor ball 406 which is fastened to the trailing end of cable 404. As it extends from partition wall 402, the line of action of cable 404 is reversed from a proximal direction to a distal direction by turning about a pulley assembly which includes an annular pulley 410 mounted on a pulley shaft 412, and retained thereon by a locking ring 414. Pulley shaft 412 is supported in an aperture 416 provided adjacent the proximal end of support structure 214. Upon turning about pulley 410, cable 404 extends back through tube collar 400, avoiding partition wall 402 and thereafter extending through a mounting collar 418 positioned on the distal end of outer cover tube 182 of elongated portion 54. Cable 404 then extends through a longitudinal bore hole 420 formed in a pivot block 422. Pivot block 422 is rotatably mounted on a flange 424 extending from mounting collar 418 by a threaded fastener 426 maintained in threaded aperture 425. Threaded fastener 426 extends through an aperture 428 which is provided in flange 424. The function and structure of pivot block 422 will be discussed in greater detail below with respect to the mechanism for articulating cartridge assembly 58. After passing through bore hole 420 in pivot block 422, cable 404 turns about cylindrical pulley 248 which translates the line of action of cable 404 in a direction perpendicular to the longitudinal axis of elongated portion 54. The cable 404 is terminated at the trailing end thereof at an upper face of a cable separation block 424. A U-shaped anchor cable 427 extends from the opposed face of cable separator block 424 and is dimensioned and configured to engage the forward housing 270 of articulating cartridge assembly 58 so as to anchor the cable mechanism. Preferably, a cover tube, which may be formed of aluminum or a like material, clothes anchor cable 427.

The position of cable separator block 424 with respect to cylindrical pulley 248 can vary. For example, cable separator block 424 can be disposed proximal to pulley 248 as illustrated in FIG. 36. In this instance, the cylindrical pulley 248 would be configured with a pair of spaced apart annular grooves or tracks for accommodating the U-shaped anchor cable 427.

During operation of apparatus 50, reciprocating movement of the combined extension spacer 210, 212 in response to articulation of handle member 62 in frame portion 52, will cause corresponding translation of tube collar 400, thereby causing cable 404 to move in a longitudinal direction about annular pulley 410, and subsequently about cylindrical pulley 248 in a perpendicular direction. As the trailing end of cable 404 moves about pulley 248, it exerts a force thereupon which consequently causes anvil member 56 to move relative to the cartridge assembly 58.

Figure 26:
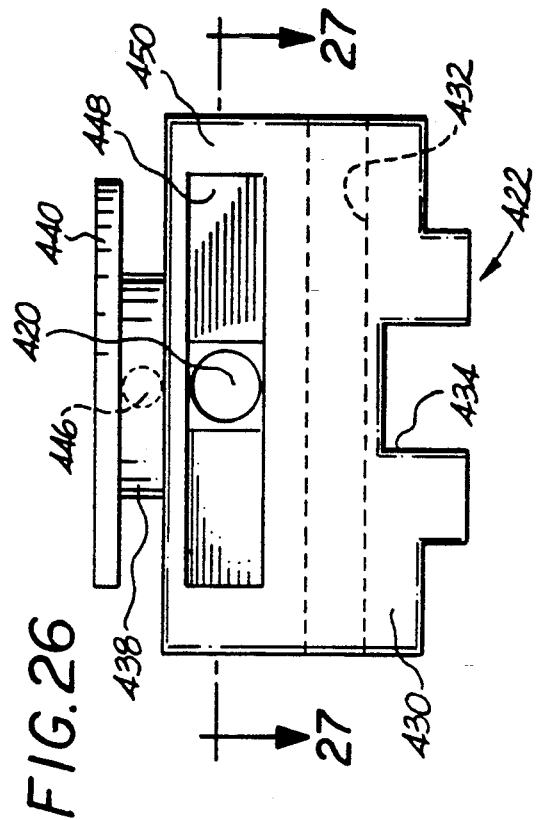
FIG. 26 is a side elevational view of the pivot block of FIG. 25.
Figure 27:
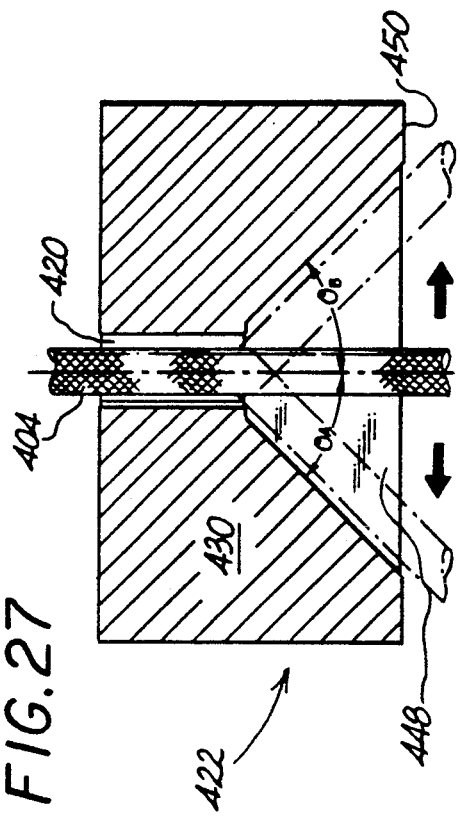
FIG. 27 is a top plan view in cross-section taken along line 27—27 of FIG. 26 showing the configuration of the cable passageway defined therein.
Figure 25:
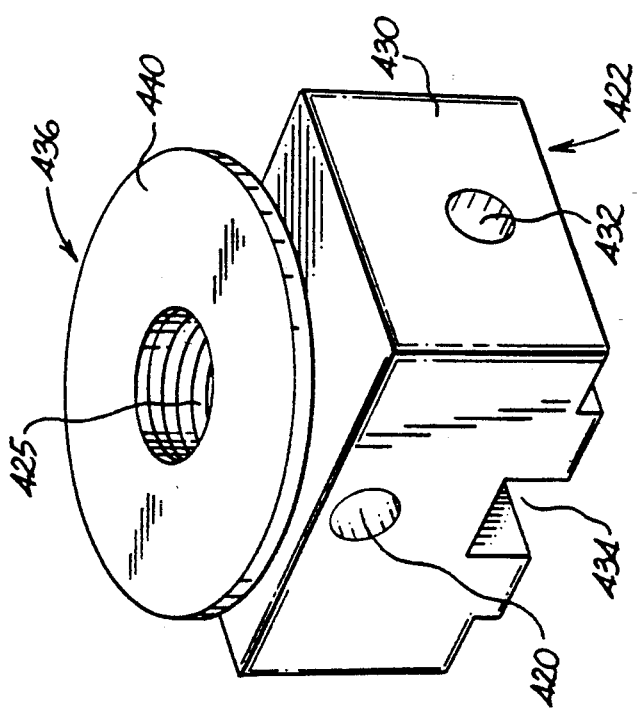
FIG. 25 is an enlarged perspective view of the pivot block illustrated in FIGS. 15 and 16.

Apparatus 50 further comprises a mechanism for effectuating the articulation of the forward housing 270 relative to the rearward housing 272 of cartridge assembly 58. The articulation mechanism includes, as stated previously, pivot block 422. As best seen in FIGS. 25-27, pivot block 422 comprises a substantially rectangular body portion 430 through which extends longitudinal bore hole 420, and a transverse bore hole 432 for receiving pivot pin 262 about which anvil member 56 pivots when the cable and linkage system is employed as described hereinabove. A longitudinal groove 434 is provided in the undersurface of body portion 430 for permitting passage of knife 240 as it traverses cartridge assembly 58 mounted upon cam bar adapter 300. A fixed capstan 436 comprising a shaft portion 438 and a hood portion 440 extends upwardly from the body portion 430 of pivot block 422 about which an articulation cable 442 of looped configuration is supported. More particularly, cable 442 has an anchor ball 444 intermediate its length which is dimensioned and configured to be fixed within a port 446 formed in shaft portion 438 of capstan 436 (see FIG. 26.).

As best seen in FIG. 27, the walls of longitudinal bore hole 420 diverge 45° from the central axis thereof at a central point within body portion 432 so as to define a mouth 448 at the proximal face 450 of pivot block 422. The diverging mouth 448 of longitudinal bore hole 420 enables the relative movement of cable 404 during articulating movement of cartridge assembly 58 within a 90° sector of translation wherein $\theta_A$ and $\theta_B$ are each equal to 45°. It is also envisioned that, where a wider section of translation is desired, pivot block 422 and any associated structural elements of the apparatus may be modified to achieve at least 60° of articulation in either direction relative to the longitudinal axis of the instrument. The section of articulation cable 442 opposite anchor ball 444 is connected to a dial member 452 which is provided in the elongated portion 54 adjacent the proximal end thereof. Rotation of dial member 452 in either the clockwise or counter clockwise direction (see FIGS. 31 and 32, respectively) will cause articulating cable 442 to translate in such a manner so as to cause pivot block 422 to rotate on an axis perpendicular to the longitudinal axis of elongated portion 54 about threaded fastener 426. Consequently, anvil member 56, which is connected to pivot block 422 through pin member 262, and forward housing 270 which is operatively associated with anvil member 56 through U-shaped anchor cable 427, is caused to pivot about rivet member 370.

In use, the elongated portion 54 of instrument 50 is inserted into the body, preferably through an endoscopic tube. It is further preferred that the endoscopic tube apparatus be capable of maintaining a sealed pneumoperitoneum, with the internal sealing member of the housing further maintaining this seal despite introduction of the instrument in accordance with the invention into the endoscopic tube. As a practical matter, the jaws of the instrument are closed for insertion into the endoscopic tube, either by pinching the anvil and cartridge prior to insertion or by closing the articulating handle to cam the jaws closed prior to insertion.

Figure 29:
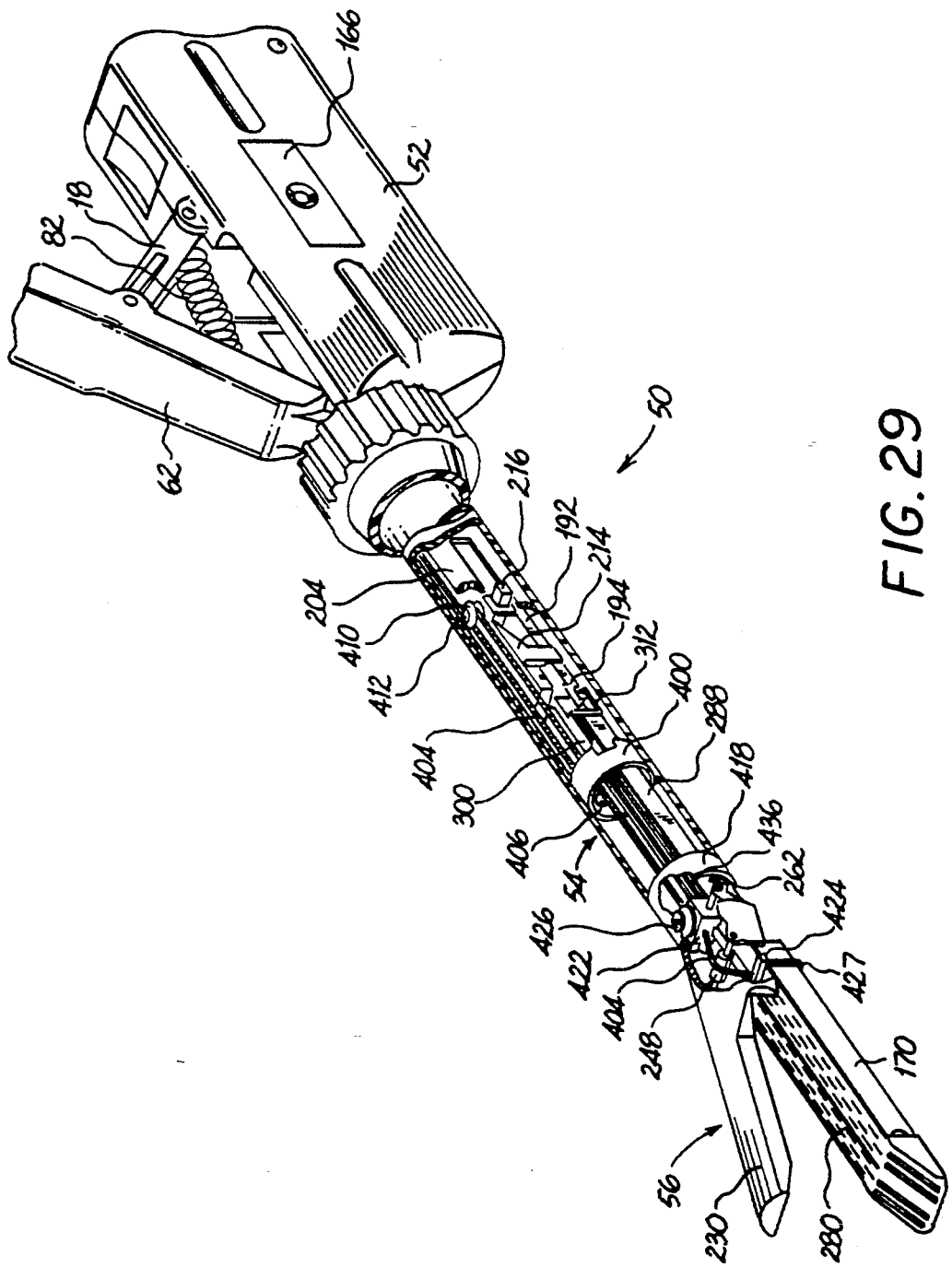
FIG. 29 is a perspective view, partially cut-away, of the surgical instrument of FIG. 1 with the anvil member in an opened position.
Figure 30:
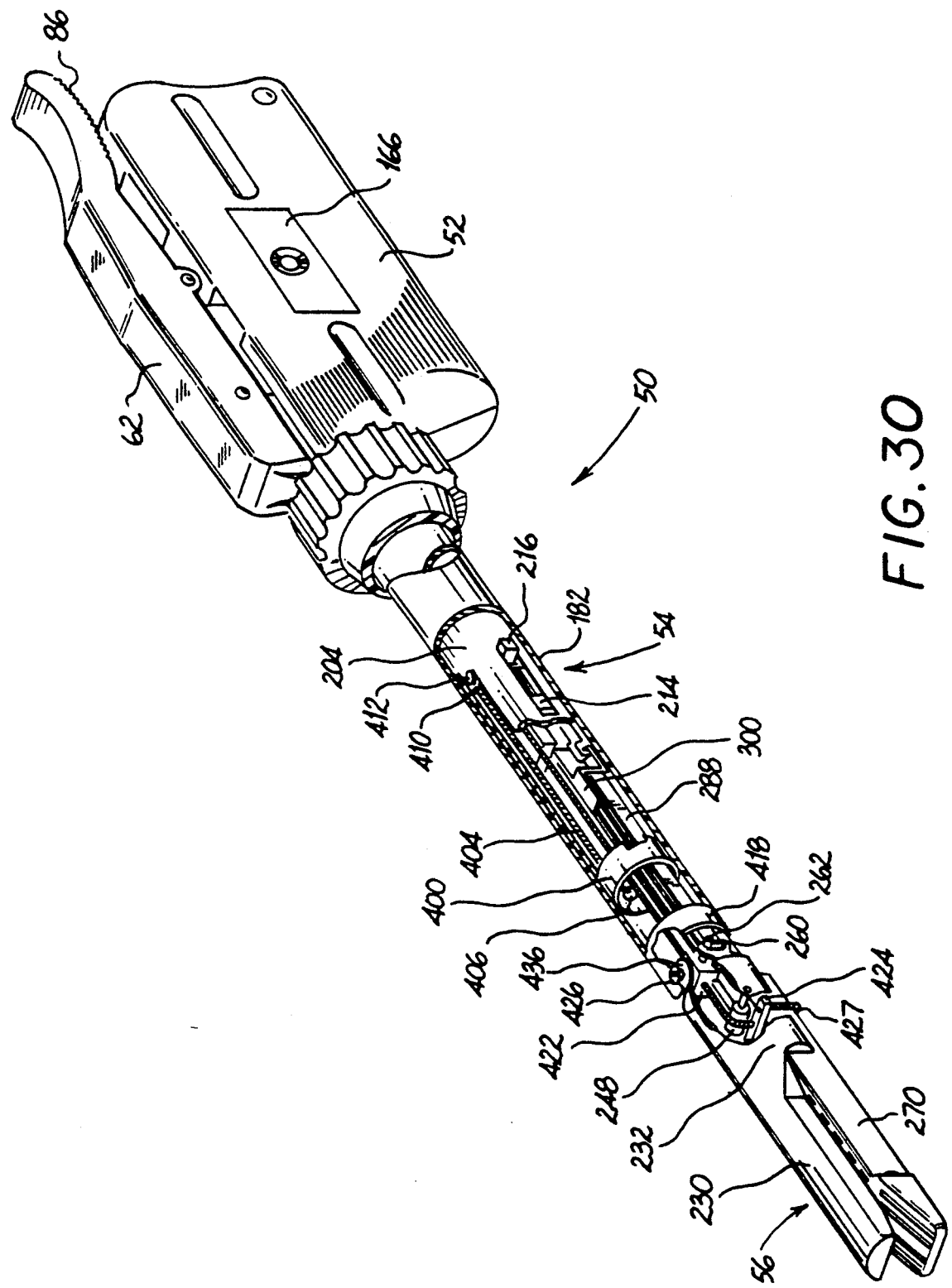
FIG. 30 is a perspective view, partially cut-away, of the surgical instrument of FIG. 1 with the anvil member in a closed position.

Referring to FIGS. 29 and 30, with the instrument properly oriented so that the tissue to be fastened is disposed between the open jaws of the instrument, i.e., between the tissue contacting surfaces of anvil member 56 and cartridge 280, the jaws are closed to clamp the tissue. Closure of the jaws is achieved as the surgeon presses down on articulating handle member 62, so as to slide tube collar 400 distally, via clamp tube 70, extension sleeve 204, and extension spacers 210, 212.

Figure 31:
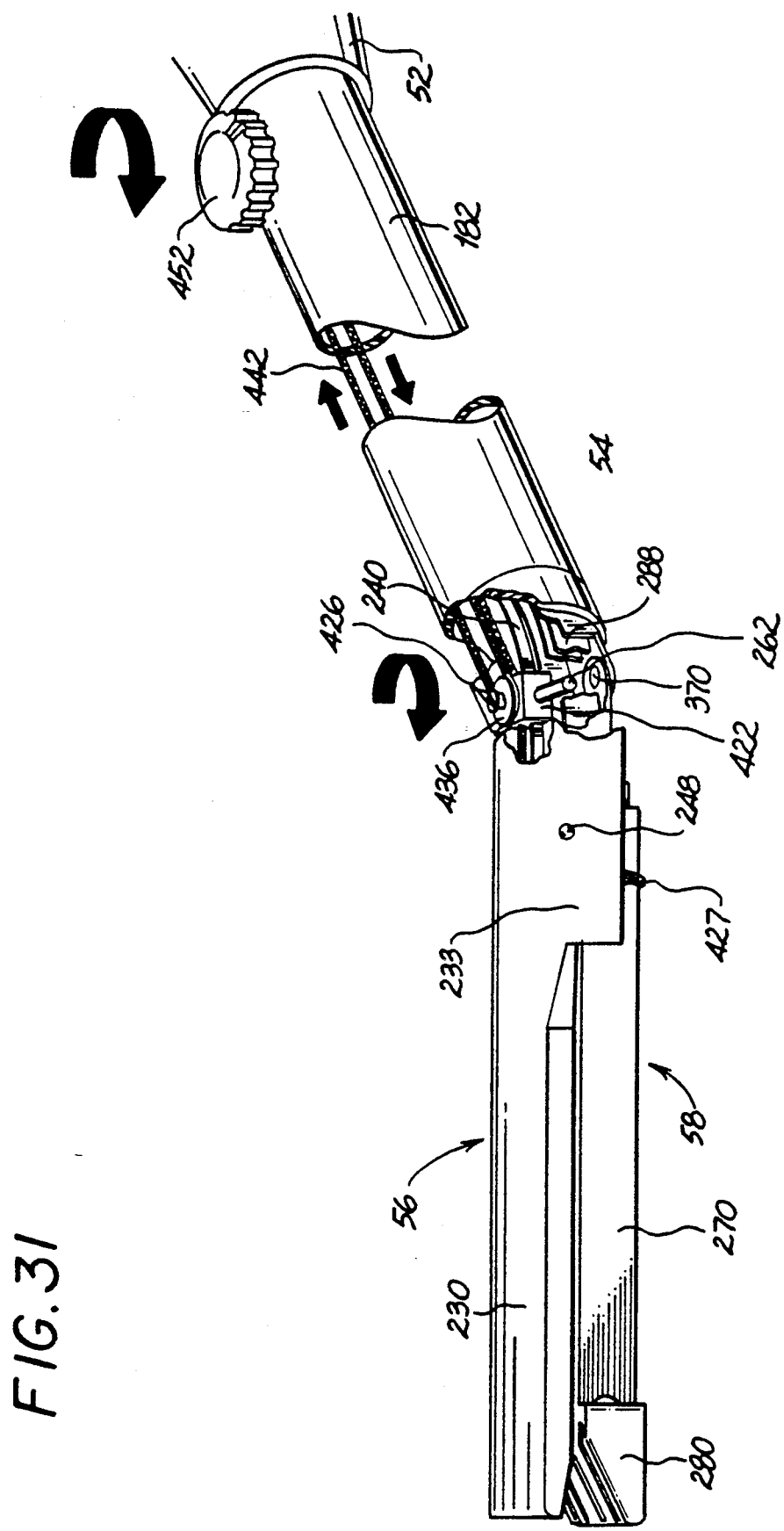
FIG. 31 is an enlarged perspective view, partially cut-away, of the cartridge assembly of the apparatus of FIG. 1 is a first articulated position.
Figure 32:
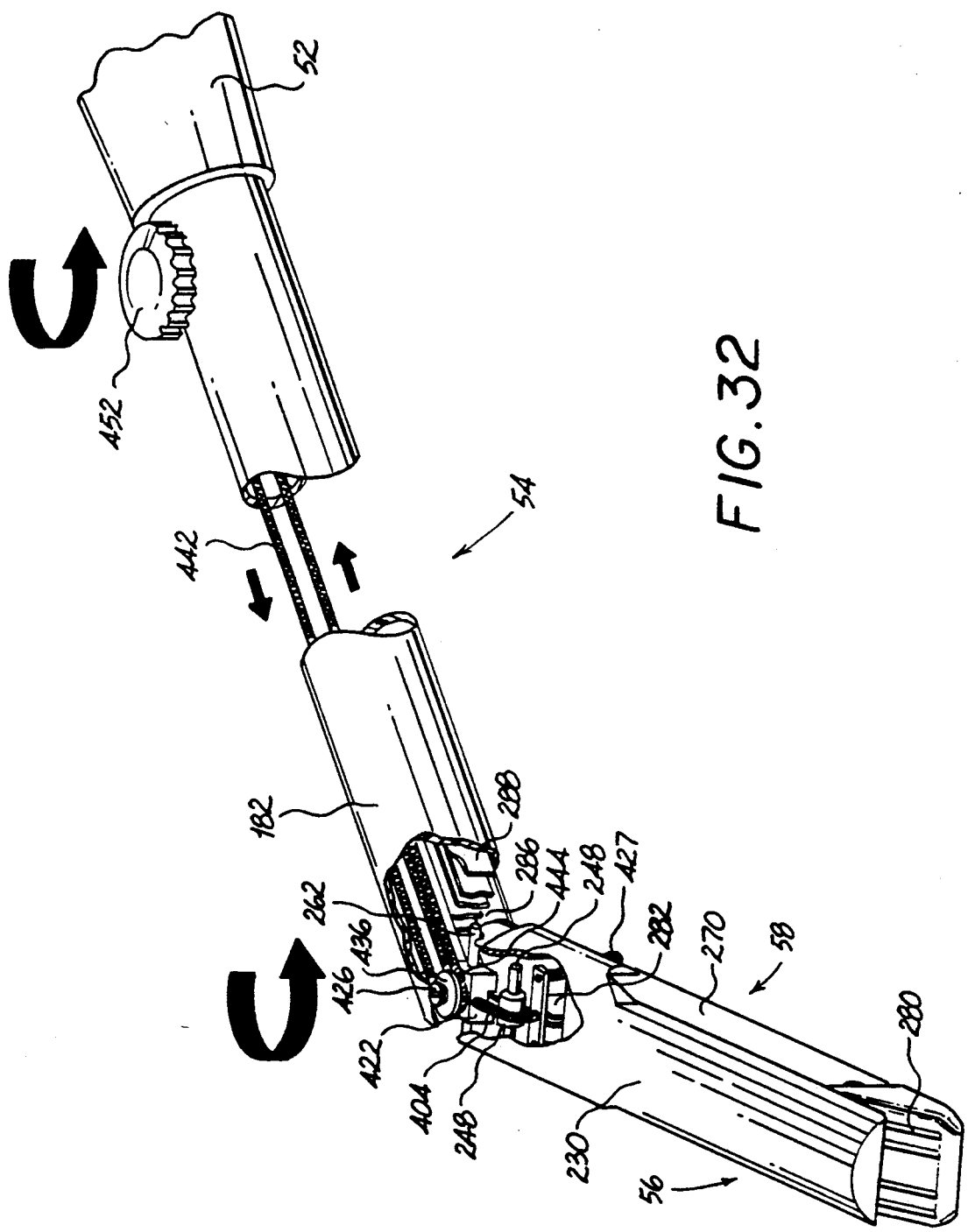
FIG. 32 is an enlarged perspective view, partially cut-away, of the cartridge assembly of the apparatus of FIG. 1 in a second articulated position.

The leading end of cable 404 is drawn in a distal direction as anchor ball 406 is maintained against partition wall 402. As the leading end of cable 404 is drawn distally, the intermediate section thereof which is turned about annular pulley 410 is drawn in a proximal direction. Consequently, the trailing end of cable 404 is urged in an upward direction, perpendicular to the longitudinal axis of elongated portion 54, as it turns about cylindrical pulley 248, thereby exerting a downward force upon pulley 248 and urging anvil member 56 to approximate toward the tissue engaging surface of cartridge assembly 58.

Where articulation is necessary or desired to orient the jaws prior to clamping, the forward housing 270 of cartridge assembly 58 may be articulated relative to the elongated portion 54 of apparatus 50 within a 90° sector of rotation, and in particular within a 45° sector of rotation on either side of the longitudinal axis of the elongated portion 54 of apparatus 50. Referring to FIG. 31, clockwise rotation of dial member 452 will result in clockwise articulation of forward housing 270 and anvil member 58. In particular, as dial member 452 is rotated, the lateral portions of articulation cable loop 426 translate in opposite longitudinal directions causing anchor ball 444 mounted in the shaft portion 438 of fixed capstan 436 of pivot block 422 to urge pivot block 422 in such a manner so as to rotate in a clockwise direction about threaded fastener 426. At such a time, the forward housing 270 pivots about rivet 370 relative to the rearward mounting portion 272 of cartridge assembly 58. Similarly, rotation of dial member 452 in a counterclockwise direction as shown in FIG. 32, will articulate cartridge assembly.

After closing the instrument jaws, the instrument is ready to be fired. When the surgeon is ready to emplace the staples and cut tissue, firing trigger 96 is depressed to actuate the pneumatic actuator 98 as discussed in detail above. Piston 104, attached to the proximal end of channel 192 is driven distally causing the camming surface of forked portion 194 to ride up and over projection 362 of the cam bar adapter 300 and drive the cam bar adapter in a distal direction. Thereupon, the cam bars 286 and 288 and knife 240 are driven longitudinally through the cartridge to sequentially drive and form staples.

As piston 104 contacts return springs 140, 142, pusher washers 186 are compressed on themselves and serve to store energy as the piston moves distally toward the cartridge assembly. This initial compression occurs in the range of between about 20 p.s.i. to about 150 p.s.i. and preferably within a range of about 30 p.s.i. to about 60 p.s.i. Near the end of the distal stroke of the piston 104, this stored energy is released to drive the cam bars 286 and 288 through the final distal limits of their travel within the longitudinal slots in the cartridge 250. At the distal extreme of the longitudinal stroke, the overhanging ledges 292 of cam bars 286 and 288 drop over the edge of the forward cartridge housing 270 thus abutting vertical surface thereof.

Figure 35:
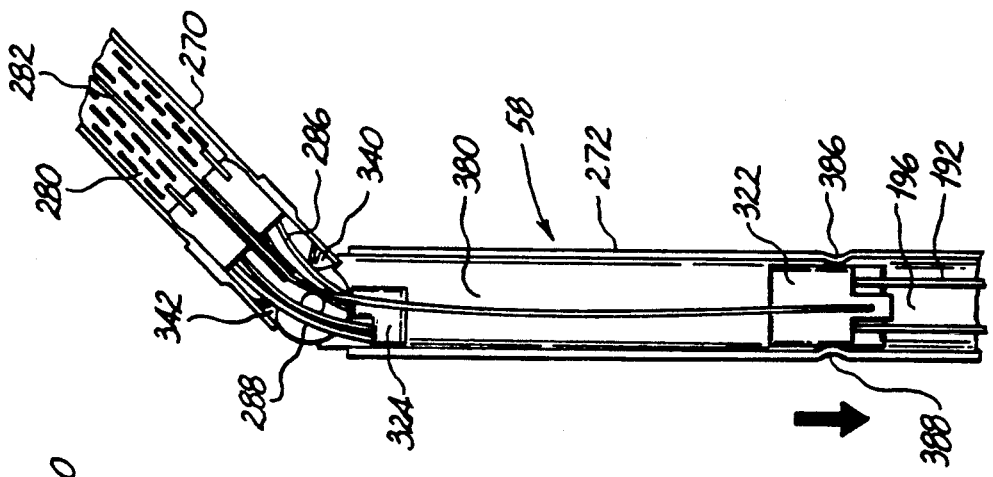
Figure 34:
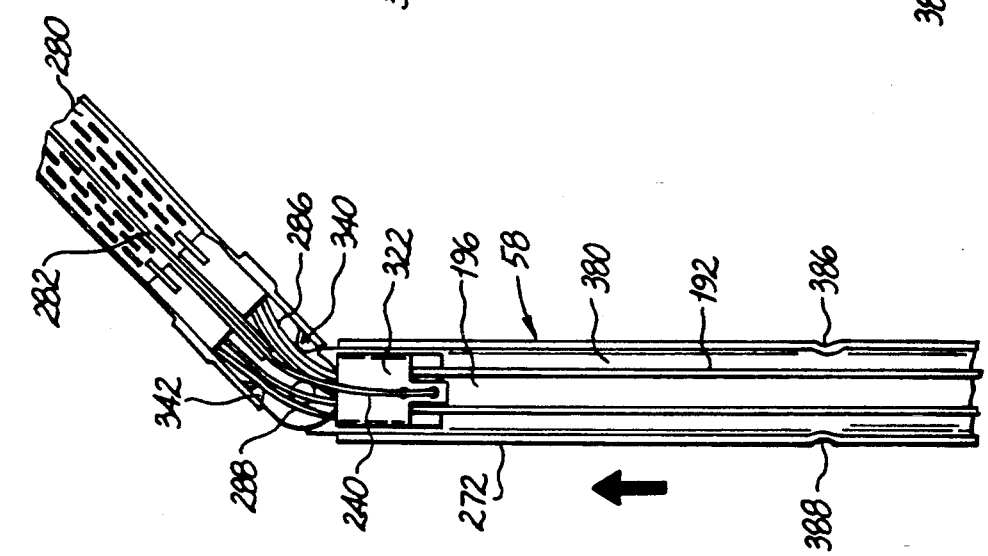
Figure 33:
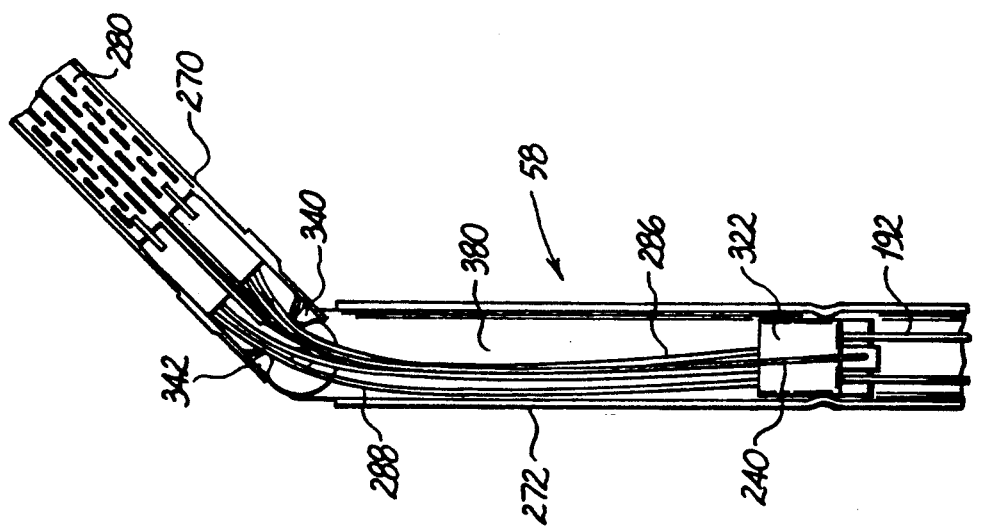

Referring to FIGS. 33 and 35, after firing, return springs 140, 142 engage piston 104 and return it to its original position. The return motion of piston 104 causes rocking lever 120 to be cammed aside by camming surface 144 of piston 104. Subsequently, the L-shaped support fixture and cam bars 286 and 288 are pulled out of cam bar adapter 320 and remain in position in the longitudinal slots of the cartridge 280. The cam bar adapter 320, with knife 240 attached, moves proximally within rearward cartridge mounting portion 272 until the outer edges of cam bar adapter 320 impinge on crimps 296.

The cam bar adapter 320 is held in place by crimps 296 while camming surfaces 198 and 200 of forked portion 194 causes the fork to ride up and disengage with projections 312 of the cam bar adapter 300. Channel member 192 continues to move in the proximal direction until it reaches its rest position. At this point, the entire cartridge assembly 58 is deactivated.

In the event that the surgeon should accidentally attempt to again fire the instrument without replacing the deactivated cartridge with a new unfired cartridge, the resulting distal longitudinal motion of the channel 192 moves abutting structure 202 into contact with rearward projection 290 effectively preventing further movement of forked portion 194 toward cam bar adapter 280.

After firing, articulating handle 62 is raised with the assistance of handle return spring 82 which action retracts collar tube 400. This retraction causes anvil 56 to move of engagement with cartridge assembly 58. Similarly, raising of articulating handle 62 causes cam slide 124 to move upward disengaging the pneumatic firing mechanism.

In order to replace the articulating cartridge assembly 58, the instrument is withdrawn from the patient. Thereafter, the cartridge assembly is removed from the elongated portion 54 of apparatus 50. To reinsert a new cartridge assembly, the proximal mounting portion 272 of cartridge assembly 58 is inserted into the distal end of elongated portion 54. The instrument is now ready for reinsertion and continued use.

Turning now to FIGS. 36 and 38, another preferred embodiment of the surgical apparatus of the subject invention is illustrated and is designated generally by reference numeral 500. Surgical apparatus 500 functions in much the same manner as the surgical instrument 50 previously described, with the exception of the mechanism for effectuating the articulation of the cartridge assembly 58. Specifically, the articulation mechanism of surgical apparatus 500 comprises two assemblies, including a parallel crank linkage assembly 505 disposed adjacent the cartridge assembly 58 at the distal end of elongated portion 54, and an actuation assembly, shown generally at 510, located adjacent the frame portion 52 of the apparatus at the proximal end of elongated portion 54. In the discussion which follows, both the linkage assembly 505 and the axial barrel cam assembly 510 will be described with respect to various embodiments. It will be appreciated however, by those having ordinary skill in the art, that any of the assemblies described herein may be modified to incorporate features shown in the various preferred embodiments.

Figure 40:
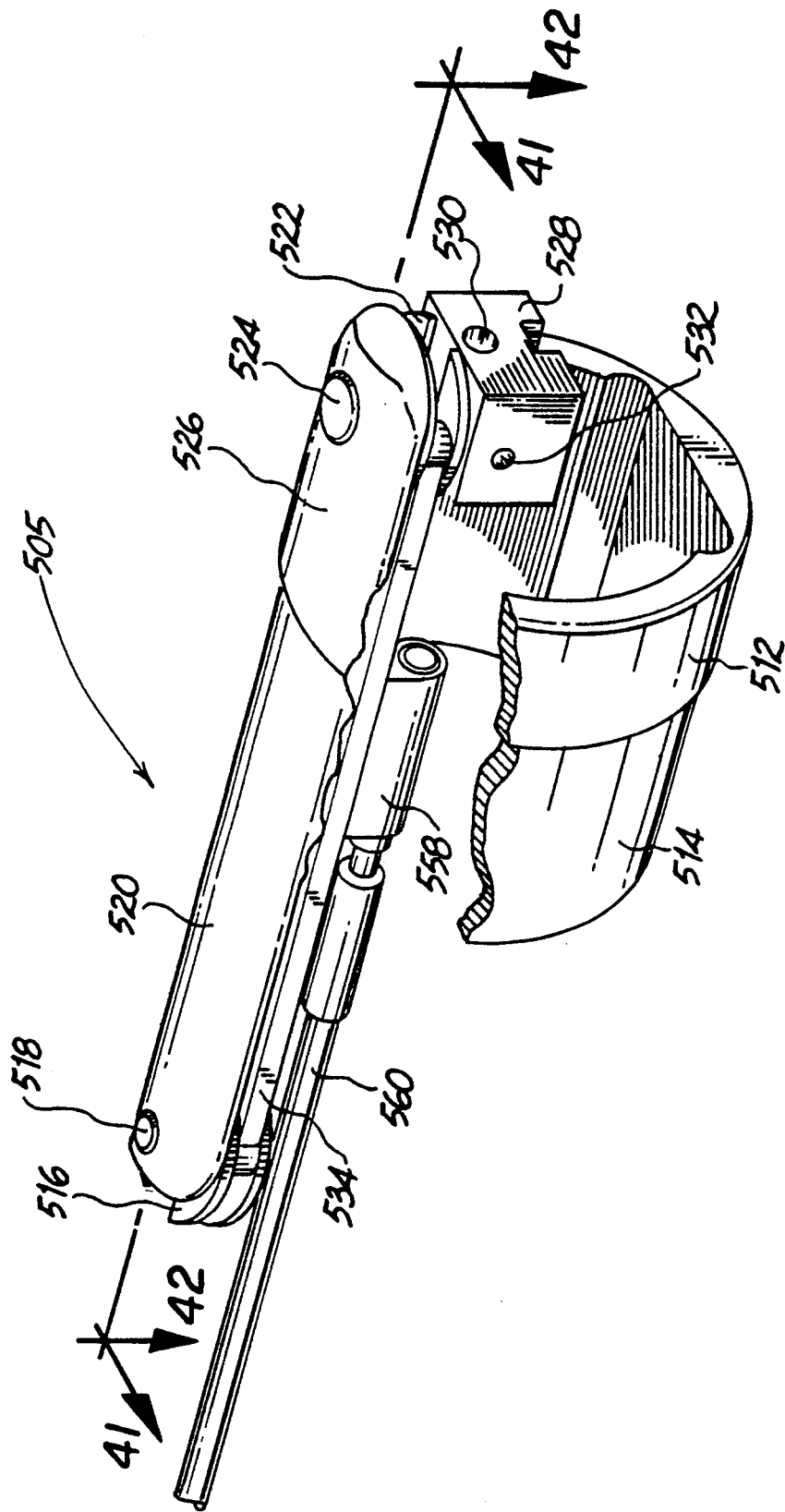
FIG. 40 is an enlarged perspective view, partially cut-away, of the mechanism for effectuating the articulation of the surgical instrument of FIG. 36.
Figure 45:
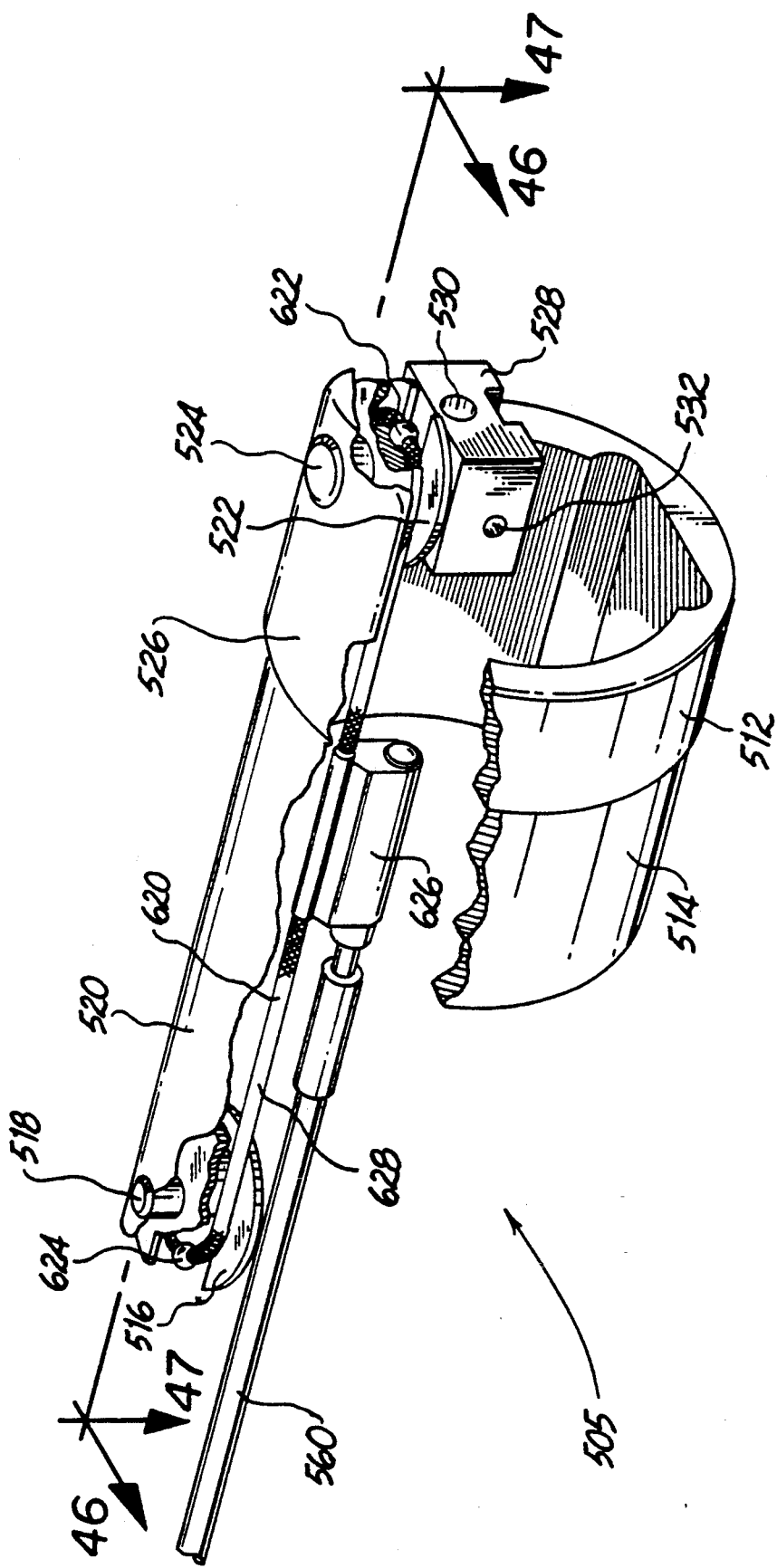
FIG. 45 is an enlarged perspective view, partially cut-away, of another embodiment of the mechanism for effectuating the articulation of the surgical instrument of FIG. 36.

Turning to FIGS. 40-42, the parallel crank linkage assembly 505 of surgical apparatus 500 is associated with a mounting collar 512 having an engaging portion 514 adapted for mounting within the distal end of cover tube 182. The linkage assembly 505 includes a proximal crank member 516 mounted for rotation about a pivot pin 518 which extends through the rearward flange portion 520 of mounting collar 512. Pivot pin 518 is disposed perpendicular to the longitudinal axis of elongated portion 54. Longitudinally spaced from proximal crank member 516, a distal crank member 522 is mounted for rotation about a pivot pin 524. Pivot pin 524 extends through the forward flange portion 526 of mounting collar 512 and is disposed parallel to pivot pin 518. Distal crank 522 is associated with a pivot block 528 having a longitudinal bore 530 extending therethrough for accommodating cable 404. As previously described herein, cable 404 is associated with moving anvil member 56 between an open position and a closed position for clamping tissue. Pivot block 528 is also provided with a transverse bore 532 for accommodating the transverse pin 262 about which anvil member 56 pivots as it is moved between its open and closed positions.

Linkage assembly 505 further comprises a pair of parallel coupler links 534 and 536 which operatively interconnect the proximal crank member 516 and distal crank member 522. Link 534 has a longitudinal span 538 with a transverse engaging slot 540 formed at a distal end thereof for engaging a pin 542 associated with distal crank 522, and a transverse engaging slot 544 is provided at the proximal end thereof for engaging another pin 546 associated with the proximal crank 516. Similarly, link 536 has a longitudinal span 548 with a transverse engaging slot 550 provided at the distal end thereof for engaging a pin 552 associated with the distal crank member 522, and a transverse slot 554 is formed at the proximal end thereof for engaging yet another pin 556 disposed on the proximal crank member 516. Of the two coupler links 534 and 536, link 534 defines a driver link, while link 536 defines a follower link. Moreover, driver link 536 is provided with a coupling 558, which depends from the undersurface thereof, intermediate span 538 for receiving and mounting the distal end of an elongated transmission rod 560. Transmission rod 560 extends through the elongated portion 54 of surgical apparatus 500 for transmitting reciprocal longitudinal motion to driver link 534 in response to manipulation of the axial barrel cam assembly 510. Transverse slots 540, 544, 550, and 554 permit coupler links 534 and 536 to remain parallel to a longitudinal axis of the linkage assembly 505 during transmission of the reciprocal longitudinal motion by rod 560.

Referring again to FIGS. 36–39, the actuation assembly 510 of surgical apparatus 500 comprises a generally cylindrical manipulator sleeve 562 disposed about the proximal section of elongated portion 54. Manipulator sleeve 562 is configured and dimensioned for axial movement with respect to the longitudinal axis of elongated portion 54. In particular, manipulator sleeve 562 may be rotated about the longitudinal axis of elongated portion 54 to rotate the cartridge assembly 58 relative to the frame portion 52 of apparatus 500, and reciprocally in a generally longitudinal direction for effectuating the articulation of cartridge assembly 58 so as to increase the range of operability of the instrument, which will be described in greater detail hereinbelow.

A barrel cam 564 having a substantially hemi-cylindrical configuration is associated with manipulator sleeve 562 and is configured and dimensioned for rotational movement as sleeve 562 is manipulated in a longitudinal direction to drive transmission rod 560. Relative rotational movement of barrel cam 564 is facilitated by the interaction of a cam follower pin 566 extending radially inward from manipulator sleeve 562, and a cam slot 568 defined in barrel cam 564. Cam slot 568 has a three stage configuration including an upper step region 570, a central step region 572, and a lower step region 574. When articulating the cartridge assembly 58 of surgical apparatus 500 in a counter-clockwise direction, sleeve 562 is manipulated in a proximal direction, moving cam follower pin 566 from the central step region 572, wherein cartridge assembly 58 is in substantial longitudinal alignment with the elongated portion 54 of the instrument, to the upper step region 570 of cam slot 568, to axially rotate barrel cam 564.

To articulate cartridge assembly 58 in clockwise direction, sleeve 562 is manipulated in a distal direction, moving cam follower pin 566 to the lower step region 574 of cam slot 568, and thereby axially rotating barrel cam 564. The longitudinal dimension of cam slot 568 can be modified depending upon the tactile sensation desired to be transmitted to the user of the instrument. In addition, an annular rib 563 (see FIG. 38) extending radially outward from the cover tube 182 of elongated portion 54, distal to manipulator sleeve 562, serves to prevent over-insertion of the elongated portion 54 of surgical apparatus 500 into a trocar or cannula device.

As stated briefly above, the rotational movement of barrel cam 564 is conveyed to transmission rod 560 for effectuating the articulation of cartridge assembly 58. This conveyance of rotational motion is accomplished by engaging an arm 580 formed at the proximal end of the transmission rod 560 within an angled drive slot 582 defined in barrel cam 564. Thus, as barrel cam 564 rotates in response to the translation of cam follower pin 566 within cam slot 568, transmission rod 560 is advantageously driven in a longitudinal direction as the peripheral walls of angled drive slot 582 are urged against the engaging arm 580 thereof. To secure the engagement of arm 580 within angled drive slot 582, a connective fitting 584 is mounted atop engagement arm 576 and is configured and dimensioned to move within longitudinal channel 585 formed in an inner surface of manipulation sleeve 562.

Barrel cam 564 is also provided with a pair of spaced apart transverse alignment slots 586 and 588 which are adapted and configured for cooperatively receiving a pair of guide pins 590 and 592. Guide pins 590 and 592 are associated with the outer tube 182 of elongated portion 54 and inhibit undesirable longitudinal shifting of the barrel cam 564 which may arise as sleeve 562 is manipulated. In addition, guide pins 590 and 592 achieve connection between the outer tube 182 of elongated portion 54 and the manipulator sleeve 662 via the interaction of cam follower pin 566 and cam slot 568. This connection is further assisted by the provision of a spring loaded locking mechanism associated with manipulator sleeve 562.

As best seen in FIGS. 37 and 39, the locking mechanism includes a lock ball 594 which is biased by a coiled spring 596 maintained within a cavity 598 formed within manipulator sleeve 562. Lock ball 594 is selectively engageable within a plurality of spaced apart notches disposed about the outer circumference of cover tube 182 and including a primary notch 600 corresponding to the cam follower pin 566 being disposed in the upper step region 570 of cam slot 568, a secondary notch 602 corresponding to cam follower pin 566 being disposed in the central step region 572 of cam slot 568, and a tertiary notch 603 corresponding to cam follower pin 566 being disposed in the lower step region 574 of cam slot 568. By lockingly engaging the cover tube 182 of elongated portion 54, rotation of manipulator sleeve 562 about the longitudinal axis of elongated portion 54 will effectuate remote rotation of cartridge assembly 58 relative to the frame portion 52 of surgical apparatus 500.

In use, as sleeve 562 is manipulated in a distal direction (see FIG. 38), transmission rod 560 will translate in a proximal direction with respect to elongated portion 54, pulling driver link 534 proximally as indicated by arrow "A" in FIG. 43. In response, distal crank member 522 is rotated about pivot pin 524, thereby turning pivot block 528 in a clockwise direction. As pivot block 528 is operatively connected to anvil member 56 through transverse pin 262, the forward housing 270 of cartridge assembly 58 is caused to articulate in a clockwise direction. Similarly, in response to manipulation of sleeve 562 in a proximal direction (see FIG. 36), transmission rod 560 will translate distally with respect to elongated portion 54, pushing driver link 534 distally as indicated by arrow "B" in FIG. 44. As a result, distal crank member 522 will turn pivot block 528 in a counter-clockwise direction, articulating the forward housing 270 of cartridge assembly 58 in a counter-clockwise direction.

Another preferred embodiment of the parallel linkage assembly 505 of the mechanism for effectuating the articulation of cartridge assembly 58 is illustrated in FIGS. 45–49. This assembly includes a looped cable 620, which replaces the parallel coupler links 534 and 536 discussed hereinabove, for operatively associating the spaced apart proximal and distal crank members 516 and 522, which, in this embodiment, serve primarily as a pair of capstans. A first ball-type fastener 622 is provided at the leading portion of cable loop 620 for securing the cable to distal crank member 522, and a second ball-type fastener 624 is provided at the trailing portion of cable loop 620 for fixing the cable to proximal crank member 516. A coupling 626 is rigidly mounted on the driving leg 628 of cable loop 620 for operatively receiving and retaining the distal end of transmission rod 560 so as to interconnect the actuation assembly 510 of surgical apparatus 500 to the linkage assembly 505 thereof.

Referring to FIG. 47, in use, the cable loop 620 is manipulated through longitudinal translation of transmission rod 560 in response to manipulation of barrel cam assembly 510 (see FIGS. 36 and 38). Thus, proximal translation of transmission rod 560, as indicated by arrow "C" in FIG. 48, will cause cable loop 620 to rotate in a clockwise direction, turning pivot block 528 in a clockwise direction to articulate the forward housing 270 of cartridge housing 58 through an arcuate path (see FIG. 38). Similarly, distal translation of transmission rod 560, as indicated by arrow "D" in FIG. 49, will cause cable loop 620 to rotate in a counter-clockwise direction, causing distal crank member 522 to pivot in a counter-clockwise direction. As a result, the forward housing 270 of cartridge assembly 58 will be moved arcuately in a counter-clockwise direction (see FIG. 36).

Figure 51:
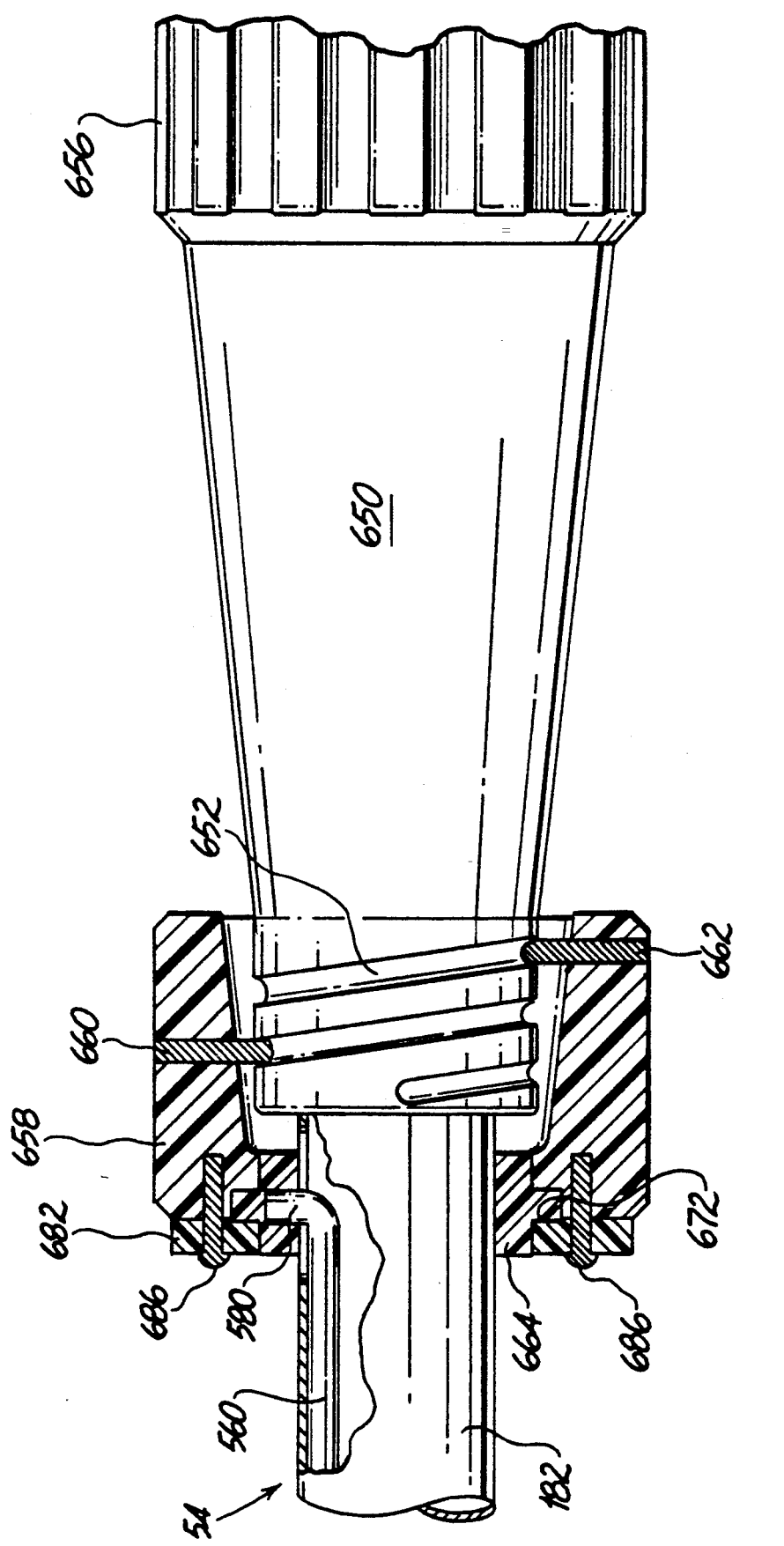
FIG. 51 is a side elevational view, partially cut-away, of the actuation member of FIG. 50.
Figure 52:
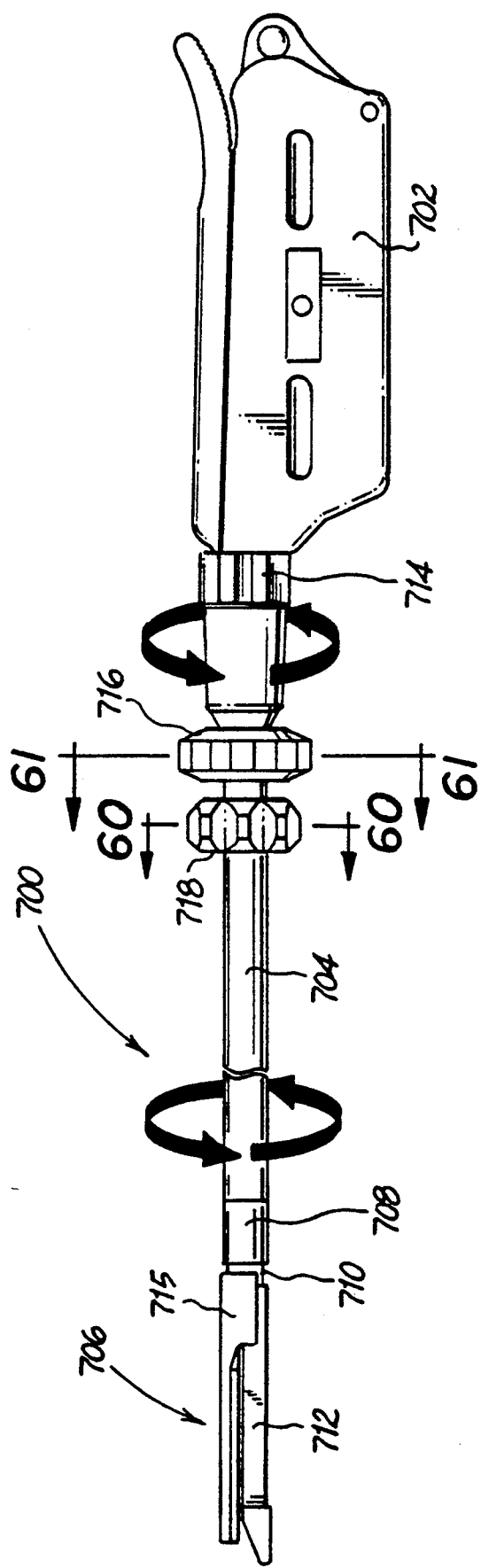
Figure 55:
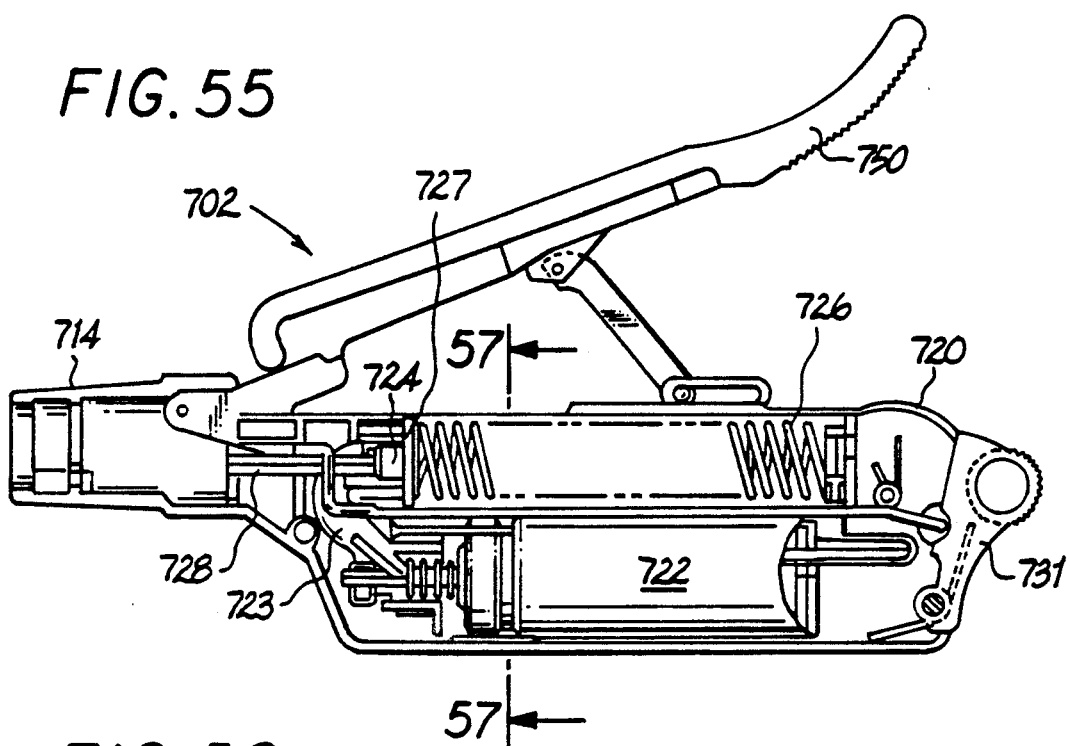
Figure 56:
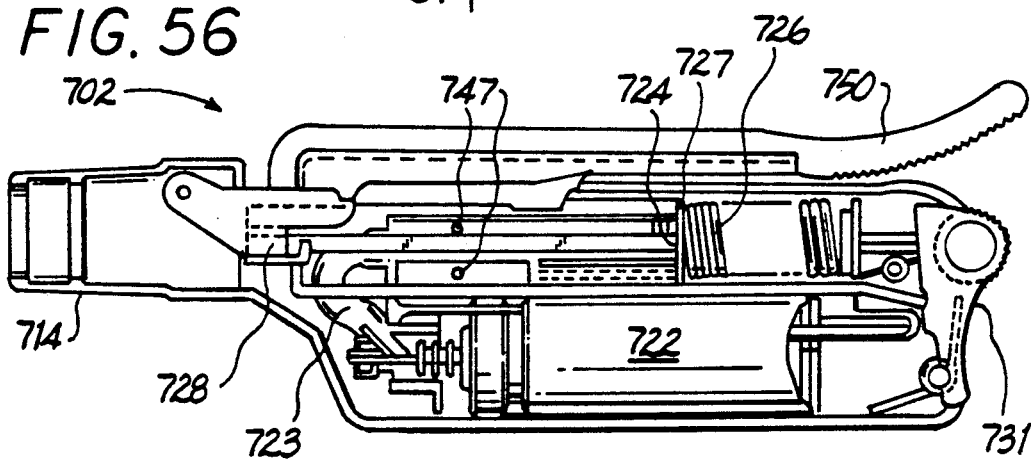
Figure 57:
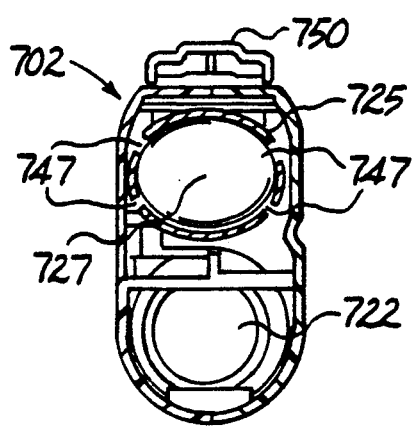
Figure 58:
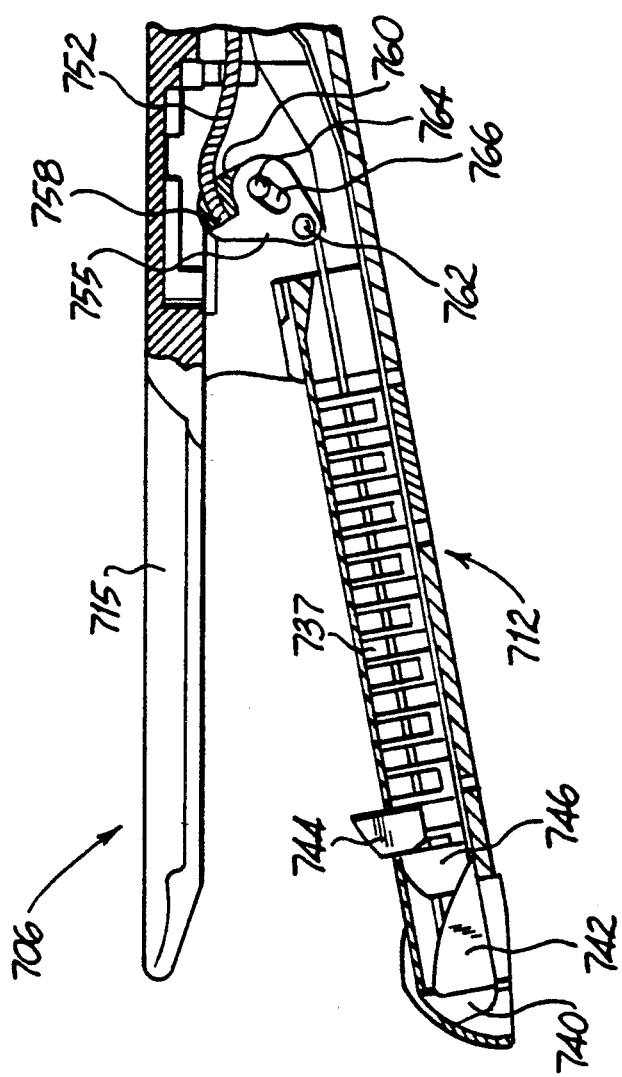
Figure 59:
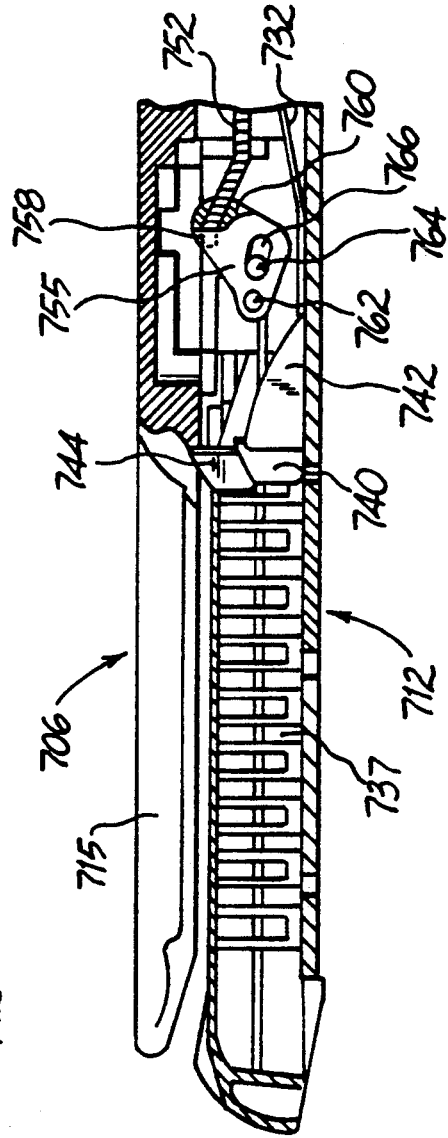
Figure 61:
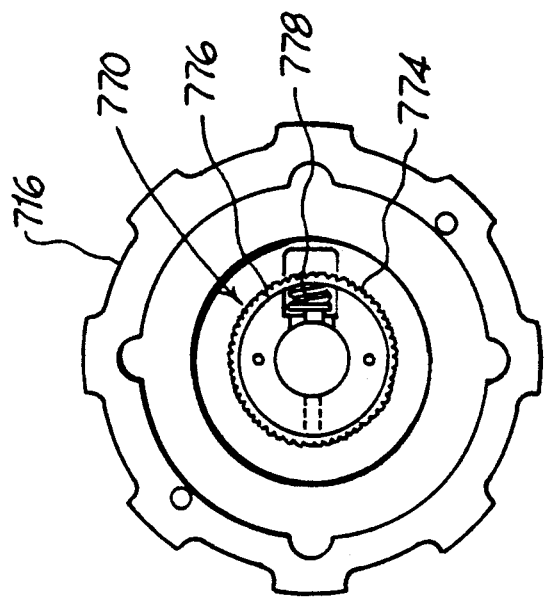
Figure 60:
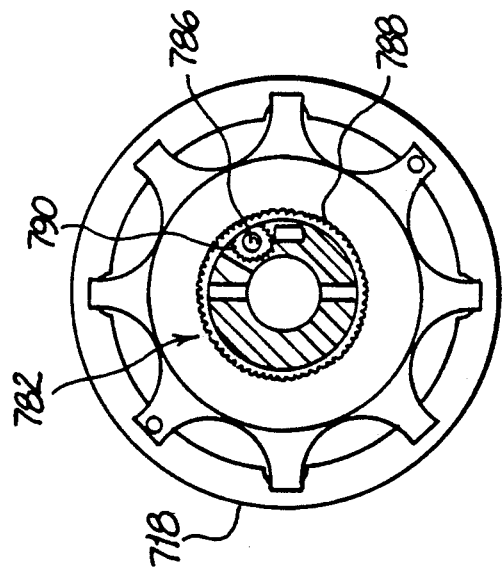
Figure 62:
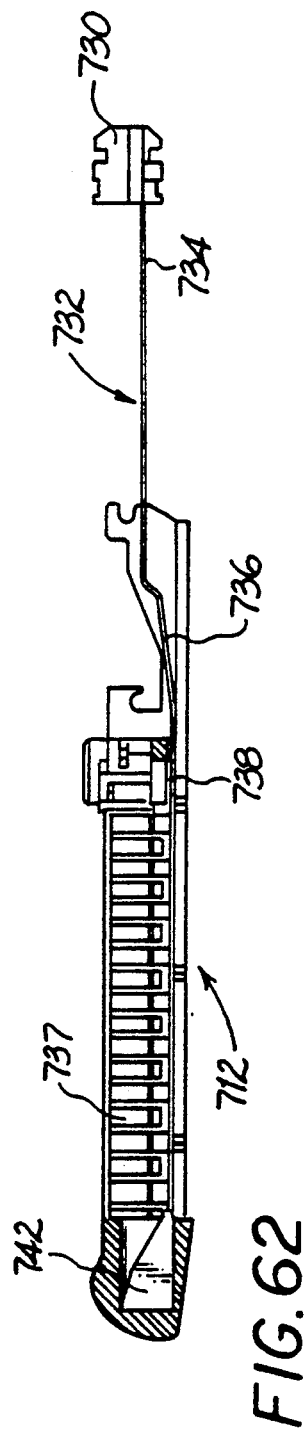

Another preferred embodiment of the actuation assembly 510 is illustrated in FIGS. 50 and 51, and is particularly adapted and configured for progressively articulating cartridge assembly 58 within an angular sector of rotation. This assembly comprises a sleeve member 650 disposed about the elongated portion 54 of surgical apparatus 500 adjacent the frame portion 52 thereof. A continuous helical track 652 is defined about the outer circumference of the distal end portion 654 of sleeve member 650, and a knurl 656 is formed at the proximal end portion of sleeve member 650. An annular knob member 658 is mounted coaxial with the distal end portion of sleeve member 650 and is provided with a pair of opposed and staggered follower pins 660 and 662 which are configured and positioned to travel within helical track 652 as knob member 658 is rotated relative to sleeve member 650 for effecting the progressive articulation of cartridge assembly 58.

A retainer ring 664 having an annular flange portion 668 is mounted within an annular groove 670 defined in knob member 658. Retainer ring 664 is also provided with an engagement port 672 for receiving the engaging arm 580 formed at the proximal end of transmission rod 560. A pair of diametrically opposed grooves 674 and 676 are formed in the interior of retainer ring 664 for engaging a pair of opposed corresponding keys 678 and 680 which extend radially outward from the cover tube 182 of elongated portion 54 adjacent sleeve member 650. Through this engagement, rotation of transmission rod 560 will be inhibited as knob member 658 is rotated to drive transmission rod 560 in a longitudinal direction for effectuating the progressive articulation of cartridge assembly 58. However, when sleeve member 650 is rotated about the longitudinal axis of elongated portion 54, the engagement of the keys 678 and 680 within the opposed grooves 674 and 676 will effectuate rotation of cartridge assembly 58 relative to the frame portion 52 of surgical apparatus 500. Finally, a securement ring 682 is fastened to the distal face 684 of knob member 658 by a plurality of threaded fasteners 686 for maintaining retainer ring 664 within annular groove 670.

It will be understood by those having ordinary skill in the art that various modifications or changes can be made to the various embodiments of the subject invention herein disclosed without departing from the spirit or scope thereof. For example, various sizes of the instrument are contemplated, as are various types of construction materials. Therefore, the above description should not be construed as limiting the invention, but merely as exemplifications of preferred embodiments thereof.

To the extent not already indicated, it will also be understood by those having ordinary skill in the art that any one of the specific embodiments herein described and illustrated may be further modified to incorporate features shown in other of the embodiments.

What is claimed is:

1. Apparatus for driving surgical fasteners comprising:
   a) a frame portion;
   b) a body portion extending from said frame portion;
   c) a cartridge assembly including:
      i) a proximal cartridge mounting portion maintained in a distal end portion of said body portion and defining a longitudinal axis extending therethrough; and
      ii) a distal cartridge housing portion movably connected to said proximal cartridge mounting portion on a pivot axis in alignment with and transverse to said longitudinal axis and having a tissue engaging surface thereon;
   d) articulation means associated with said body portion and actuable from said frame portion for moving said distal cartridge housing portion relative to said proximal cartridge mounting portion about said pivot axis;
   e) an anvil member having a fastener forming surface thereon, said anvil member mounted relative to said cartridge housing portion of said cartridge assembly so as to be movable between an open position wherein said fastener forming surface is spaced from said tissue engaging surface and a closed position wherein said fastener forming surface in is close cooperative alignment with said tissue engaging surface of said cartridge housing portion;
   f) means associated with said body portion for moving said anvil member between said open position and said closed position; and
   g) means for ejecting said surgical fasteners from said cartridge housing portion of said cartridge assembly, whereby said fasteners form against said fastener forming surface of said anvil member.

2. Apparatus as recited in claim 1, further comprising a pneumatic system disposed in said frame portion and including a self contained supply of pressurized gas and a pneumatic actuator mechanism associated with said gas supply, said pneumatic actuator operatively connected to said means for ejecting said surgical fasteners.

3. Apparatus as recited in claim 1, wherein said means for moving said anvil member between said open position and said closed position comprises a control system including a linkage mechanism associated at least in part with said frame portion and a cable mechanism for moving said anvil member.

4. Apparatus as recited in claim 3, wherein said linkage mechanism includes an articulating handle member associated with said frame portion and an extension member operatively connected to said articulating handle member and extending into said body portion for cooperation with said cable mechanism.

5. Apparatus as recited in claim 4, wherein said cable mechanism includes a cable member connected at a leading end thereof to a distal end portion of said extension member and connected at a trailing end thereof to said distal cartridge housing portion of said cartridge assembly, said cable member being operatively associated with said anvil member intermediate said leading and trailing ends thereof such that articulation of said handle member effects movement of said anvil member between said open position and said closed position.

6. Apparatus as recited in claim 5, wherein said cable mechanism includes a transverse pulley member connected adjacent a proximal end portion of said anvil member and an annular pulley member disposed within said body portion for directing the longitudinal translation of said cable member within said body portion.

7. Apparatus as recited in claim 1, wherein said articulation means includes a cable loop system having a cable loop fixed at a proximal section thereof to a rotation control member associated with said body portion and at a distal section thereof to a pivot block member pivotally mounted adjacent said distal end portion of said body portion, said pivot block member being operatively associated with said anvil member such that rotation of said control member enables said anvil member and said cartridge housing portion to translate relative to a longitudinal axis defined by said cartridge mounting portion of said cartridge assembly.

8. Apparatus as recited in claim 1, wherein said articulation means comprises, an actuation member disposed adjacent a proximal end of said body portion, and an articulating assembly including at least one reciprocally mounted linkage operatively engageable with said actuation member and said distal cartridge housing portion to translate reciprocal longitudinal motion of said at least one linkage into arcuate motion of said cartridge housing portion.

9. Apparatus as recited in claim 8, wherein said articulating assembly comprises a pair of rotatable cranks spaced along a longitudinal axis of said body portion, said cranks being operatively interconnected by a pair of parallel rigid links which transmit reciprocal longitudinal forces between said cranks.

10. Apparatus as recited in claim 8, wherein said articulating assembly comprises a pair of rotatable cranks spaced along a longitudinal axis of said body portion, said cranks being operatively interconnected by an endless cable loop, each end portion of said cable loop being fixed to a respective one of said pair of cranks, said cable loop being connected to said actuation member by a rigid link such that reciprocal axil motion of said rigid link is translated into arcuate motion of said distal cartridge housing portion.

11. Apparatus as recited in claim 8, wherein said actuation member is configured and dimensioned to effect progressive arcuate motion of said distal cartridge housing portion.

12. Apparatus as recited in claim 11, wherein said actuation member includes barrel cam structure for effectuating progressive arcuate motion of said distal cartridge housing portion.

13. Apparatus as recited in claim 1, wherein said means for ejecting said surgical fasteners further comprises pusher elements and at least one cam bar for actuating said pusher elements within said cartridge assembly to drive said surgical fasteners as said at least one cam bar traverses said cartridge assembly.

14. Apparatus as recited in claim 13, further comprising a knife adapted to move with said at least one cam bar.

15. Apparatus as recited in claim 13, wherein a proximal end portion of said at least one cam bar is fixedly maintained within a support member disposed in said cartridge mounting portion of said cartridge assembly, said support member being adapted for longitudinal translation within said cartridge assembly.

16. Apparatus as recited in claim 13, wherein a proximal end portion of said at least one cam bar is independent of and freely maintained within a support member disposed in said cartridge mounting portion of said cartridge assembly, said support member being adapted for translation within said cartridge assembly.

17. Apparatus as recited in claim 13, wherein said cartridge assembly further comprises bearing means for guiding the translation of said at least one cam bar when said distal cartridge housing portion of said cartridge assembly is articulated relative to said proximal cartridge mounting portion thereof.

18. Apparatus as recited in claim 17, wherein said bearing means comprises at least a pair of opposed bearing members disposed within said cartridge mounting portion adjacent a distal end thereof, each of said opposed bearing members having a bearing surface against which said at least one cam bar travels during translation within said cartridge assembly.

19. Apparatus as recited in claim 1, further comprising sealing means associated with said body portion for inhibiting the egress of gas therethrough.

20. Apparatus as recited in claim 19, wherein said sealing means comprises a plurality of sealing members disposed within said body portion.

21. Apparatus as recited in claim 1, further comprising means for rotating said cartridge assembly about a longitudinal axis of said body portion relative to said frame portion.

22. Apparatus for driving surgical fasteners comprising:
 a) a frame portion;
 b) an elongated portion extending from said frame portion;
 c) an articulating cartridge assembly including:
  i) a proximal cartridge mounting portion maintained in a distal end portion of said elongated portion and defining a longitudinal axis extending therethrough; and ii) a distal cartridge housing portion movably connected to said proximal cartridge mounting portion at a distal end thereof on a pivot axis in alignment with and transverse to said longitudinal axis and having a tissue engaging surface thereon;

d) articulation means operatively associated with said elongated portion and actuable from said frame portion for effectuating articulation of said cartridge assembly about said pivot axis;

e) an anvil member having a fastener forming surface thereon, said anvil member mounted relative to said distal cartridge housing portion of said cartridge assembly so as to be movable between an open position wherein said fastener forming surface is spaced from said tissue engaging surface and a closed position wherein said fastener forming surface is in close cooperative alignment with said tissue engaging surface;

f) means associated with said elongated portion for moving said anvil member between said open position and said closed position;

g) means for ejecting said surgical fasteners from said cartridge housing portion of said cartridge assembly so as to form against said fastener forming surface of said anvil member; and h) a pneumatic system associated with said frame portion and including a self contained supply of pressurized gas and a pneumatic actuator mechanism associated with said gas supply, said pneumatic system operatively connected to said means for ejecting said surgical fasteners.

23. Apparatus as recited in claim 22, wherein said means for moving said anvil member between said open position and said closed position comprises a linkage mechanism associated at least in part with said frame portion and a cable mechanism engageable with said linkage mechanism for moving said anvil member, said linkage mechanism including an articulating handle member associated with said frame portion and an extension member operatively connected to said articulating handle member and extending through said elongated portion to said cable mechanism, said cable mechanism being operatively associated with said anvil member.

24. Apparatus as recited in claim 23, wherein said cable mechanism includes a cable member connected at a leading end thereof to a distal end portion of said extension member and, at a trailing end thereof engaging said distal cartridge housing portion of said cartridge assembly, said cable member being operatively associated with said anvil member intermediate said leading and trailing ends thereof such that closure of said handle causes said anvil member to move between said open position and said closed positions.

25. Apparatus as recited in claim 24, wherein said cable mechanism includes a transverse pulley member connected to a proximal end portion of said anvil member and an annular pulley member disposed in a proximal end portion of said elongated portion for directing the longitudinal translation of said cable member within said elongated portion.

26. Apparatus as recited in claim 22, wherein said articulation means comprises a cable loop connected at a proximal section thereof to a rotation control member associated with said elongated portion and at a distal section thereof to a pivot block member mounted in a distal end portion of said elongated portion, said pivot block member being operatively associated with said anvil member such that rotation of said control member causes said anvil member and said cartridge housing portion to move relative to said cartridge mounting portion of said cartridge assembly about an axis perpendicular to the longitudinal axis of said elongated portion.

27. Apparatus as recited in claim 22, wherein said means for ejecting said surgical fasteners further comprises pusher elements and at least one cam bar removably maintained in a cam bar adapter for actuating said pusher elements within said cartridge assembly to drive said surgical fasteners as said cam bar adapter traverses said cartridge assembly.

28. Apparatus as recited in claim 27, further comprising a knife mounted in association with said cam bar adapter for moving with said at least one cam bar.

29. Apparatus as recited in claim 27, wherein a proximal end portion of said at least one cam bar is fixedly maintained within said cam bar adapter.

30. Apparatus as recited in claim 27, wherein a proximal end portion of said at least one cam bar is freely maintained within said cam bar adapter.

31. Apparatus as recited in claim 27, wherein at least a pair of opposed bearing members are disposed within said cartridge mounting portion adjacent a distal end thereof for guiding the translation of said at least one cam bar within said cartridge assembly at such times when said cartridge assembly is articulated.

32. Apparatus as recited in claim 22, further comprising a plurality of sealing members disposed in said elongated portion for inhibiting the egress of gas therethrough.

33. Apparatus as recited in claim 22, wherein said elongated portion is configured and dimensioned for endoscopic insertion into a cannula.

34. Apparatus as recited in claim 22, wherein said articulation means comprises, an actuation member disposed adjacent a proximal end of said elongated portion, and an articulating assembly including at least one reciprocally mounted linkage operatively engageable with said actuation member and said distal cartridge housing portion to translate reciprocal longitudinal motion of said at least one linkage into arcuate motion of said cartridge housing portion.

35. Apparatus as recited in claim 34, wherein said articulating assembly comprises a pair of rotatable cranks spaced along a longitudinal axis of said body portion, said cranks being operatively interconnected by a pair of parallel rigid links which transmit reciprocal longitudinal forces between said pair of cranks.

36. Apparatus as recited in claim 34, wherein said articulating assembly comprises a pair of rotatable cranks spaced along a longitudinal axis of said body portion, said cranks being operatively interconnected by an endless cable loop, each end portion of said cable loop being fixed to a respective one of said pair of cranks, said cable loop being connected to said actuation member by a rigid link such that reciprocal axial motion of said rigid link is translated into arcuate motion of said distal cartridge housing portion.

37. Apparatus as recited in claim 34, wherein said actuation member is configured and dimensioned to effect progressive arcuate motion of said distal cartridge housing portion.

38. Apparatus as recited in claim 22, further comprising means for rotating said articulating cartridge assembly about a longitudinal axis of said elongated portion relative to said frame portion.

* * * * *

UNITED STATES PATENT AND TRADEMARK OFFICE
CERTIFICATE OF CORRECTION

PATENT NO. : 5,326,013

DATED : July 5, 1994

INVENTOR(S) : David T. Green, Keith Ratcliff, Keith L. Milliman, Henry R. Sienkiewicz, Mitchell J. Palmer It is certified that error appears in the above-indentified patent and that said Letters Patent is hereby corrected as shown below:

IN THE DRAWINGS

Cancel Figs. 52-63

Signed and Sealed this

Fifth Day of September, 1995

Attest:

BRUCE LEHMAN

Attesting Officer

Commissioner of Patents and Trademarks